US011109796B2

(12) United States Patent
Han et al.

(10) Patent No.: US 11,109,796 B2
(45) Date of Patent: Sep. 7, 2021

(54) ELECTRONIC DEVICE WHICH CAN BE ADHERED TO SKIN AND METHOD FOR MANUFACTURING THE SAME

(71) Applicants: AMOREPACIFIC CORPORATION, Seoul (KR); MASSACHUSETTS INSTITUTE OF TECHNOLOGY, Cambridge, MA (US)

(72) Inventors: Jiyeon Han, Yongin-si (KR); Han-Wool Yeun, Cambridge, MA (US); Eunjoo Kim, Yongin-si (KR); Jeehwan Kim, Cambridge, MA (US)

(73) Assignees: AMOREPACIFIC CORPORATION, Seoul (KR); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 107 days.

(21) Appl. No.: 16/223,541

(22) Filed: Dec. 18, 2018

(65) Prior Publication Data
US 2020/0187848 A1    Jun. 18, 2020

(51) Int. Cl.
*A61B 5/00* (2006.01)
*H01L 41/047* (2006.01)
(Continued)

(52) U.S. Cl.
CPC ............ *A61B 5/442* (2013.01); *A61B 5/0077* (2013.01); *A61B 5/443* (2013.01); *A61B 5/6832* (2013.01);
(Continued)

(58) Field of Classification Search
CPC ............. H01L 41/1132; H01L 41/0475; H01L 41/253; H01L 41/29; H01L 41/312;
(Continued)

(56) References Cited

U.S. PATENT DOCUMENTS

2008/0283616 A1*  11/2008  Yukawa ............... H01L 27/1052
                                                                235/492
2013/0041235 A1    2/2013  Rogers et al.
(Continued)

FOREIGN PATENT DOCUMENTS

CN    107179336    9/2017
JP    2009542025   11/2009
(Continued)

OTHER PUBLICATIONS

Akihito Miyamoto, et al., "Inflammation-free, gas-permeable, lightweight, stretchable on-skin electronics with nanomeshes", Nature Nanotechnology, vol. 12, (2017), pp. 1-8.
(Continued)

*Primary Examiner* — Tuan A Hoang
(74) *Attorney, Agent, or Firm* — Cantor Colburn LLP

(57) ABSTRACT

Exemplary embodiments relate to a skin-adherable electronic device including a semiconductor circuit unit including a circuit element including an electrode and an interconnect, and a semiconductor device including an insulating layer and an active layer; and a flexible patch that can adhere to skin and including a plurality of through-holes, wherein the insulating layer includes a plurality of through-holes corresponding to the plurality of through-holes of the flexible patch, and a method of manufacturing the same. When the active layer is made of a piezoelectric material, the electronic device may be used as a skin sensor that can acquire skin deformation and/or elasticity information.

31 Claims, 47 Drawing Sheets

(51) Int. Cl.
*H01L 41/08* (2006.01)
*H01L 41/312* (2013.01)
*H01L 41/253* (2013.01)
*H01L 41/29* (2013.01)
*H01L 41/113* (2006.01)
*H01L 41/187* (2006.01)

(52) U.S. Cl.
CPC ........ *H01L 41/0475* (2013.01); *H01L 41/081* (2013.01); *H01L 41/1132* (2013.01); *H01L 41/187* (2013.01); *H01L 41/253* (2013.01); *H01L 41/29* (2013.01); *H01L 41/312* (2013.01); *A61B 2562/12* (2013.01)

(58) Field of Classification Search
CPC .... A61B 5/442; A61B 5/6832; G01N 27/121; G01N 27/125
See application file for complete search history.

(56) References Cited

U.S. PATENT DOCUMENTS

| | | | | |
|---|---|---|---|---|
| 2015/0351689 | A1* | 12/2015 | Adams | A61B 5/6833 600/300 |
| 2017/0021172 | A1* | 1/2017 | Perez | A61B 5/42 |
| 2017/0071172 | A1* | 3/2017 | Derrick | A01K 63/006 |
| 2017/0136264 | A1 | 5/2017 | Hyde et al. | |
| 2020/0009690 | A1* | 1/2020 | Hill | B23K 26/38 |
| 2020/0337641 | A1* | 10/2020 | Wang | A61B 5/6833 |

FOREIGN PATENT DOCUMENTS

| | | |
|---|---|---|
| KR | 1020150030225 | 3/2015 |
| KR | 101746492 | 6/2017 |
| WO | 2008000556 | 1/2008 |

OTHER PUBLICATIONS

Angelo Landriscina, et al., "Nanotechnology, Inflammation and the Skin Barrier: Innovative Approaches for Skin Health and Cosmesis", Cosmetics, vol. 2, (2015), pp. 177-186.

Canan Dagdeviren, et al., "Conformal piezoelectric systems for clinical and experimental characterization of soft tissue biomechanics", Nature Materials, vol. 14, (Jul. 2015), pp. 728-736.

Moon Kee Choi, et al., "Cephalopod-Inspired Miniaturized Suction Cups for Smart Medical Skin", Adv. Healthcare. Mater., vol. 5, No. 80, (2015), pp. 1-33.

Qilin Hua, et al., "Skin-inspired highly stretchable and conformable matrix networks for multifunctional sensing", Nature Communications, vol. 9, No. 244 (2018), pp. 1-11.

Sihong Wang, et al., "Skin electronics from scalable fabrication of an intrinsically stretchable transistor array", Nature, vol. 555, No. 83, (2018), pp. 1-17.

* cited by examiner (S401)

(S410)

(S430)

(S450)

(S411)

(S413)

(S415)

Si substrate furrow (S1201)

(S1211)

(S1213)

(S1215)

(S1230)  alignment key (S1240)

(S1250)

(S1270)

(S1301)

(S1309)

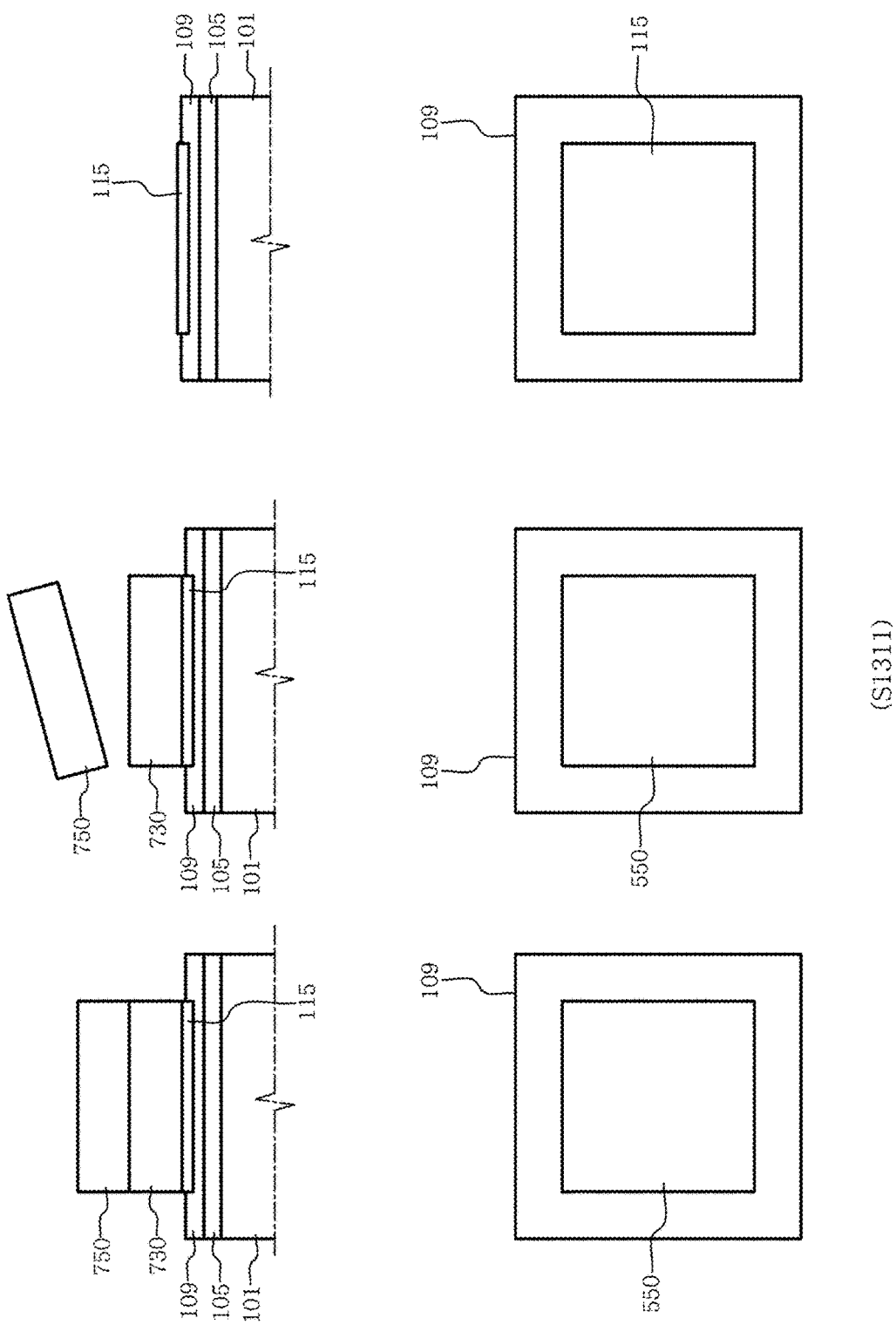

(S1312)

(S1313)

(S1315)

(S1330)

Through-hole alignment key (S1340)

(S1350)

(S1360)

(S1370)

ELECTRONIC DEVICE WHICH CAN BE ADHERED TO SKIN AND METHOD FOR MANUFACTURING THE SAME

BACKGROUND

1. Field

Exemplary embodiments relate to a skin-attachable electronic device, and more particularly, to an electronic device including a semiconductor circuit unit having a semiconductor device (for example, including an active layer) and a circuit element (for example, including an electrode and/or an interconnect), and a skin-adherable flexible patch used as a substrate onto which the semiconductor circuit unit is integrated, and a method of manufacturing the same. In particular, the flexible patch used as a substrate for circuits has a plurality of through-holes and thus has high air permeability and strong adhesiveness.

2. Description of the Related Art

As the industrial and economic development improves the quality of life, a majority of modern people desire younger-looking and more beautiful faces and bodies simply beyond healthy living. To meet the modern people's desires, there is an increasing interest in skin-conformable electronic sensing technology (such as, for example, skin sensors) that enables continuous monitoring of health conditions, in particular, skin conditions.

In general, to acquire information associated with skin such as skin changes and conditions, a skin sensor is adhered to a target's skin. However, skin is an outer covering organ that is disposed at the outermost of human body and has the largest area, and skin does a variety of pore-based physiological behaviors, such as sweat, sebum secretion and volatile organic excretion, essential to preserving homeostasis in the human body made up of compounds. A skin sensor that adheres to skin should be manufactured, considering the above-described biological properties of skin.

Accordingly, high quality skin sensors for monitoring long-term health conditions or skin conditions need to have both adhesiveness and air permeability as essential requirements.

The conventional skin sensors are manufactured using a polymer substrate of PI or PET having poor permeability, so they have posed the problem: when a skin sensor is adhered to skin, the skin sensor blocks the skin pores and inhibits the physiological behaviors of skin, causing inflammation and irritation. When a chemical adhesive is additionally used for strong adhesion between the skin sensor and the skin, inflammation may become worse. The infected skin loses the protection function against viruses, which may cause secondary inflammation or complications. Additionally, due to the elastic modulus of the polymer substrate that is about 1000 times higher than the skin, the adhesive strength to the skin is very low, failing to adhere to the skin for a long term, or resulting in very low efficiency of re-adhesion.

To overcome this problem, attempts have been made to develop skin sensors of which a surface that adheres to skin has a micro structure such as octopus suckers or gecko feet based on elastomer including PDMS that is similar to the mechanical properties of skin, but the micro structure is a non-penetrating structure that only exists on the surface. Accordingly, the manufacturing process is complex, and it is difficult to reduce the size.

Additionally, in manufacturing the elastomer-based skin sensor, because elastomer is deformable and softer than a silicon substrate commonly used, it is difficult to integrate a circuit element of the skin sensor onto the elastomer.

RELATED LITERATURES

Patent Literatures (Patent Literature 1) KR 10-1746492 B1

SUMMARY

According to an aspect of the present disclosure, there is provided an electronic device including a semiconductor circuit unit having a circuit element and a skin-adherable flexible patch used as a substrate onto which the semiconductor circuit unit is integrated.

Additionally, there is provided a method of manufacturing the electronic device.

In one aspect, there is provided a skin-adherable electronic device, comprising: a semiconductor circuit unit—the semiconductor circuit unit including a circuit element including at least one of an electrode and an interconnect; and a semiconductor device including an insulating layer and an active layer; and a flexible patch including a plurality of through-holes, wherein the flexible patch can adhere to skin, wherein the insulating layer includes a plurality of through-holes corresponding to the plurality of through-holes of the flexible patch.

In an embodiment, wherein the plurality of through-holes includes circular through-holes, and spacing between the plurality of through-holes is less than 60 μm.

In an embodiment, wherein the plurality of through-holes further includes dumbbell through-holes.

In an embodiment, wherein the plurality of through-holes includes a combination of a first through-hole having a first diameter and a second through-hole having a second diameter, wherein the first diameter is larger than the second diameter, and the second through-hole is disposed around the first through-hole.

In an embodiment, wherein the flexible patch is placed on the active layer so as to match the plurality of through-holes of the flexible patch to the plurality of through-holes of the insulation layer.

In an embodiment, wherein the active layer is a made of a material including AlN or GaN.

In an embodiment, wherein the circuit element includes a first electrode and a second electrode disposed opposite to the first electrode, the first electrode includes at least one first bar, the second electrode includes at least one second bar, and the first bar has a plane of zigzag shape and extends toward the second electrode, and the second bar has a plane of zigzag shape and extends toward the first electrode.

In an embodiment, wherein the zigzag shape of the first bar or the second bar includes a hinge pattern disposed at a point where an extension direction of the bar changes.

In an embodiment, wherein the flexible patch includes a first flexible layer having a first elastic modulus and a second flexible layer having a second elastic modulus, and the first elastic modulus is lower than the second elastic modulus.

In an embodiment, wherein a thickness (t1) of the first flexible layer and a thickness (t2) of the second flexible layer are determined based on the following equation:

$$W \geq W_c$$

where $W_c = E_{eq} * t^3 / (24R^2)$, $$W = \frac{4\gamma_{dPatch}\,\gamma_{dskin}}{\gamma_{dPatch} + \gamma_{dskin}} + \frac{4\gamma_{pPatch}\,\gamma_{pskin}}{\gamma_{pPatch} + \gamma_{pskin}},$$

$$E_{eq} = \left(\frac{t_1}{t_1 + t_2}\right)E_1 + \left(\frac{t_2}{t_1 + t_2}\right)E_2$$

$$t = t_1 + t_2,$$

where t denotes a thickness of the flexible patch, $E_1$ denotes an elastic modulus of the first flexible layer, $E_2$ denotes an elastic modulus of the second flexible layer, R denotes a curvature of the flexible patch adhered to the skin, $\gamma_{dSkin}$ denotes a dispersive component of contact surface of the skin, $\gamma_{dPatch}$ denotes a dispersive component of contact surface of the patch, $\gamma_{pSkin}$ denotes a polar component of contact surface of the skin, and $\gamma_{pPatch}$ denotes a polar component of contact surface of the patch.

In another aspect, a method of manufacturing a skin-adherable electronic device, comprising: forming a sacrificial layer on a first substrate; forming a semiconductor circuit unit including a semiconductor device and a circuit element on the sacrificial layer; bonding a flexible patch including a plurality of through-holes onto the semiconductor circuit; and etching the sacrificial layer to manufacture an electronic device including the semiconductor circuit unit and the flexible patch.

In an embodiment, wherein the forming the semiconductor circuit unit comprises: forming a circuit element on the sacrificial layer—the circuit element including at least one of an electrode and an interconnect; forming an insulating layer on the circuit element—the insulating layer being formed to have a plurality of through-holes corresponding to the plurality of through-holes of the flexible patch; and forming an active layer on the insulating layer.

In an embodiment, wherein the forming the active layer comprises: forming an active layer on a second substrate; forming a stressor layer on the active layer; placing a tape on the stressor layer; peeling the active layer and the stressor layer off from the second substrate using the tape; transferring the peeled active layer and stressor layer onto the insulating layer—the peeled active layer being transferred onto the insulating layer; and peeling the stressor layer off from the active layer using the tape.

In an embodiment, wherein the stressor layer is a multi-layer, and the forming the stressor layer comprises: forming a first stressor layer on the active layer by evaporation; forming a second stressor layer on the first stressor layer by sputtering deposition; and forming a third stressor layer on the second stressor layer by sputtering deposition.

In an embodiment, wherein the second stressor layer is made of a material including Al, and the third stressor layer is made of a material including Ni.

In an embodiment, wherein the first stressor layer is made of a material including Ni or AgNi.

In an embodiment, wherein the bonding further comprises applying the pressure between the flexible patch and the semiconductor circuit unit.

In an embodiment, the method may further comprising: performing plasma treatment of the semiconductor circuit unit and the flexible patch before bonding.

In an embodiment, wherein the bonding comprises placing the flexible patch on the active layer so as to match the plurality of through-holes of the flexible patch to the plurality of through-holes of the insulation layer.

In an embodiment, wherein the sacrificial layer is made of any one material of Ni, Cr, Al and their combinations.

In an embodiment, wherein the forming the semiconductor circuit unit comprises: forming an active layer on the sacrificial layer; forming an insulating layer on the active layer; and forming a circuit element on the insulating layer—the circuit element includes at least one of an electrode and an interconnect.

In other aspect, a method of manufacturing a skin-adherable electronic device, comprising: forming a sacrificial layer on a first substrate; forming a semiconductor circuit unit including a circuit element and a semiconductor device on the sacrificial layer; forming a flexible patch layer on the semiconductor circuit unit; contacting a mold including furrows that form a plurality of through-holes with the flexible patch layer—a region of the mold except the furrows passing through the flexible patch layer; and etching the sacrificial layer to manufacture an electronic device.

In an embodiment, wherein the forming the semiconductor circuit unit on the sacrificial layer comprises: forming a circuit element on the sacrificial layer—the circuit element including at least one of an electrode and an interconnect; forming an insulating layer on the circuit element—the insulating layer including a plurality of through-holes corresponding to the plurality of through-holes of the flexible patch layer formed by the mold; and forming an active layer on the insulating layer.

In an embodiment, wherein the forming the semiconductor circuit unit on the sacrificial layer comprises: forming an active layer on the sacrificial layer; forming an insulating layer on the active layer—the insulating layer including a plurality of through-holes corresponding to the plurality of through-holes of the flexible patch layer formed by the mold; and forming a circuit element on the insulating layer—the circuit element including at least one of an electrode and an interconnect.

In an embodiment, the method may further comprising: before forming an active layer, forming a polyamide layer on the sacrificial layer; and after contacting the molding with the flexible patch layer, removing the polyamide layer.

In an embodiment, wherein the forming the active layer comprises forming the active layer on the polyamide layer using a transfer structure.

In an embodiment, the method may further comprising: patterning the active layer such that a width of the active layer is smaller than a width of through-holes that will be formed by the mold.

In an embodiment, wherein the contacting the mold including the plurality of furrows with the flexible patch layer comprises heating the flexible patch layer.

In an embodiment, wherein a surface of the mold has furrows that can form a plurality of circular through-holes and a plurality of dumbbell through-holes and their combinations.

In an embodiment, wherein a surface of the mold has furrows that can form a plurality of circular through-holes and a plurality of dumbbell through-holes.

In an embodiment, the method may further comprising: forming at least one alignment key for alignment of the penetrating mold, wherein the alignment key has a height, and the mold further includes at least one key hole corresponding to a plane of the alignment key.

In an embodiment, wherein a width of the furrows that form the through-holes is less than 60 μm.

In an embodiment, wherein the forming the flexible patch layer comprises: forming a third flexible layer having a third elastic modulus on the semiconductor circuit unit; and forming a fourth flexible layer having a fourth elastic modulus on the third flexible layer, and the fourth elastic modulus is lower than the third elastic modulus.

The method of manufacturing an electronic device according to an aspect of the present disclosure may manufacture an electronic device by bonding a semiconductor circuit unit including various circuit elements such as electrodes and interconnects and a semiconductor device onto a flexible patch configured to adhere to skin.

In particular, it is possible to manufacture an electronic device in which a circuit element and a semiconductor device are disposed on a flexible patch. Patches that adhere to skin surface should be flexible. The present disclosure can solve the problem occurring when directly integrating a circuit element and/or a semiconductor device onto a flexible patch through a reverse process of integrating semiconductor circuits in a reverse order.

The flexible patch of the electronic device includes a plurality of through-holes, and can have high air permeability and strong adhesiveness. Accordingly, the electronic device does not affect the skin condition even when worn on the skin.

Additionally, the plurality of through-holes may have different sizes to maximize the function of the semiconductor circuit disposed on the flexible patch.

In an embodiment, when the semiconductor device of the electronic device includes a piezoelectric material, the electronic device may be used as a skin sensor that adheres to skin to acquire skin deformation and/or elasticity information. The piezoelectric material used for deformation sensing is disposed in a larger through-hole, and thus the skin sensor can acquire skin deformation information caused by the physiological behaviors of skin more efficiently.

In another embodiment, when the semiconductor device of the electronic device is configured to respond to light, the electronic device may be used as an optical sensor or an image sensor for skin surface.

In still another embodiment, when the semiconductor device of the electronic device is configured to respond to moisture, the electronic device may be used as a moisture sensor to measure a moisture loss of skin.

BRIEF DESCRIPTION OF THE DRAWINGS

To describe the technical solutions of the embodiments of the present disclosure or related art more clearly, drawings required for describing the embodiments will be briefly introduced below. To identify similar elements shown in one or more drawings, the same reference numeral is used. It should be understood that the accompanying drawings are provided for illustration purposes only, but not intended to limit the embodiments of the specification. Additionally, certain elements to which various modifications such as exaggeration and omission are applied may be shown in the accompanying drawings for clarity of description.

FIGS. 13A to 13K are schematic conceptual diagrams showing a process of manufacturing a skin sensor, according to a fourth embodiment of the present disclosure.

DETAILED DESCRIPTION

Figure 1A:
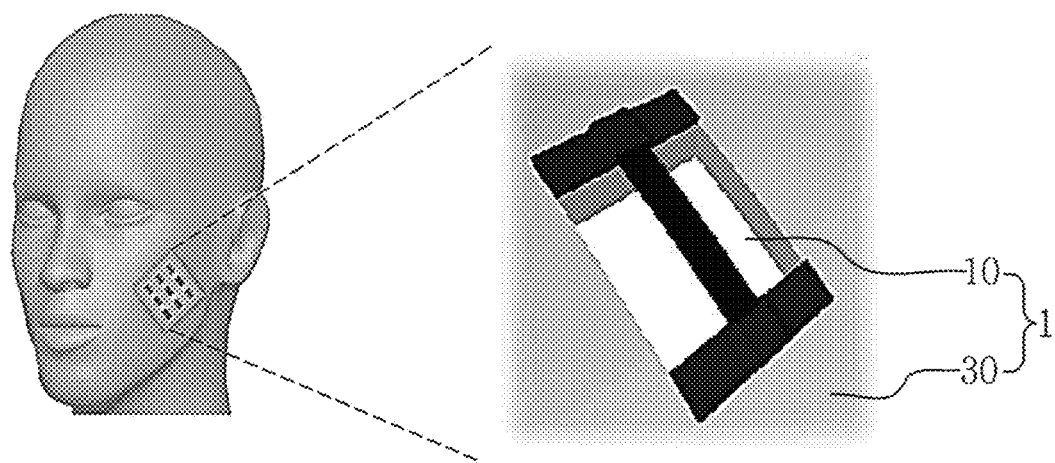
FIGS. 1A to 1C are schematic diagrams showing an electronic device adhered to a subject's skin, according to embodiments of the present disclosure.

Hereinafter, the embodiments of the present disclosure will be described in detail with reference to the accompanying drawings.

It will be understood that, if an element is referred to as being "directly above" another element, it can be directly above the other element or intervening elements may be present. In contrast, if an element is referred to as being "directly above" another element, there are no intervening elements present.

The terms "first", "second", and the like are used to describe various parts, components, areas, layers and/or sections, but are not limited thereto. These terms are only used to distinguish one part, component, area, layer or section from another. Accordingly, a first part, component, region, layer or section stated below may be referred to as a second part, component, region, layer or section without departing from the scope of the present disclosure.

The terminology used herein is for the purpose of describing particular embodiments only and is not intended to be limiting of the present disclosure. As used herein, the singular forms are intended to include the plural forms as well, unless the context clearly indicates otherwise. It will be further understood that the terms "comprising" and "including" when used in this specification, specify the presence of stated features, regions, integers, steps, operations, elements, and/or components, but do not preclude the presence or addition of one or more other features, regions, integers, steps, operations, elements, and/or components.

Spatially relative terms (e.g., "beneath", "below", "above" and the like) may be used herein for ease of description in describing a relationship between one element and another as illustrated in the figures. It will be understood that these terms are intended to encompass the intended meaning in the figures as well as different meanings or operations of the device in use. For example, if the device in the figures is turned over, elements described as "below" or "beneath" other elements would then be oriented "above" the other elements. Thus, the term "below" can encompass both an orientation that is above, as well as, below. The device may rotate 90° or at any other angle and the spatially relative terms should be interpreted accordingly.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the specification, a skin-adherable electronic device includes a substrate that can adhere to skin; and a semiconductor circuit unit that is integrated onto the substrate. The semiconductor circuit unit includes a semiconductor device including an active layer and an insulating layer, an electrode and/or a circuit connecting element such as an interconnector, and operates as a circuit that performs the function of the electronic device. The electronic device may be configured to operate itself or by electrical connection to an external device. In an embodiment, the skin-adherable electronic device may be a skin sensor that can acquire information of skin to which the skin-adherable electronic device adheres. However, the description related to the skin-adherable electronic device of the present disclosure is not limited to a skin sensor. By the embodiments of the present disclosure, electronic devices (e.g., light emitters) that operate with functions other than sensors may be manufactured.

Hereinafter, the embodiments of the present disclosure will be described in more detail with reference to the drawings.

Figure 1B:
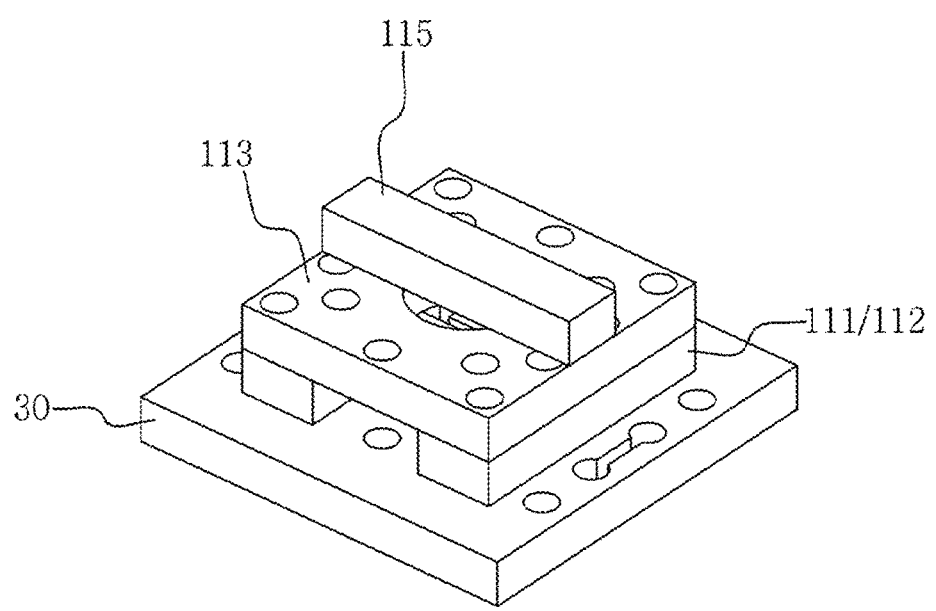
Figure 1C:
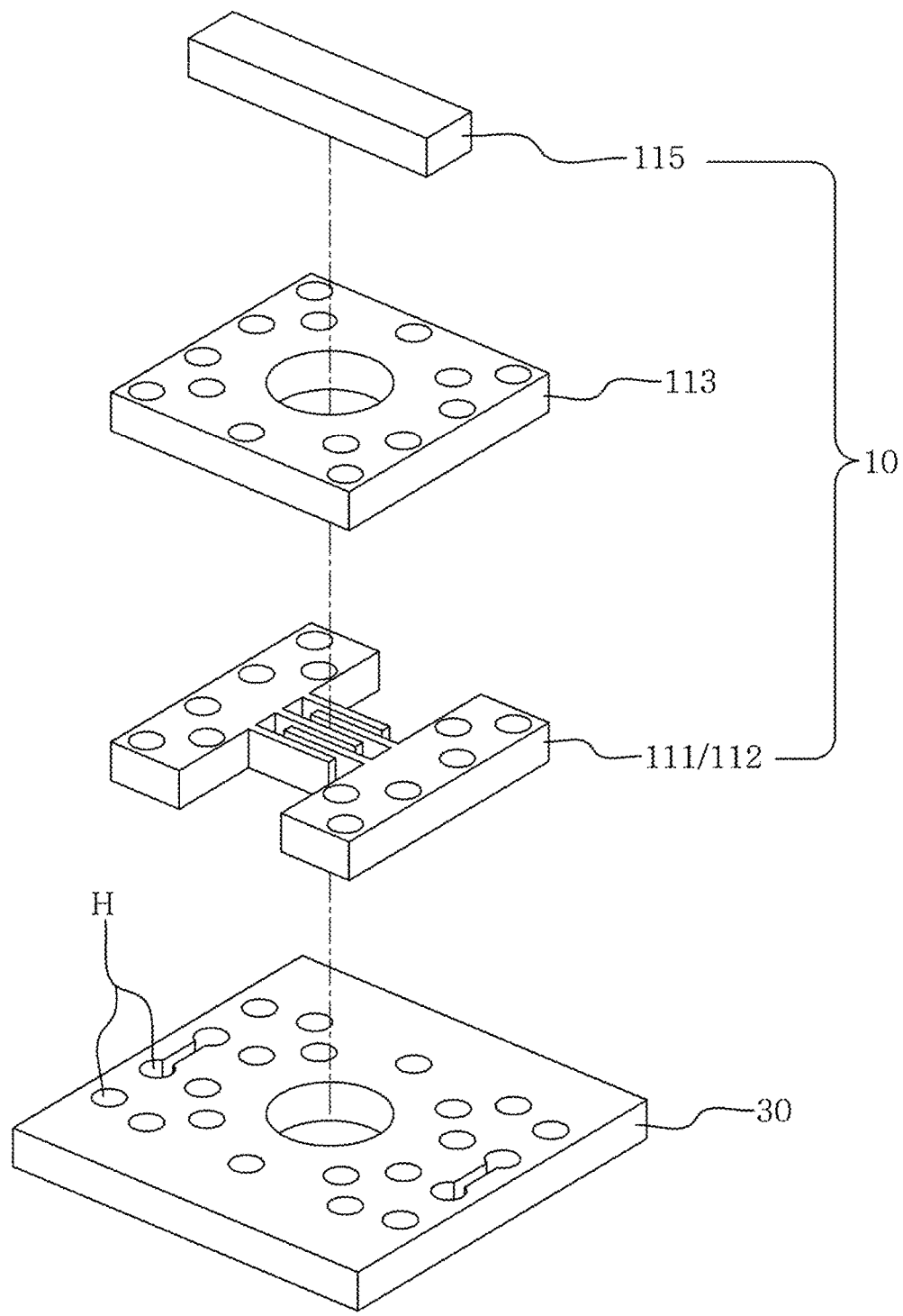

FIGS. 1A to 1C are schematic diagrams showing an electronic device adhered to a subject's skin, according to embodiments of the present disclosure.

Referring to FIG. 1A, the electronic device 1 according to the embodiments of the present disclosure may adhere to the subject's skin.

In an embodiment, the electronic device 1 includes a semiconductor circuit unit 10 that operates to perform the function of a sensor, and a flexible patch 30 that can adhere to skin, as a substrate onto which the semiconductor circuit unit 10 is integrated.

The semiconductor circuit unit 10 includes a semiconductor device including a semiconductor material, and a circuit element such as an electrode and/or an interconnecting element (for example, interconnect, etc.).

The function of the semiconductor circuit unit 10 relies on the semiconductor device and/or the circuit element. In an embodiment, when an active layer of the semiconductor circuit unit 10 is made of a piezoelectric material, the semiconductor circuit unit 10 operates as an piezoelectric element circuit that changes in the characteristics of the current with the changes in shape of the active layer, and the electronic device 1 including the semiconductor circuit unit 10 may operate as a skin deformation sensor to acquire skin deformation information, and further elasticity information. As described above, when the electronic device 1 includes an element made of a piezoelectric material, the semiconductor circuit unit 10 operates as a change sensing structure. This will be described in more detail with reference to FIGS. 2 and 3 below.

Alternatively, when the semiconductor circuit unit 10 includes a material that responds to light changes, the electronic device 1 may operate as an optical skin sensor or a skin image sensor.

Alternatively, when the semiconductor circuit unit 10 includes a material that responds to moisture changes, the electronic device 1 may operate as a skin moisture sensor.

Alternatively, when the semiconductor circuit unit 10 includes a light emitting material, the electronic device 1 may operate as a light emitting skin massager.

Hereinafter, for clarity of description, the present disclosure is exemplarily described, taking a sensor circuit unit including a piezoelectric material to sense skin deformation as an example of the semiconductor circuit unit 10 (hereinafter, the semiconductor circuit unit 10 is often referred to as a sensor unit circuit 10), and a skin sensor including the sensor unit circuit 10 as an example of the electronic device 1 (hereinafter, the electronic device 1 is often referred to as a skin sensor 1).

According to the embodiments of the present disclosure, the skin-adherable skin sensor 1 may be manufactured. The skin sensor 1 may adhere to skin to acquire information associated with skin.

The skin sensor 1 according to an embodiment includes a flexible patch 30 having a plurality of air permeable through-holes H, and a sensor circuit unit 10 bonded to the flexible patch 30.

The flexible patch 30 is a substrate onto which the semiconductor circuit unit 10 is integrated, and is configured such that at least one surface has sufficient viscosity to adhere to skin. Additionally, the flexible patch 30 includes a plurality of through-holes with high air permeability and strong adhesiveness. This will be described in more detail with reference to FIGS. 2 and 3 below.

The skin sensor 1 is formed in a free-standing form on the air permeable through-holes H. In an embodiment, as shown in FIG. 1A, the skin sensor 1 is formed with a free-standing structure such that the active layer of the skin sensor unit 10 is disposed on the though-holes. Because the active layer of a piezoelectric material is suspended in a free-standing form on the through-holes for skin respiration, it is possible to efficiently measure changes of the through-holes with skin deformation. That is, the active layer of the skin sensor 1 may be effectively bent according to skin deformation induced by the mechanical strain.

The skin sensor 1 includes the sensor circuit unit 10 disposed on the flexible patch 30, and the sensor circuit unit 10 includes a circuit element (for example, an electrode 111 and/or an interconnect 112), an insulating layer 113 and an active layer 115.

In certain embodiments, as shown in FIGS. 1B and 1C, the sensor circuit unit 10 includes the circuit element (for example, the electrode 111 and/or the interconnect 112) disposed on the flexible patch 30, the insulating layer 113 disposed on the circuit element, and the active layer 115 disposed on the insulating layer 113. The elements 111, 112, 113, 115 disposed on the flexible patch 30 may have a through-hole corresponding to at least one of the though-holes of the flexible patch 30. Accordingly, the electronic device 1 can have strong adhesiveness, and ensure air permeability.

In other embodiments, the sensor circuit unit 10 includes the active layer 115 disposed on the flexible patch 30, the insulating layer 113 disposed on the active layer 115, and the circuit element disposed on the insulating layer 113. The operation principle of the skin sensor 1 will be described in more detail with reference to FIG. 2 below.

The skin sensor 1 may include at least one semiconductor circuit unit 10. The semiconductor circuit unit 10 may be configured to perform the same function or different individual functions.

The skin sensor 1 is configured to acquire various information (e.g., skin elasticity information, skin deformation information, etc.) associated with the subject's skin when the semiconductor circuit adheres to skin through the flexible patch, with minimizing the influence on the subject's skin while it is adhered to skin even for a long term.

Figure 2A:
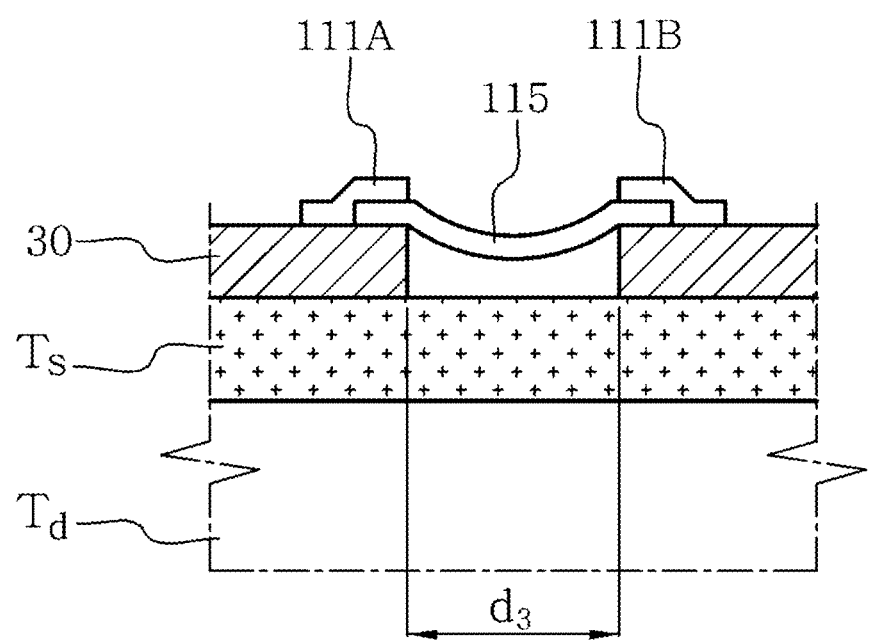
FIGS. 2A to 2C ares a diagram illustrating an operation principle of a skin sensor 1, according to an embodiment of the present disclosure.
Figure 2B:
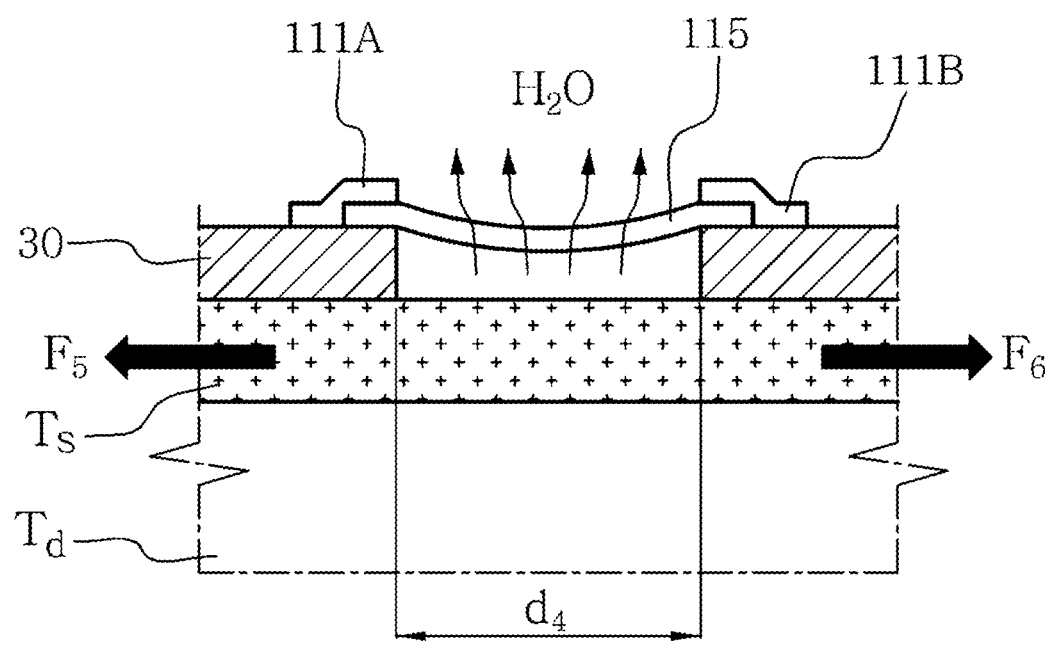
Figure 2C:
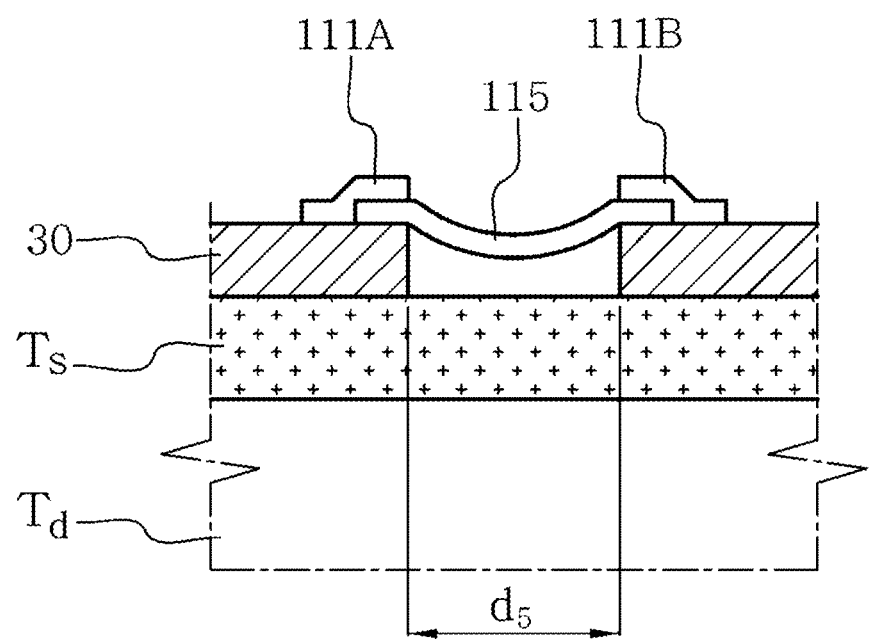

FIGS. 2A to 2C are a diagram illustrating the operation principle of the skin sensor 1, according to an embodiment of the present disclosure.

Referring to FIG. 2, the skin sensor 1 according to an embodiment of the present disclosure may detachably adhere to skin Ts, Td. The skin includes a corneous layer Ts and an epidermal layer Td. The skin sensor 1 adheres tightly to the surface of the corneous layer Ts. The mechanical changes of skin bring about changes of the through-holes H. Accordingly, it is possible to acquire information associated with the mechanical changes of skin by measuring the changes of the through-holes H.

The mechanical changes of skin may be analyzed based on the mechanism of the skin layer. The skin includes a corneous layer to approximately 20 μm, and a dermal layer and an epidermal layer to approximately 2 mm. Accordingly, when the epidermal layer is regarded as a substrate, the corneous layer has a thin film structure at a ratio of approximately 1/100 relative to the epidermal layer. Accordingly, when skin gets dry, volume contraction is induced in the corneous layer which is a thinner film.

Additionally, when dry skin occurs, at the early stage, the moisture in the corneous layer reduces and contraction occurs, but the epidermal layer becomes less dry, so the epidermal layer pulls the corneous layer, resulting in the tensile strain. However, when continuous dry skin occurs, the elastic modulus of the corneous layer increases, and cracks occur in the corneous layer Ts, leading to a loss of protection function. Additionally, when cracks occur, the tensile strain reduces, and the skin sags.

The skin sensor 1 adheres to the through-hole H in a free-standing form to sense skin changes by sensing changes in the pressure applied on the change sensing structure with the size changes of the through-hole H adhered to the skin.

In the specification, a skin change ratio may be defined as the following [Equation 1] using the initial length L0 of skin in a preset region and the length Lt after the time t:

$$\text{Change}(\%) = \text{length change}(Lt-L0)/\text{initial length}(L0) \times 100 \quad \text{[Equation 1]}$$

That is, the skin change ratio may be provided as a quantitative value by calculating the length change of the change sensing structure (i.e., the active layer 115).

The situation of FIG. 2A represents the case in which there is no skin change and no pressure applied. In the situation of FIG. 2A, the through-hole may have a length d3.

The situation of FIG. 2B represents a case in which the materials including moisture are released from skin over time. In the situation of FIG. 2B, when the corneous layer gets dry first by the release of the materials including moisture from skin over time, the tensile strain F5, F6 occurs in the corneous layer. Accordingly, the through-hole increases in size, and the tensile strain is applied to the active layer 115 region disposed on the through-hole. The through-hole may have a length d4. d4 is longer than d3. As the through-hole changes, the active layer 115 region disposed on the through-hole changes, causing changes in electric current. Additionally, in this case, it may be determined that the subject's skin feels tight.

The situation of FIG. 2C shows that continuous dry skin occurs. When continuous dry skin occurs, cracks C occur in the corneous layer and the size of the through-hole reduces compared to the situation of FIG. 2B. Accordingly, the tensile strain applied to the active layer 115 region disposed on the through-hole reduces, and in this case, the through-hole may have a length d5. d5 is shorter than d4.

In this way, the skin change amount may be measured by the pressure applied to the active layer 115 region disposed on the through-hole.

Figure 3:
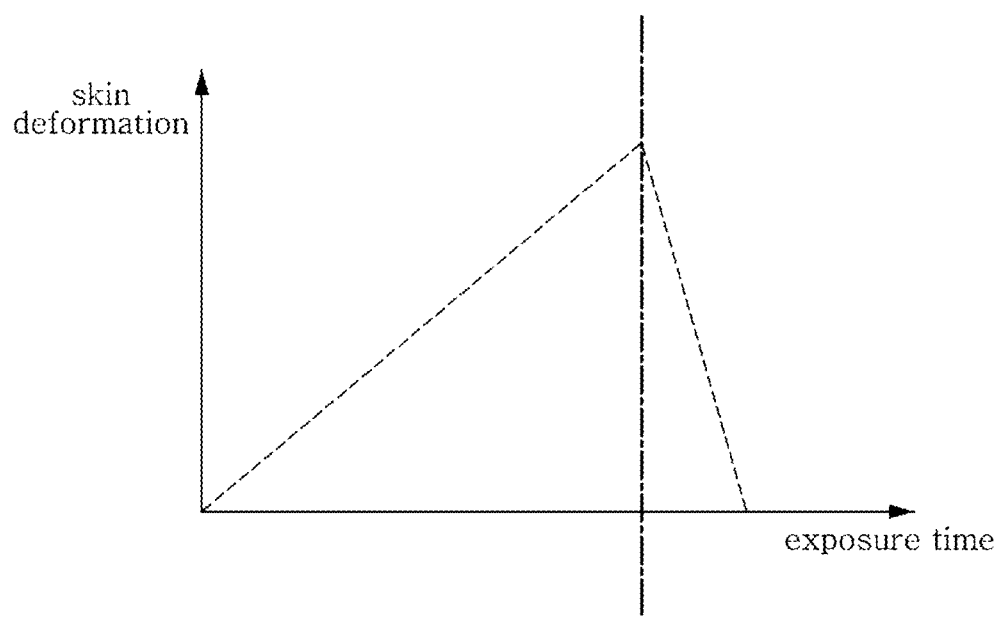
FIG. 3 is a graph showing a skin deformation ratio over time, measured by a skin sensor, according to an embodiment of the present disclosure.

FIG. 3 is a graph showing a skin deformation ratio over time, measured by the skin sensor, according to an embodiment of the present disclosure The situation of FIG. 2A corresponds to the exposure start time in the graph of FIG. 3. When the skin starts to get dry, in the situation of FIG. 2B, as the corneous layer becomes dry, the tensile strain increases and skin deformation continuously increases.

Then, in the situation of FIG. 2C in which the corneous layer is formed, as the corneous layer is cracked, the tensile strain reduces again, and deformation returns to the initial state or its similar state.

In the skin sensor 1 adhered to skin surface, the sensor circuit unit 10 operating as a sensor is disposed on the flexible patch 30. That is, the flexible patch 30 is used as a substrate onto which circuits are integrated. Dissimilar to commonly used circuit substrates, the flexible patch 30 is soft and sticky. Accordingly, it is difficult to manufacture the skin sensor 1 of the present disclosure simply by a process of integrating circuit elements on a substrate in a sequential order.

First Embodiment

Figure 4A:
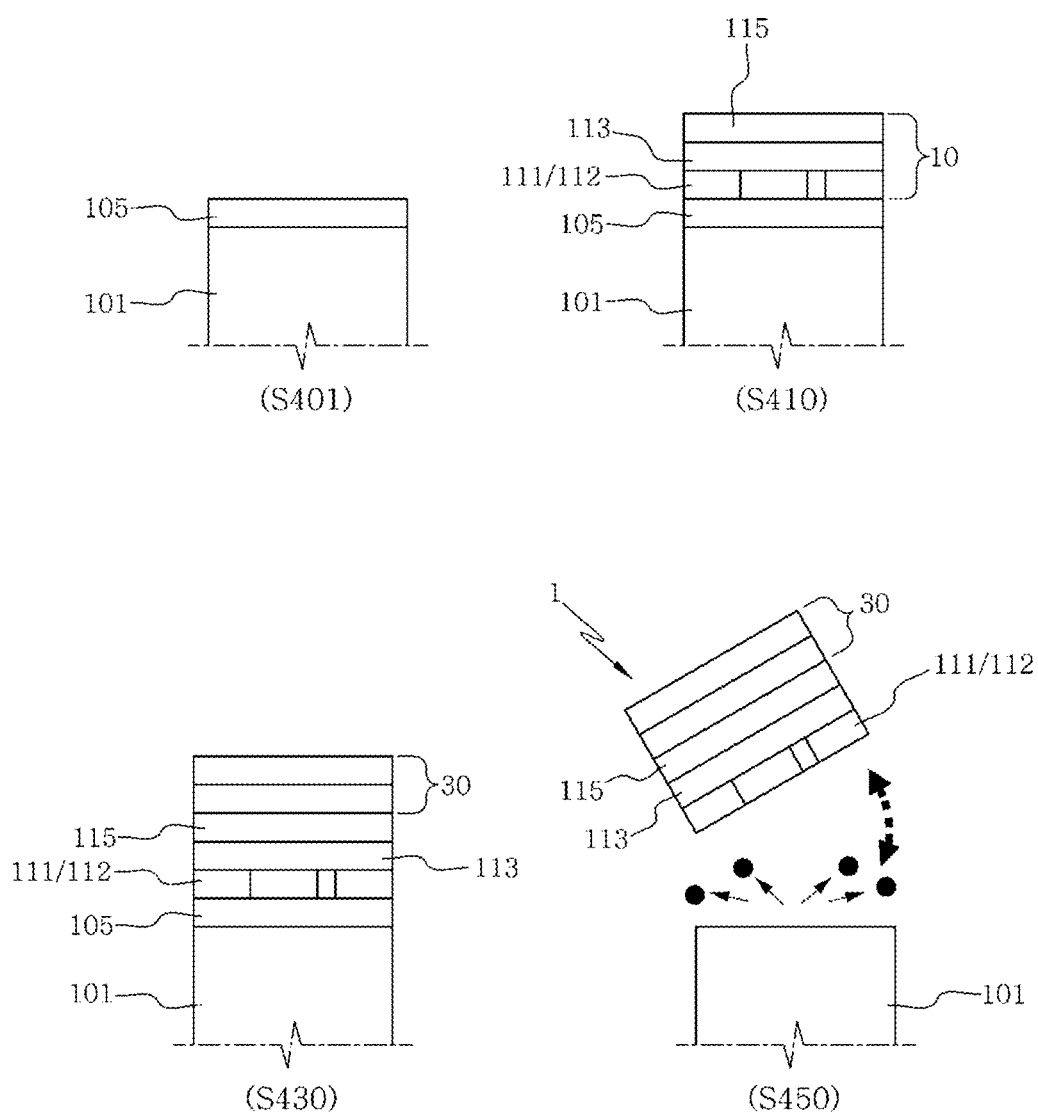
FIGS. 4A and 4B are schematic conceptual diagrams showing a process of manufacturing a skin sensor, according to a first embodiment of the present disclosure.
Figure 4B:
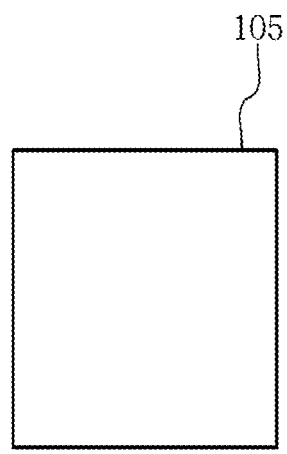
Figure 4B:
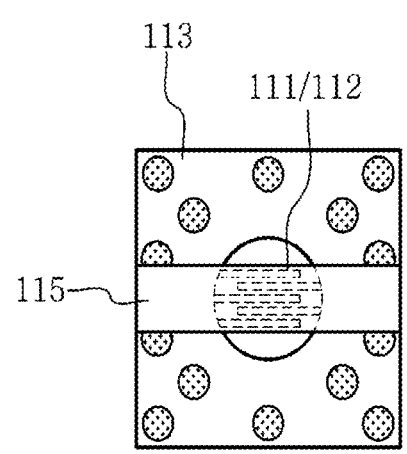
Figure 4B:
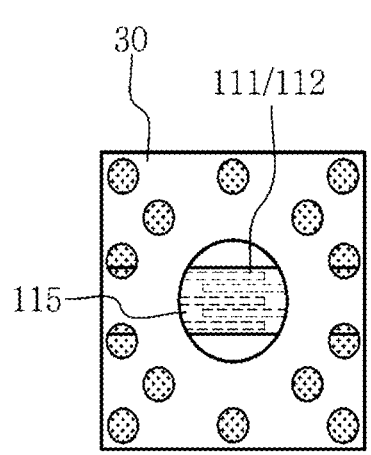
Figure 4B:
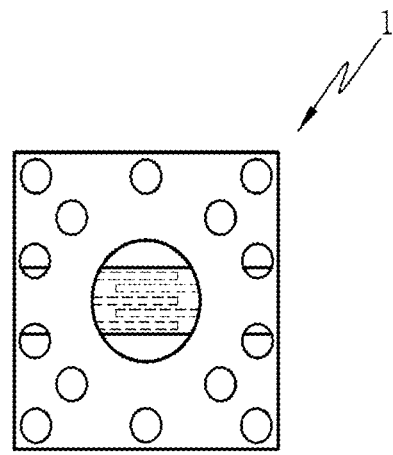

FIGS. 4A and 4B are schematic conceptual diagrams showing the process of manufacturing the skin sensor, according to a first embodiment of the present disclosure.

Referring to FIGS. 4A and 4B, the method of manufacturing the skin sensor 1 according to the first embodiment of the present disclosure includes forming a sacrificial layer 105 on a substrate 101 (S401); forming a sensor circuit unit 10 on the sacrificial layer 105 (410), including forming an electrode 111 and/or an interconnect 112 (S411); forming an insulating layer 113 on the electrode and/or the interconnect (S413); and forming an active layer 115 on the insulating layer 113 (S415); bonding the sensor circuit unit 10 (i.e., the active layer 115) and the flexible patch 30 (S430); and etching the sacrificial layer 105 to manufacture the skin sensor 1 (S450).

The substrate 101 (or referred to as a first substrate) is used to stack the inner layers of the sensor circuit unit 10. That is, the substrate 101 is a substrate used to form the elements of the sensor circuit unit 10 such as the electrode 111 and/or the interconnect 112 and the active layer 115. In an example, the substrate 101 may be made of silicon (Si), and the sacrificial layer 105 may be formed on the substrate 101 (S401).

Meanwhile, the sacrificial layer 105 is made of a material (e.g., metal) that is resistant to organic solvents, and allows photo-lithography. In an embodiment, the sacrificial layer 105 may be made of a material including at least one of Cr, Al, Ni, Au and their combinations.

Additionally, the sacrificial layer 105 may be formed further based on a material property (e.g., standard oxidation potential) associated with adhesiveness and/or another material property (e.g., melting temperature) associated with thermal stability. In this case, the sacrificial layer 105 may have strong adhesiveness and thermal stability enough to withstand various strains. In certain embodiments, the sacrificial layer 105 may be made of a material including Cr, Al, Ni and their combinations.

The semiconductor structure that operates as the sensor circuit unit 10 is formed on the sacrificial layer 105.

Figure 5A:
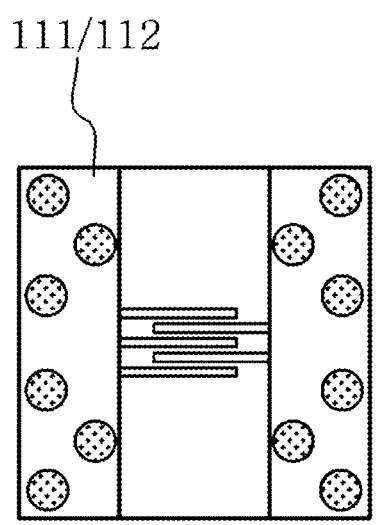
FIGS. 5A to 5C are cross-sectional views showing the preparation of a semiconductor structure having an active layer in a process of manufacturing a skin sensor 1, according to a first embodiment of the present disclosure.
Figure 5A:
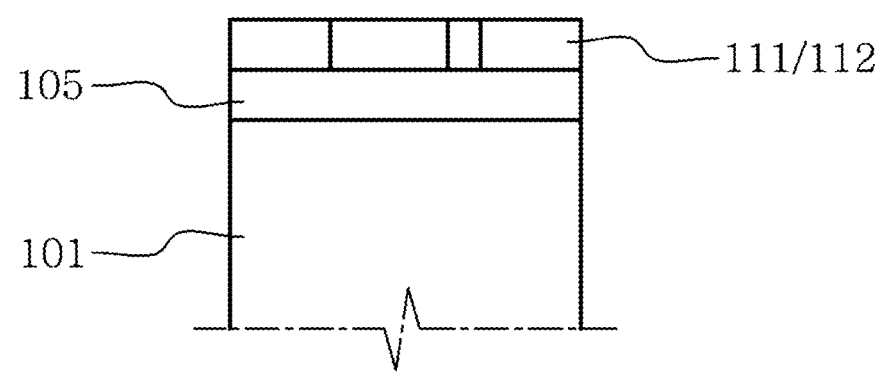
Figure 5B:
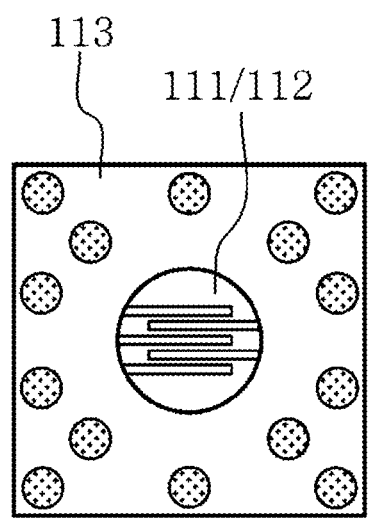
Figure 5B:
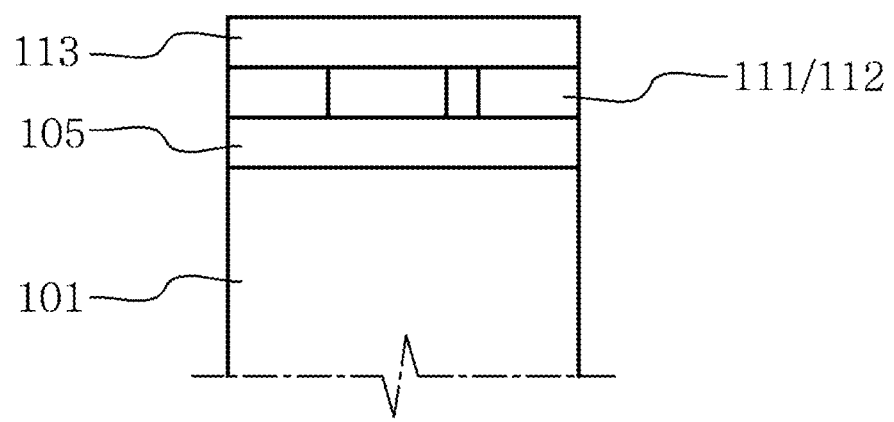
Figure 5C:
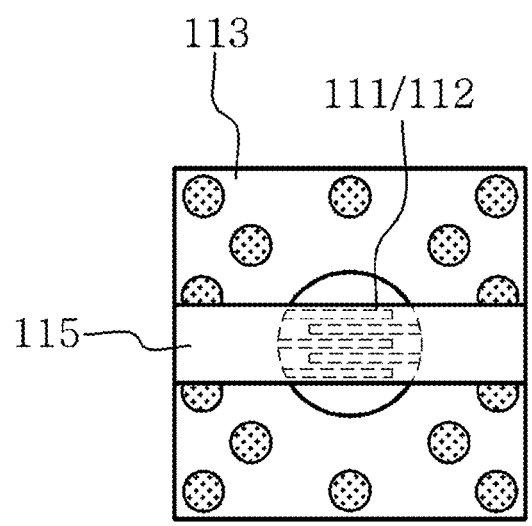
Figure 5C:
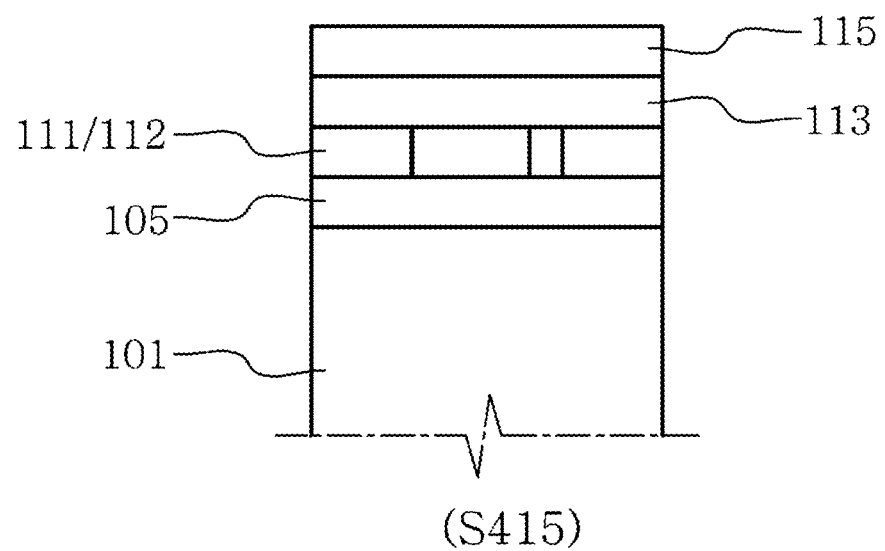

FIGS. 5A to 5C are cross-sectional views showing the preparation of the semiconductor structure having the active layer in the process of manufacturing the skin sensor 1, according to the first embodiment of the present disclosure.

Referring to FIG. 5A, a conducting layer including the electrode 111 and/or the interconnect 112 is formed on the sacrificial layer 105 (S411). The electrode 111 and/or the interconnect 112 are circuit elements made of a conductive material (such as, for example, gold (Au), platinum (Pt)), and operates as the skin sensor 1 by transmitting current changes based on the active layer that acts as a piezoelectric element.

The skin sensor 1 is configured to deform along the skin surface, and have strong durability even if the skin sensor 1 deforms so much in the process of attaching and detaching. Accordingly, the electrode 111 and/or the interconnect 112 is formed to have a structure that is resistant to deformation.

FIGS. 6A to 6E are diagrams illustrating the electrode and/or interconnect structure configured to have an auxetic property, according to an embodiment of the present disclosure.

In an embodiment, the electrode 111 and/or the interconnect 112 are formed on the sacrificial layer 105 with a plane structure that can implement an auxetic property (S411).

In general, an auxetic structure refers to a structure that, when it is placed under tension in a first direction, increases in its dimensions in a direction that is orthogonal to the first direction. For example, if the auxetic structure can be described as having a length, a width and a thickness, then when the auxetic structure is under tension longitudinally, it increases in width. Additionally, the auxetic structure is bi-directional such that it increases in length and width when stretched longitudinally, and increases in width and length when stretched laterally, but does not increase in thickness. This auxetic structure characterized by having a negative Poisson's ratio.

Figure 6A:
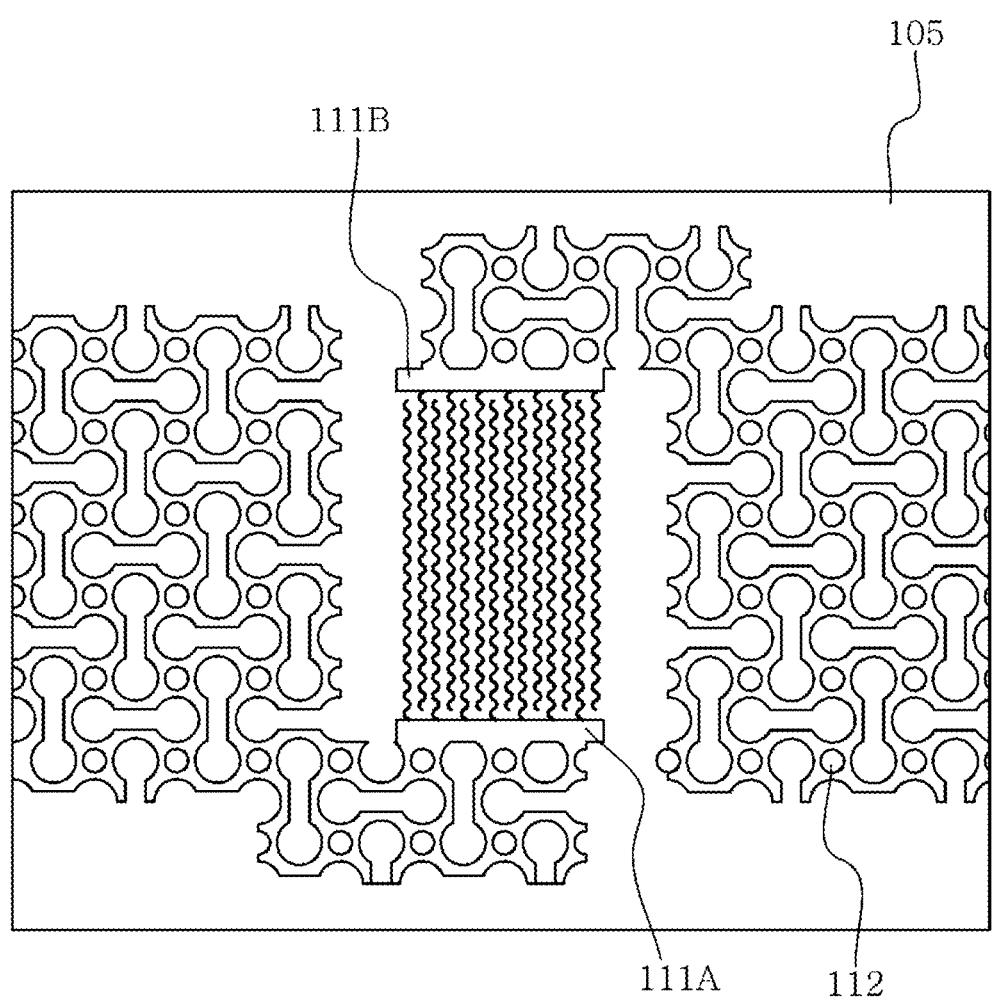
FIGS. 6A to 6E are diagrams illustrating an electrode and/or interconnect structure configured to have an auxetic property, according to an embodiment of the present disclosure.

In S411, a first electrode 111A and a second electrode 111B are formed on the sacrificial layer 105. Referring to FIG. 6A, the first electrode and the second electrode 111A and 111B include at least one bar. The bar included in the first electrode 111A has the plane of a zigzag shape, and extends to the second electrode 111B on the opposing side. The bar included in the second electrode 111B also has the plane of a zigzag shape, and extends to the first electrode 111A on the opposing side. Because of including the zigzag shaped bar, each electrode 111A and 111B can have a property (i.e., an auxetic structure property) resulting from the auxetic structure.

Figure 6B:
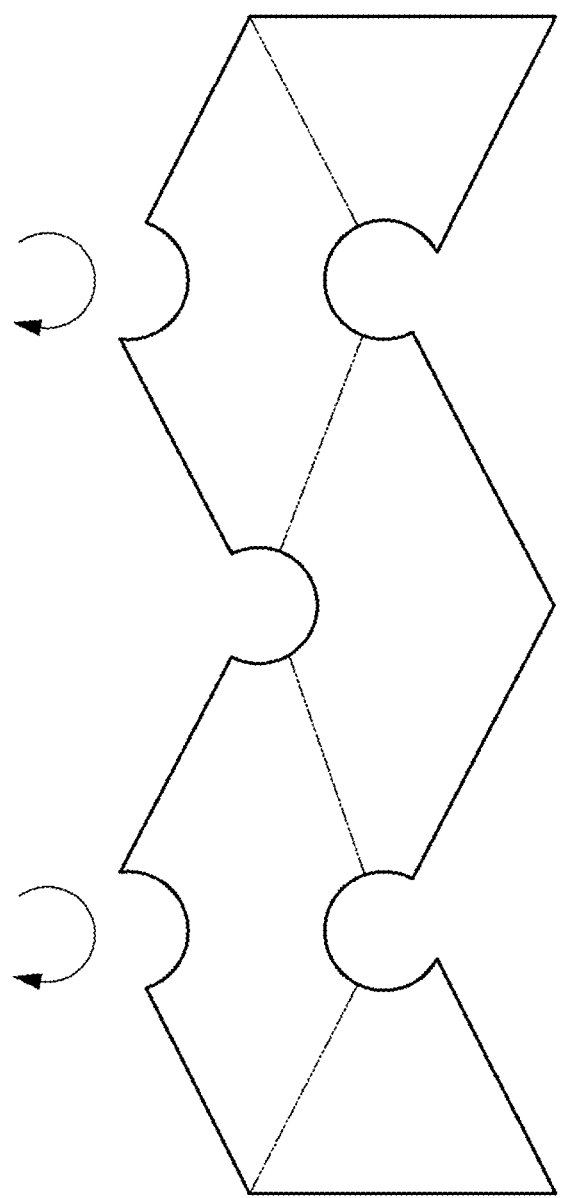

Referring to FIG. 6B, in an embodiment, the bar may have a circular cut hinge pattern at a point where the extension direction of the bar changes. The hinge pattern may prevent crack propaganda.

Figure 6C:
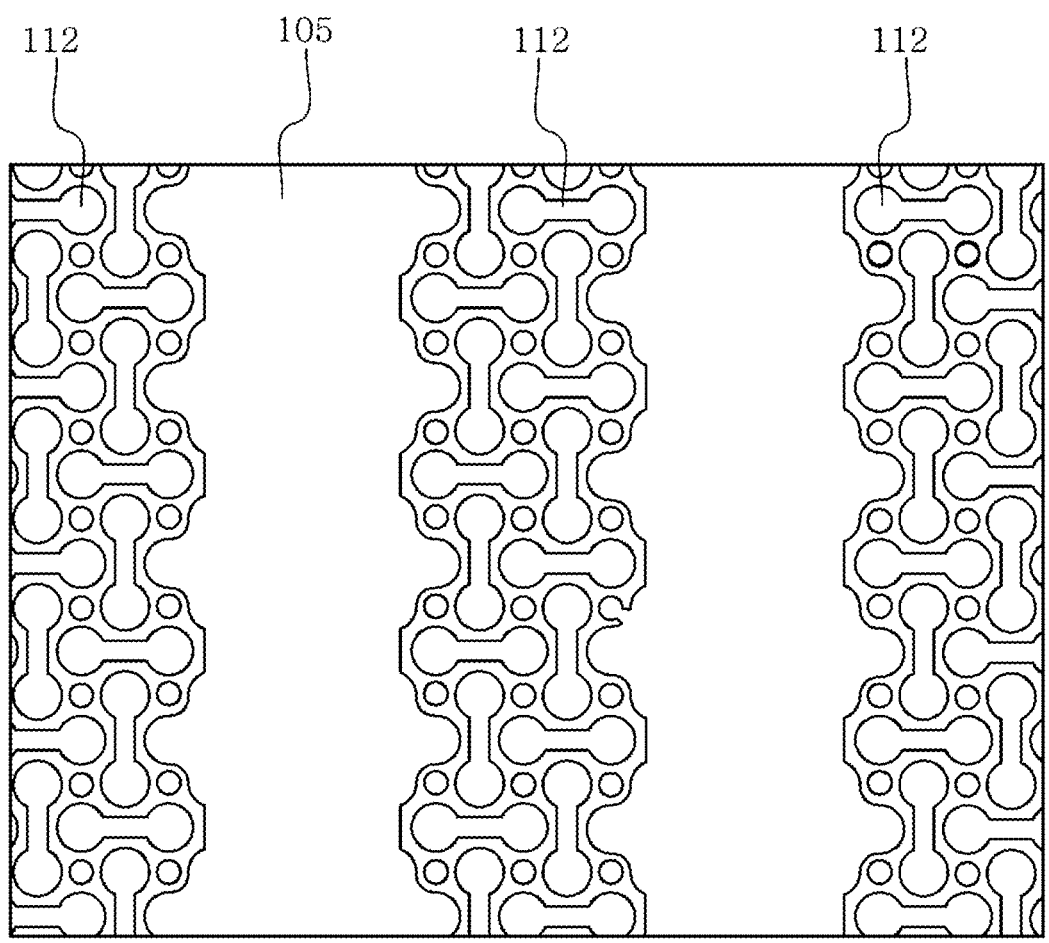

As shown in FIG. 6C, the interconnect 112 is configured to form dumbbell-shaped holes including circles at two ends and a middle connecting the circles at two ends in the form of a pillar with a smaller thickness than the diameter of the two ends. Additionally, the interconnect 112 is configured to form circular holes (dumbbell-hole pattern). The interconnect 112 having the through-holes may have a property (i.e., an auxetic structure property) resulting from the auxetic structure.

Figure 6D:
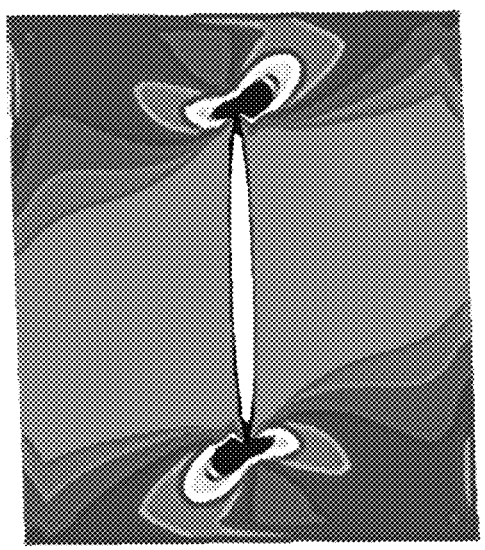
Figure 6D:
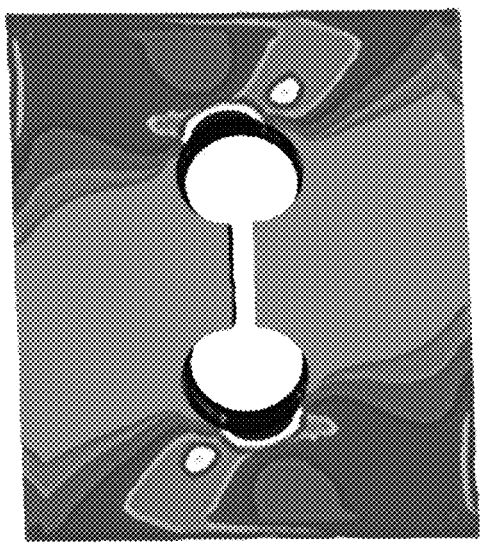

Even though the shape of the interconnect 112 is deformed by an external force acting on the interconnect 112, cracking at the two ends is minimized by the auxetic structure property. Referring to FIG. 6D, it can be seen that when a region in which cracks occur has dumbbell through-holes, less cracking occurs.

Figure 6E:
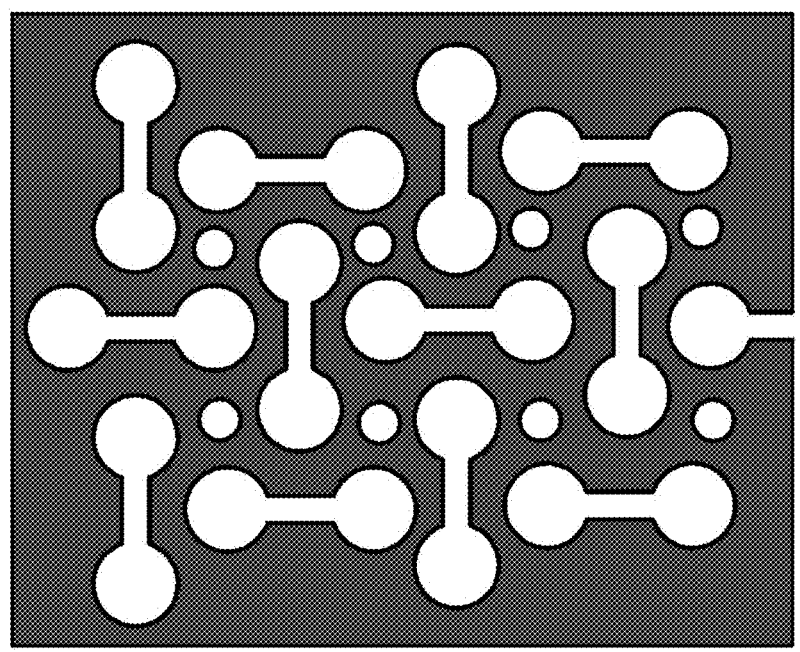

The electrode 111 and/or the interconnect 112 having the auxetic structure property may be formed on the sacrificial layer 105 by various methods. In an example, after the conducting layer is formed, the electrode 111 and/or the interconnect 112 may be formed by a photo-lithography based etching process using a mask configured to form an auxetic structure (for example, as shown in FIG. 6E). In the mask of FIG. 6E, a conducting layer region corresponding to the dark section is formed as interconnect, and a conducting layer region corresponding to the bright section is formed as through-hole.

Referring to FIG. 5B, after the electrode 111 and/or the interconnect 112 are formed, the insulating layer 113 is formed (S413). The insulating layer 113 may be an oxide layer ($SiO_2$) formed on the surface of the silicon (Si) substrate 110. However, this is for illustration purposes only, and the insulating layer 113 may be made of oxide materials other than silicon oxide.

In an embodiment, the insulating layer 113 may include a plurality of through-holes to ensure air permeability. The through-holes of the insulating layer 113 match the through-holes of the flexible patch 30 not to obstruct a flow of air moving through the through-holes of the flexible patch 30. Accordingly, air permeability of the skin sensor 1 is maximized. In certain embodiments, the through-holes of the insulating layer 113 may be formed by a photo-lithography based etching process.

Referring to FIG. 5C, the active layer 115 may be formed on the insulating layer 113 (S415). The active layer 115 and the process of forming the active layer 115 will be described in more detail with reference to FIG. 7 below.

Figure 7:
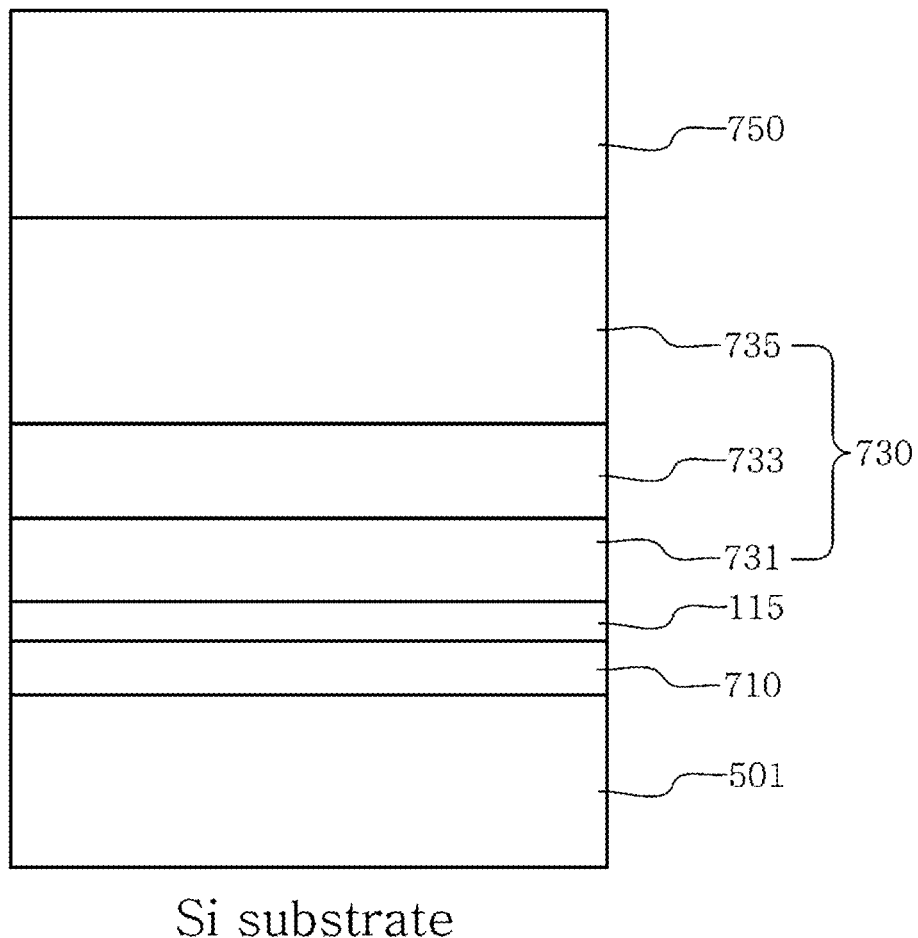
FIG. 7 is a diagram illustrating a transfer structure, according to an embodiment of the present disclosure.

FIG. 7 is a diagram illustrating a transfer structure, according to an embodiment of the present disclosure. In an embodiment, the active layer 115 may be formed on the insulating layer 113 by transfer using the transfer structure (S415).

Referring to FIG. 7, the transfer structure is a structure formed on a substrate 701, and includes a metal layer 710 formed on the substrate 701; an active layer 115 formed on the metal layer 710; a stressor layer 730 formed on the active layer 115; and a tape layer 750 disposed on the stressor layer 730.

The substrate 701 (or referred to as a second substrate) is a substrate used to form the transfer structure, and is a substrate that is different from the substrate 101. An active layer 115 is formed on the substrate 701. In an example, the substrate 701 may be made of a material including silicon (Si).

In an embodiment, the active layer 115 may be formed on the metal layer 710 formed on the substrate 701. The metal layer 710 is configured to have a weak adhesive strength to allow the active layer 115 to be transferred more easily. In an example, the metal layer 710 may be made of a material including gold (Au).

The active layer 115 is a layer made of a material having semiconductor properties, and performs the main function of the skin-adherable electronic device 1. When the skin-adherable electronic device 1 is used as a skin sensor, in an embodiment, the active layer 115 may be made of a material including Ga and Al, which has a good electron transport characteristic and can be used as a piezoelectric material. For example, the active layer 115 may be made of a material including AlN or GaN.

The stressor layer 730 enhances the semiconductor properties by modifying the material of the active layer 115. For example, the piezoelectric performance may be enhanced by the stressor layer 730. Additionally, the stressor layer 730 is configured to minimize cracking in the process of transferring the active layer 115 onto the insulating layer 113. To this end, the stressor layer 730 may be formed as a multilayer structure including a plurality of layers having various materials and various thicknesses.

In an embodiment, the stressor layer 730 includes three layers 731 to 735. The first stressor layer 731 may be a high-strain metal layer made of a material (e.g., Ni or AgNi) including Ni. The second stressor layer 733 may be made of a material including Al. The third stressor layer 735 may be made of a material including Ag.

The thickness of the first stressor layer 731 may be different for each material. For example, when the first stressor layer 731 is made of Ni, the thickness of the first stressor layer 731 may be 50 nm. Meanwhile, when the first stressor layer 731 is made of AgNi, the thickness of the first stressor layer 731 may be 70 nm.

Each stressor layer may be formed by the same or different methods. In an example, the first stressor layer 731 formed on the active layer 115 may be formed by evaporation. The second stressor layer 733 formed on the first stressor layer 731 and the third stressor layer 735 formed on the second stressor layer may be formed by sputtering deposition. Each stressor layer may differ in formation rate. In an example, the second stressor layer 733 may be formed at 1.8 Ås$^{-1}$, and the third stressor layer 735 may be formed at 2 Å s$^{-1}$. In another example, the second stressor layer 733 may be formed at 0.4 Å s$^{-1}$, and the third stressor layer 735 may be formed at 2 Å s$^{-1}$.

The transfer structure of FIG. 7 is peeled off from the substrate 701 by the tape layer 750, and the peeled active layer 115 is transferred onto the insulating layer 113. Subsequently, the tape layer 750 and the stressor layer 730 are removed to form a stack including the conducting layer including the substrate 101, the sacrificial layer 105, the electrode 111 and/or the interconnect 112; the insulating layer 113 and the active layer 115.

In an embodiment, the transfer of the active layer 115 using the transfer structure of FIG. 5 may be performed within the range of approximately 165° C. In this case, the tape residue on the active layer 115 is minimized.

As described above, the active layer 115 made of high performance, monocrystalline piezoelectric semiconductor materials (AlN, GaN) may be transferred onto the insulating layer 113 using 2-Dimension material based Layer Transfer (2DLT).

Referring back to FIG. 4, the flexible patch 30, or an element that adheres to skin, is disposed on the active layer 115 of semiconductor structure, and the disposed flexible patch 30 is bonded to the active layer 115 (S430).

Figure 8:
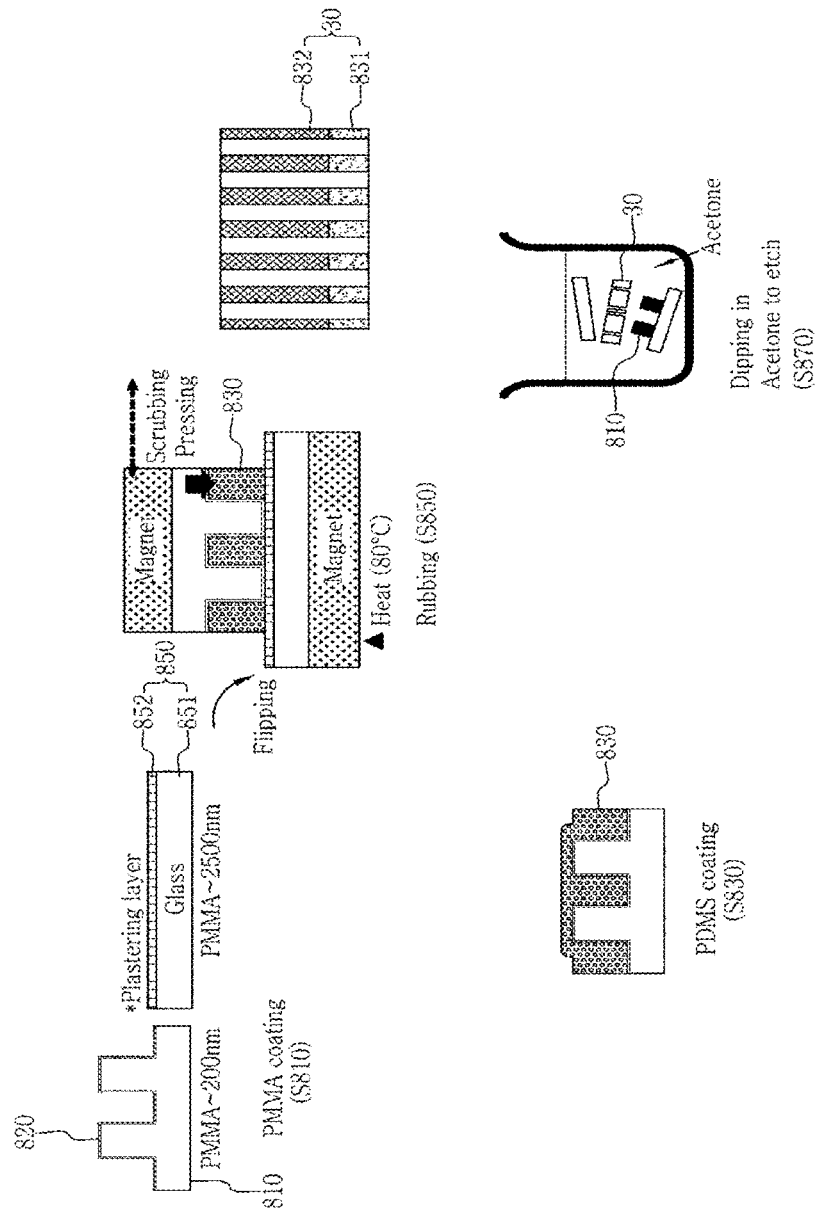
FIG. 8 is a schematic diagram showing a process of manufacturing a flexible patch 30, according to an embodiment of the present disclosure.

FIG. 8 is a schematic diagram showing the process of manufacturing the flexible patch 30, according to an embodiment of the present disclosure.

Referring to FIG. 8, the method of manufacturing the flexible patch 30 includes forming a sacrificial layer on a mold having a plurality of concave furrows on one surface (S810), and forming a flexible patch layer on the sacrificial layer (S830).

For a rigid material, as shown in FIGS. 1A and 1B, a wet/dry etching method is used to form a geometric plane structure such as a micro-hole patterned surface. However, when a flexible material (e.g., PDMS, etc.) that is relatively soft is used to form a geometric plane structure using a dry/wet etching method, the geometric plane structure such as holes is out of shape. However, when a mold 810 having a plurality of concave furrows is used to form a plurality of holes on one surface of the flexible material, it is possible to obtain a flexible patch layer 830 having the holes that are not put out of shape The mold 810 has the plurality of furrows formed on one surface, and thus has the geometric plane. The cross section of the furrows that form the geometric plane of the mold 810 is concave inward one surface as shown in FIG. 8. When any flowable material (e.g., including the flexible material used to form the flexible patch layer 830) is formed on the mold 810, the material fills the furrows. When the material is cured, a height structure corresponding to the filled furrows is formed in the furrows. The furrows may have a single step or one or more steps.

The flexible patch layer 830 includes a material layer that has a sufficient adhesive property to adhere to skin. Accordingly, when the flexible patch layer 830 is formed immediately on the mold 810, it is difficult to separate the flexible patch layer 830 from the mold 810, and when damage occurs in the flexible patch layer 830 in this process, there is a risk that the quality of the flexible patch 30 may be degraded. To overcome this problem, before filling the furrows of the mold 810 with the flexible material, a sacrificial layer 820 having an anti-sticky layer function to prevent the adhesion between the flexible patch layer 830 and the mold 810 is formed between the mold 810 and the flexible patch layer 830 (S810). With the sacrificial layer 820, the flexible patch layer 830 can be separated from the mold 810 without damage, obtaining the flexible patch 30 with high quality.

The mold 810 is configured such that it is not etched by an etching solution, even when a predetermined heat is applied, it can maintain the shape, and it has a predetermined rigidity. Additionally, the mold 810 is made of a non-magnetic material. In an example, the mold 810 may be made of a material including silicon (Si), but is not limited thereto, and may be made of various materials that are not removed by a material that removes the underlying sacrificial layer 820, can maintain the shape even at a particular temperature or above, and is not difficult to manufacture the mold.

FIGS. 9A to 9D are diagrams illustrating a structure of the mold and a plurality of through-holes of the flexible patch formed by the mold.

The mold 810 has the furrow shape and distribution to allow hole generation for the improved properties of the flexible patch 10 such as air permeability and adhesiveness.

In an embodiment, the plurality of furrows formed on the surface of the mold 810 may be configured to form a circular hole pattern. For example, the mold 810 having a plurality of furrows of circular border may be used to form the plurality of holes in the flexible patch 30. Using the mold 810 of FIG. 9A, the flexible patch 30 including through-holes having the plane of FIG. 9B may be obtained.

In an embodiment, the plurality of furrows formed in the mold 810 may be distributed such that the spacing between the holes of the flexible patch 30 is less than 60 μm. The sweat pores have various sizes depending on the position on the skin. For example, it is known that the area of the sweat pores has the diameter of 60 μm or more, and has the diameter of 80 μm on average. Additionally, biological functions performed by sweat such as adjustment of the quantity of waste to excrete and the temperature are different depending on the position on the skin, and the distribution density differs in each body part. For example, the sweat pores are distributed at the density of 60 $cm^{-2}$ on the back, 400 $cm^{-2}$ on the palm, and 180 $cm^{-2}$ on the forehead.

Based on the information associated with the size and area of sweat pores, the spacing between the holes of the flexible patch 30 should be less than 60 μm. When the spacing between the holes is equal to or larger than 60 μm, the surface of the flexible patch 30 other than the holes may block the sweat pores. Accordingly, the flexible patch 30 having the spacing between the holes of less than 60 μm may have higher air permeability (e.g., nearly 100% air permeability). In certain embodiments, the flexible patch 30 may be manufactured using the mold 810 which makes a through-hole pattern having the spacing between the holes of 50 μm.

The main factor for obtaining high air permeability is the spacing between the through-holes. The size of the through-hole affects both adhesiveness and air permeability. It is because as the size of the through-hole is larger, the skin area that contacts air increases, but on the contrary, the volume of skin held reduces. The embodiments of the present disclosure can obtain high air permeability and strong adhesiveness by reducing the spacing between the through-holes even though the size of the through-hole is small. The size of the through-hole may be variously set within the range in which adhesiveness is not hindered.

In addition, the size of the hole may be variously set based on the design of the semiconductor circuit that will be disposed on the flexible patch 30.

For example, when parts of a piezoelectric device are disposed on the through-holes on the flexible patch 30 and the circuit elements are disposed to measure and transmit changes in electric current with the deformation of the piezoelectric device, it may be set such that parts of the piezoelectric device where deformation usually occurs have larger through-holes, and the remaining parts have smaller through-holes. In this case, only a small number of through-holes, where the piezoelectric device is disposed, has a large size, and the remaining through-holes occupying most of the flexible patch 30 have a sufficiently small size in which the skin is held, and thus the flexible patch 30 still has strong adhesiveness.

In addition, flexible patch 30 is formed to have the auxetic structure property. For example, the furrow of the mold 810 is configured to form the plurality of through-holes having a circle-shaped plane and/or a dumbbell-shaped plane.

Specifically, when the flexible patch 30 has circular holes and dumbbell-shaped holes including circles at two ends and a middle connecting the circles at two ends in the form of a pillar with a smaller thickness than the diameter of the two ends (i.e., dumbbell-hole pattern of through-holes), the flexible patch 30 having the through-holes may have the auxetic structure property. That is, the mold 810 is formed with a structure having a pillar surrounding a circular and/or dumbbell-shaped empty space. Using the mold 810 of FIG. 9C, the flexible patch 30 including the through-holes having the plane of FIG. 9D may be obtained.

In an embodiment, to obtain high air permeability, the spacing between holes may be less than 60 μm as described above. In an example, as shown in FIG. 9C, the spacing between the center of a connector of a dumbbell through-hole $H_C$ and one end of another dumbbell through-hole $H_C$ may be 35 μm, and the spacing between one end of a dumbbell through-hole $H_C$ and another circular through-hole $H_B$ may be 25 μm. Additionally, the diameter of the circular through-hole $H_B$ may be 50 μm, and the inner spacing of one end of the dumbbell through-hole $H_C$ may be 100 μm. However, this is for illustration purposes only, and may be variously set based on air permeability, adhesiveness and durability of the flexible patch 30.

Figure 9A:
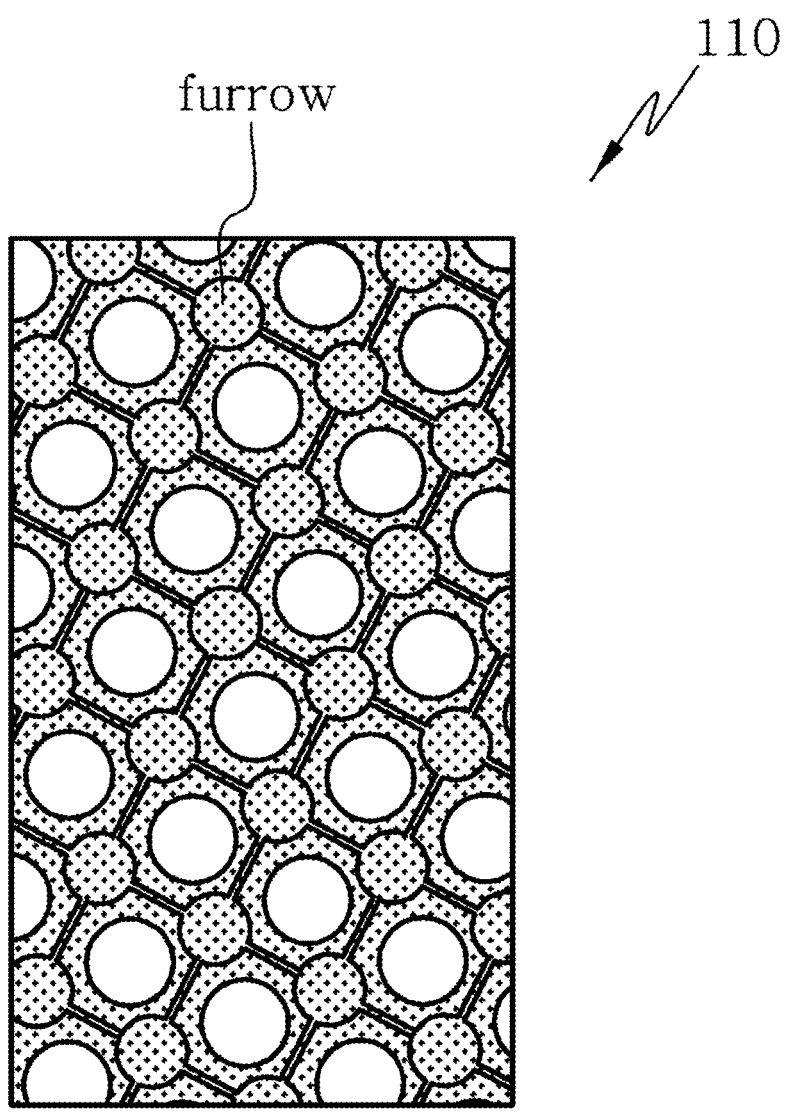
FIGS. 9A to 9D are diagrams illustrating a flexible patch formed by a mold, according to embodiments of the present disclosure.
Figure 9B:
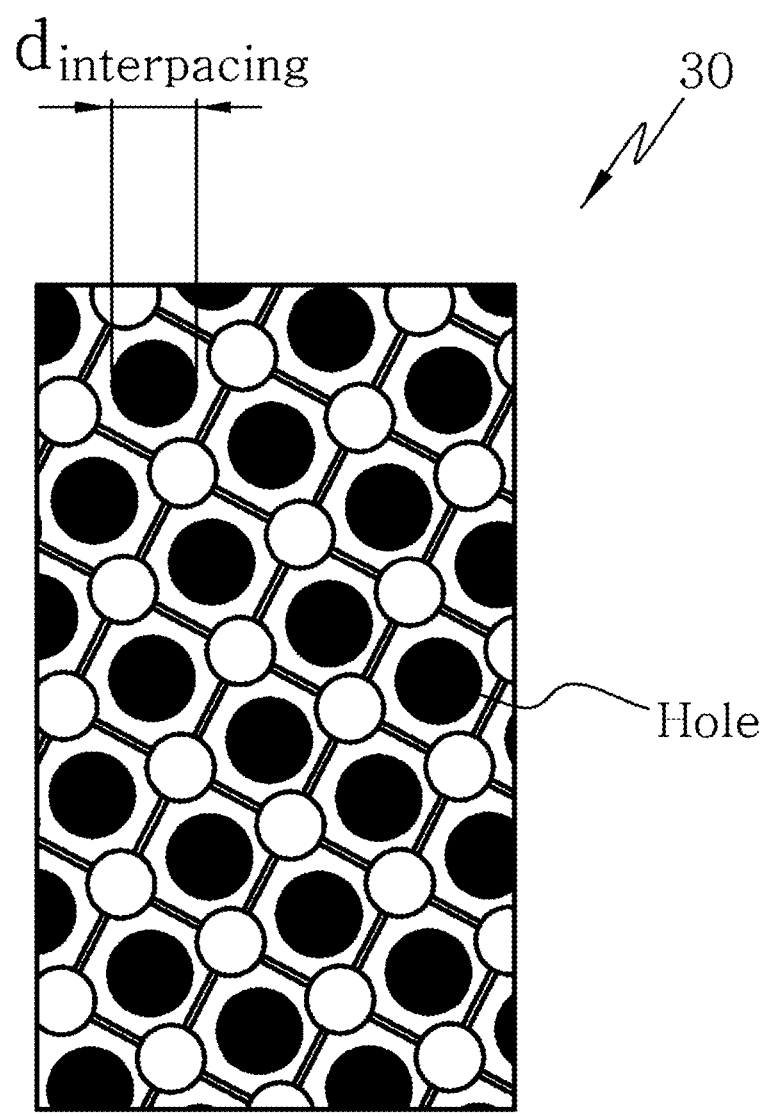
Figure 9C:
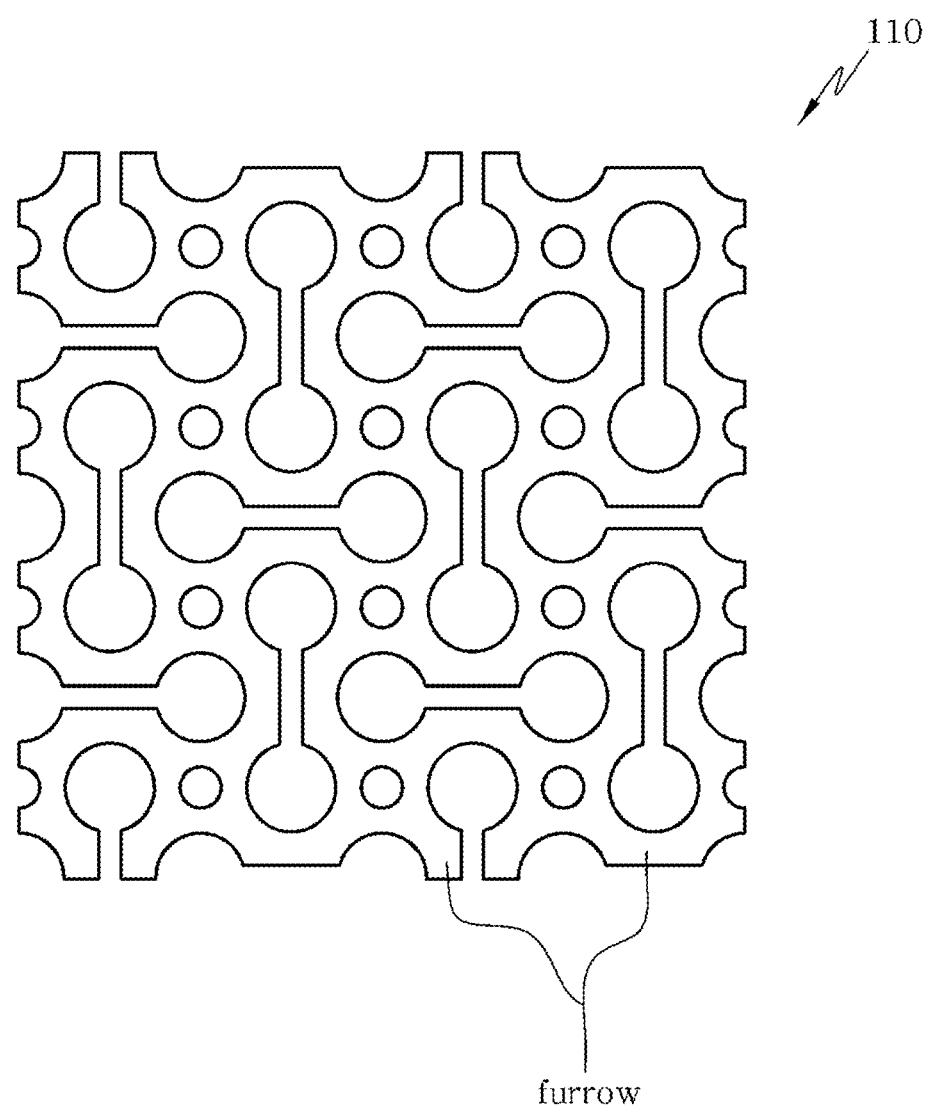
Figure 9D:
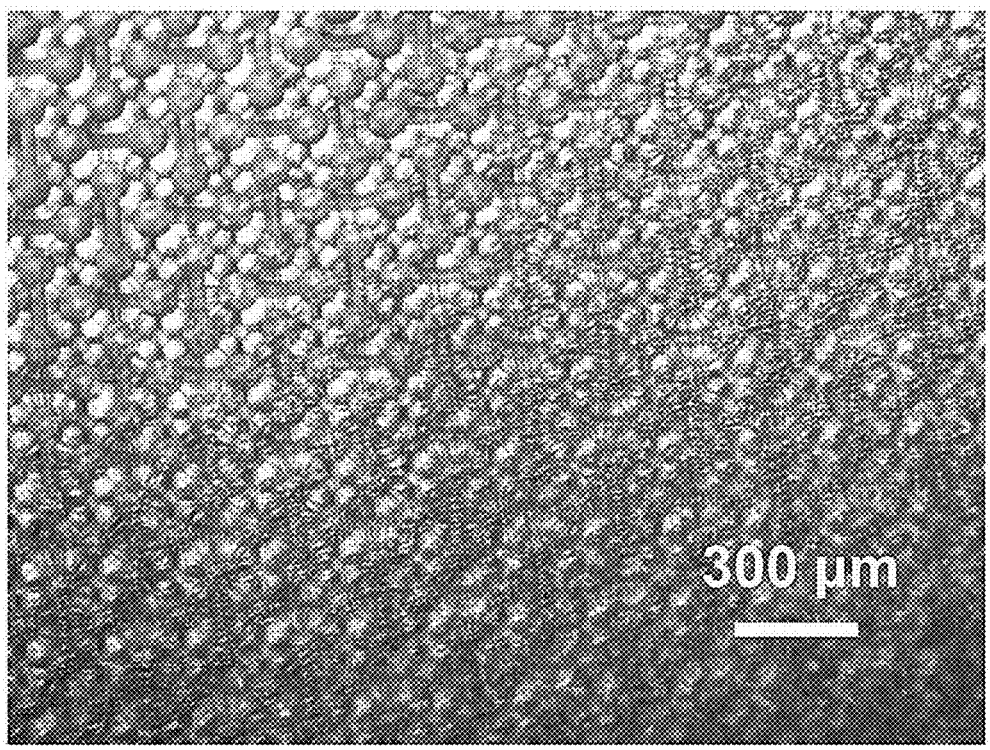

The sacrificial layer 820 may be formed on the mold 810 shown in FIG. 9A by a spin coating method.

However, if the spin coating method is applied to the embodiment using the mold 810 shown in FIG. 9C, it is impossible to separate the PDMS patch layer 830 from the mold 810 so as to manufacture the flexible patch 30 having the holes which are formed at intervals of several tens of micro scale (etc., interval of 60 μm). This is because the mold 810 shown in FIG. 9C is configured to form circular and dumbbell through-holes, so the contact area between the mold 810 and the PDMS patch layer 830 increases as compared to the embodiment using the mold 810 of FIG. 9A, and the spacing of the mold 110 is narrower, resulting in unbalanced PMMA spin coating.

Accordingly, the method for manufacturing the flexible patch 10 according to the second embodiment includes forming the sacrificial layer 120 on the mold 110 using an evaporation coating method (S130) as shown in FIG. 5. In an example, the evaporation coating method may be self-assembled monolayers (SAMs).

According to the above processes, the sacrificial layer 820 and the flexible patch layer 830 are formed on the mold 810 having the geometric plane associated with the auxetic structure property (S810 to S830). Then, the region of the flexible patch layer 130 exceeding the furrows is removed (S850), and the sacrificial layer 820 is etched to obtain the flexible patch 30 with the geometric plane having the auxetic structure property.

The flexible patch 30 manufactured by using the mold 810 of FIG. 9C causes about 6% of moisture change in comparison of changes in skin moisture before and after the flexible patch 30 is adhered to the skin. That is, even when the flexible patch 30 is adhered to the skin, a moisture loss of the skin hardly occurs.

Referring back to FIG. 8, the sacrificial layer 820 is made of a material that can be used to manufacture nano-scale or micro-scale semiconductor devices. In an embodiment, the sacrificial layer 820 is made of a material including poly (methyl methacrylate) (PMMA). However, the sacrificial layer 820 is not limited thereto, and may be made of a material including polymer.

In an embodiment, the sacrificial layer 820 is formed on one surface of the mold 810 having the concave furrows by a spin coating method (S810). The sacrificial layer 820 is formed with a thickness that can prevent the adhesion between the mold 810 and the flexible patch layer 830, and can be easily removed by the etching solution in S870.

The flexible patch layer 830 is made of a material having flexible properties to allow conformable contact so that the shape of the patch can deform along the skin contour, and having adhesiveness enough to adhere to skin. In an embodiment, the flexible patch layer 830 may be made of elastomer having similar mechanical properties to skin. In an example, the flexible patch layer 830 may be made of a material including poly-dimethylsiloxane (PDMS).

In some embodiments, the flexible patch layer 830 may be formed with a predetermined thickness. When the thickness of the flexible patch layer 830 is too small, durability enough to adhere to skin repeatedly several times may not be obtained. In an example, the flexible patch layer 830 may be formed with the thickness of 75 μm or more.

In forming the flexible patch layer 830 on the sacrificial layer 820 (S830), the flexible material (e.g., PDMS) that forms the flexible patch layer 830 fills the furrows. The flexible material fills the furrows, and further, may flood out of the furrows. When a larger amount of flexible materials than the internal volume of the furrows is supplied and the flexible material floods out of the furrows, a portion of the flexible patch layer 830 may be formed at a higher position than the surface of the mold 810.

The structure including the mold 810, the sacrificial layer 820 and the flexible layer 830, obtained by filling or flooding the furrows with the flexible material is, for example, similar to a structure in which a cast is poured into the mold before completing a cast product. Hereinafter, to help a understanding of those skilled in the art, the cast-mold structure used herein refers to a structure including the mold 810, the sacrificial layer 820 and flexible material 830, in which the flexible material fills the furrows (or floods the furrows) as shown in S830 of FIG. 8, and the flexible material may be soft or rigid.

After the flexible patch layer 830 is formed, the flexible patch layer 830 (i.e., formed at the higher position than the surface of the mold 810) exceeding the furrows is removed (S850). In an embodiment, the flexible patch layer 830 region (i.e., excessive surface) exceeding the furrows of the mold 810 contacts a board 150, and the board 850 and/or the flexible patch layer 830 (i.e., the cast-mold structure) is rubbed to remove the region exceeding the furrows.

The board 850 serves as a plastering board that rubs to remove the flexible material of the excessive region. In an embodiment, the board 850 includes a substrate 851 and a sacrificial layer 852 formed on the substrate 851. The substrate 851 may have a structure (e.g., a flat structure) suitable for performing a rubbing function, durability and rigidity. Additionally, the substrate 851 may be made of a non-magnetic material. In an example, the substrate 851 may be made of a material including silicon (Si).

The sacrificial layer 852 may be made of a material that can be etched by the etching solution in S870. In an example, the sacrificial layer 152 may include the same material (e.g., PMMA) as the sacrificial layer 820. However, the sacrificial layer 852 is not limited thereto, and may be made of a material that can be etched by the etching solution in S870 and minimizes damage that may occur on the surface of the flexible patch layer 830 after removal in the process of rubbing in contact with the flexible patch layer 830 region exceeding the furrows.

In an embodiment, the sacrificial layer 852 may be formed on the substrate 851 by a spin coating method, but is not limited thereto, and may be formed on the substrate 851 by various coating methods.

The rubbing process in S850 may further include an additional process to remove the excessive region more efficiently.

In an embodiment, S850 may include heating the contact region between the flexible patch layer 830 and the board 850. For example, the flexible material of the region exceeding the furrows of the mold may be removed more efficiently by applying heat of 70° C. or above to the contact region between the flexible patch layer 830 and the board 30.

When heat is applied to the flexible patch layer 830 or the contact region, the rigidity of the contact region is weakened (i.e., having a soft structure state). Accordingly, when rubbing the board 850 against the flexible patch layer 830 (i.e., the cast-mold structure) (or when rubbing the cast-mold structure against the board 850), the flexible material of the exceeding region spreads out of the area occupied by the cast-mold structure by relative movements. For example, it is similar to a phenomenon that when putting a support plate on plaster and rubbing, the plaster under the support plate spreads out of the area occupied by the support plate. Eventually, the height of the excessive region gradually becomes lower, and as shown in FIG. 8, the topmost of the flexible material filled in the furrows is on a level with the surface where the furrows are formed.

In an embodiment, S850 may include flipping so that the flexible patch layer 830 is disposed on one surface of the board 850 in the course of contact. After flipping is performed, the flexible patch layer 830 (i.e., the cast-mold structure) is disposed on one surface of the board 850. In the above embodiment, the area of the board 850 may be larger than the area of the cast-mold structure.

In this placement, when rubbing the board 850 and the cast-mold structure, the flexible material of the excessive region spreads out of the area occupied by the cast-mold structure by movements of the cast-mold structure, and there is a lower probability that the flexible material of the excessive region will remain on the side of the cast-mold structure.

In an embodiment, S850 may further include applying the pressure to the contact region between the flexible patch layer 830 and the board 850. The pressure may be applied by using the magnet, shown in FIG. 8.

In an example, the cast-mold structure and the board 850 may be disposed in contact between a magnet 861 and a magnet 862. Accordingly, the pressure may be applied to the contact region by attracting forces between the magnet 861 and magnet 862. As described above, the cast-mold structure and the board 850 may be made of a non-magnetic material, and do not affect the interaction of attaching forces occurring between the magnet 861 and the magnet 862.

As a result of rubbing the cast-mold structure and the board 850, the time taken to remove the excessive region may be reduced, thereby improving the efficiency of the removal process.

After S850, the sacrificial layer 820 is etched using an etching solution in S870. The etching is performed with the controlled selectivity of the etching solution to etch the sacrificial layer 820 while not etching the mold 110 and the flexible patch layer 830. In an embodiment, the etching solution used to etch the sacrificial layer 820 may include acetone.

In an experimental embodiment, the cast-mold structure, from which the region of the flexible patch layer 830 exceeding the furrows has been removed, is dipped in the etching solution to remove the sacrificial layer 820, and the cast (i.e., the flexible patch layer 830) is separated from the mold 810. The separated flexible patch layer 830 includes a plurality of holes formed by the furrows of the mold 810. Because the flexible material in the furrows is on a level with the surface of the mold 810 in S850, the plurality of holes is formed of penetrating type. As a result, as shown in FIG. 8, the flexible patch layer 830 including the plurality of through-holes can be obtained, and the flexible patch layer 830 including the plurality of through-hole may be used as the flexible patch 30.

The time during which the cast-mold structure is dipped in the etching solution may be variously set. For example, the etching time of the cast-mold structure may be determined by the thickness of the furrow (i.e., the thickness of the flexible patch 30), the thickness of the sacrificial layer 820, and the cross sectional area of contact between the furrow and the flexible patch layer 830.

Additionally, for more efficient etching process in S870, ultrasonic treatment may be performed on the cast-mold structure in the etching solution.

Although the flexible patch 30 manufactured by S810 to S870 is manufactured with the micro scale thickness, adhesiveness may be increased by the plurality of holes. Additionally, the plurality of holes is a penetrating hole, and after the flexible patch 30 adheres to skin, the skin of the adhered region is not isolated from the external air. Accordingly, the flexible patch 30 can have both air permeability and adhesiveness, dissimilar to the conventional skin patch surface-treated such that only the patch surface has a micro structure (such as, for example, octopus suckers or gecko feet) and thus only adhesiveness is good and air permeability is relatively low.

Additionally, when the flexible patch layer 830 is separated from the mold 810 using the sacrificial layer 820, damage such as tear does not occur in the process of generating a plurality of holes (or a hole pattern) in the flexible patch layer 830 and separating the flexible patch layer 830.

The flexible patch 30 has very good adhesiveness to skin and air permeability, and thus can be used to manufacture a variety of skin-adherable electronic devices such as skin sensors.

In addition, the flexible patch 30 may have stronger adhesiveness by the material properties such as the components and thickness of the flexible patch layer 830.

FIGS. 10A to 10D are diagrams illustrating adhesiveness of the flexible patch 30 that adheres to skin, according to an embodiment of the present disclosure.

The through-holes of the flexible patch 30 are on micro scale, and because they are very small compared to the size of the flexible patch 30, they are omitted in FIG. 10 for clarity of description.

Figure 10A:
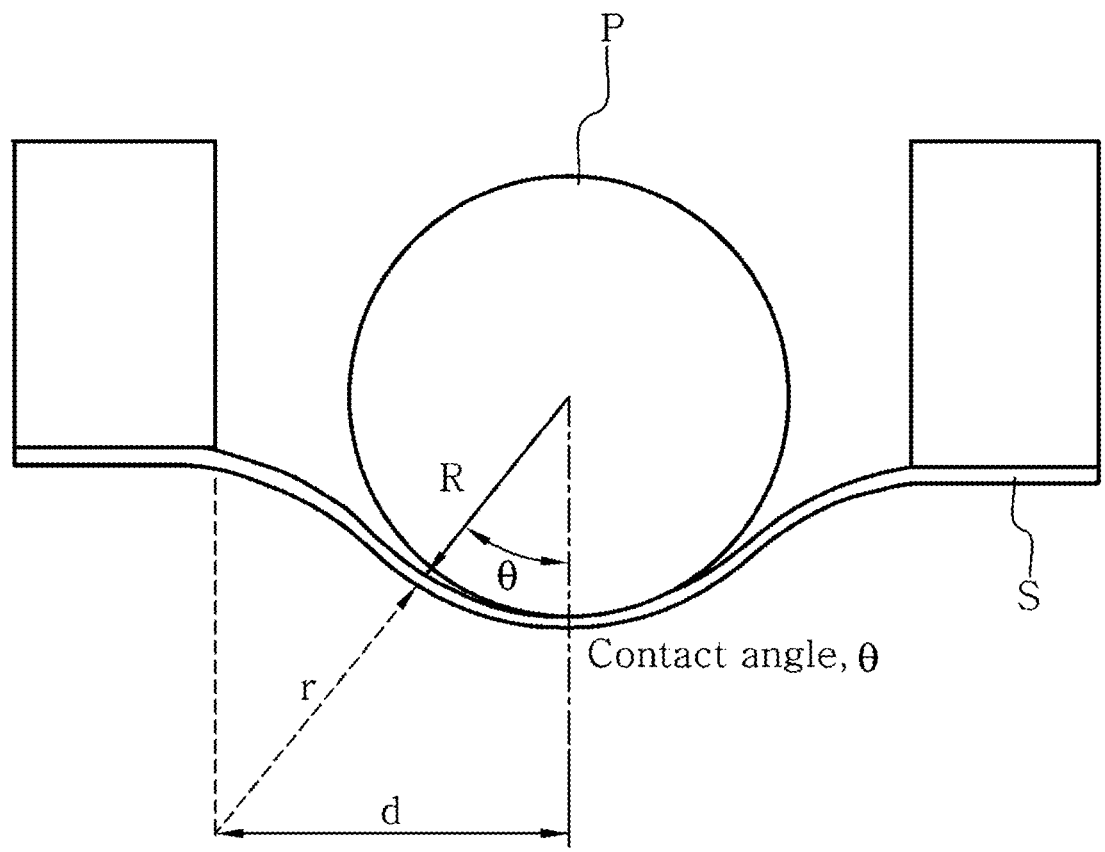
FIGS. 10A to 10D are diagrams illustrating adhesiveness of a flexible patch that adheres to skin, according to an embodiment of the present disclosure.

FIG. 10A is a diagram illustrating an adhesion principle between an object and a surface.

An ability of the object P that contacts the surface S to adhere to the surface S is determined by competition of structural resistance to deformation and interfacial interaction (competition in terms of reversibility and pluripotency). As shown in FIG. 10A, when the surface is deformed by the object P, energy between the object P and the surface S may be expressed by the following Equation 2-5.

$$U_{total} = U_{Adhesion} + U_{Bending} \quad [\text{Equation 2}]$$

$$U_{Adhesion} = -WbR(2\theta) \quad [\text{Equation 3}]$$

$$U_{Bending} = +\frac{bD\theta}{12R} \quad [\text{Equation 4}]$$

$$D = Et^3 \quad [\text{Equation 5}]$$

Here, $U_{total}$ denotes the total potential energy, $U_{adhesion}$ denotes adhesion energy between the object P and the surface S, and $U_{bending}$ denotes bending energy associated with the resistance of the surface S deformed by the object P. Here, the symbols for adhesion energy and bending energy merely indicate the direction of interaction, and in another embodiment, the symbol for the adhesion energy may be indicated by +, and the symbol for the bending energy may be indicated by −.

Additionally, W denotes the work of adhesion (Unit: N m$^{-1}$), b denotes the length of the object P adhered to the surface, R denotes the curvature, and θ denotes the contact angle which is an angle from the center of the contact region between the object P and the surface S to the point where the contact region ends. D is the flexural rigidity for the object P, and is determined by the elastic modulus (Young's modulus) of the object P and the thickness of the object.

To describe adhesiveness of the flexible patch 30 more simply, the case in which the flexible patch 30 of a monolayer structure adheres to the skin surface is described with reference to FIG. 10A.

When the case in which the flexible patch 30 adheres to the skin surface is applied to FIG. 10A, the surface S corresponds to the skin surface, and the object P corresponds to the flexible patch 30 including the flexible patch layer 830 having the through-holes. Accordingly, the flexural rigidity D for the flexible patch 30 is determined by the elastic modulus E of the flexible patch layer 830 and the thickness t of the flexible patch layer 830.

When adhesion energy is equal to or higher than bending energy, adhesion between the patch 30 and the skin surface is possible. When adhesion energy is less than bending energy, the patch 10 is detached from the skin surface. The critical work of adhesion Wc that determines to be adherable or not is determined by the following Equation 6.

$$\frac{dU_{total}}{d\theta} = -2W_c bR + \frac{bD}{12R} = 0 \quad [\text{Equation 6}]$$

When writing Equation 6 by Wc, the critical work of adhesion Wc at which adhesion between the object and the surface maintains is calculated as Wc=D/(24R$^2$). When the work of adhesion W between the flexible patch 30 and the skin surface is equal to or greater than the critical work of adhesion Wc, the flexible patch 30 can make a conformal contact with the skin surface. In contrast, when the work of adhesion W between the flexible patch 30 and the skin surface is less than the critical work of adhesion Wc, the flexible patch 30 does not contact the skin surface. Accordingly, to make adhesion between the flexible patch 30 and the skin surface possible, it is necessary that the magnitude of the critical work of adhesion Wc reduces, and/or the magnitude of the work of adhesion W between the flexible patch 30 and the skin surface increases.

Referring to Equation 5, when the patch 30 is made of a material having a high elastic modulus (e.g., a stiff material), and/or the thickness is large, the patch 30 has high flexural rigidity D. Accordingly, when the flexural rigidity D of the flexible patch 30 is low, and/or the work of adhesion between the skin surface and the flexible patch 30 is high, the flexible patch 30 can stably adhere to the skin surface.

In case that the elastic modulus E of the flexible patch 30 is low, when the thickness of the flexible patch 30 is small, the flexible patch 30 can stably adhere to the skin surface.

Additionally, the higher the adhesion energy between the flexible patch 30 and the skin surface, the stronger the adhesiveness of the flexible patch 30. Referring to Equation 2, adhesion energy between the skin surface and the flexible patch 30 relies on the work of adhesion W. The work of adhesion W between the flexible patch 30 and the skin surface is expressed by the following Equation 7.

$$W = \frac{4\gamma_{dPatch}\ \gamma_{dskin}}{\gamma_{dPatch} + \gamma_{dskin}} + \frac{4\gamma_{pPatch}\ \gamma_{pskin}}{\gamma_{pPatch} + \gamma_{pskin}} \quad [\text{Equation 7}]$$

Here, $\gamma_d$ denotes the dispersive component of the contact surface, and $\gamma_p$ denotes the polar component of the contact surface. $\gamma_{dSkin}$ denotes the dispersive component of the contact surface of the skin, $\gamma_{dPatch}$ denotes the dispersive component of the contact surface of the patch 30, $\gamma_{pSkin}$ denotes the polar component of the contact surface of the skin, and $\gamma_{pPatch}$ denotes the polar component of the contact surface of the patch 30. The flexible patch 30 is formed based on the above Equation 7.

As described above, the flexible patch 30 may be used to manufacture skin sensors. The PDMS patch 30 having the exemplary elastic modulus of 1 MPa enough to support micro scale ultra-small devices in the micro thickness range can adhere to the skin. $\gamma_d$ and $\gamma_p$ of the skin surface may be different for each part, but the maximum and minimum ranges of the variables are known as shown in the following Table 1.

TABLE 1

| $mNm^{-1}$ | $\gamma_d$ | $\gamma_p$ |
|---|---|---|
| Skin Max | 40 | 8 |
| Skin Min | 11.7 | 1.7 |
| PDMS (E = 1 MPa, t = 1 mm) | 19.1 | 0.5 |

When applying data of the above Table 1 to the above Equation 7, the work of adhesion W between the skin and the PDMS patch 30 is roughly calculated as follows: $31 \leq W \leq 54$ mJ m$^{-2}$.

To adhere the thickness of the PDMS patch 30 having the elastic modulus of 1 MPa to all types of skins, it should be able to adhere to skin surface having the lowest work of adhesion (Skin Min). Accordingly, the PDMS patch 30 should have the value of Wc=31. Accordingly, when the PDMS patch 30 is formed with the thickness of about 80 μm, the critical work of adhesion Wc requirement is satisfied. Accordingly, when the single flexible patch 30 of 1 MPa is manufactured with the thickness of less than 80 μm, conformal adhesion to skin surface is possible.

In some embodiments, when the single flexible patch 30 having the elastic modulus lower than 1 MPa has the thickness of less than 80 μm, it may have stronger adhesiveness. In other embodiments, one layer of the flexible patch 30 having the elastic modulus lower than 1 MPa can make a conformable contact with the skin surface at the thickness of 80 μm or more. For example, even when the thickness of one layer that adheres to the skin surface is 100 μm, it can adhere to the skin.

As described above, the flexural rigidity D is associated with the ability of the flexible patch 30 to adhere, and is also associated with the ability of the flexible patch 30 to maintain the shape. Referring to the above Equations 5 and 6, in case that the elastic modulus E of the flexible patch 30 is low, and/or when the thickness of the flexible patch 30 is small, the flexible patch 30 can stably adhere to the skin surface.

However, when the thickness of the flexible patch 30 is too small or the flexible patch 30 is formed with too low elastic modulus, considering only adhesiveness, it is difficult to handle. Specifically, when the flexural rigidity of the flexible patch 30 is too low, the flexible patch 30 is bent, making it difficult to handle, and it is difficult to uniformly maintain the shape of the flexible patch 30. Accordingly, when the flexural rigidity of the flexible patch 30 is too low, it is difficult to integrate other elements on the flexible patch 30.

To overcome this problem, the flexible patch 30 may be configured such that a region that adheres to skin has lower flexural rigidity, and a region that does not adhere to skin and thus has a lower need for high adhesiveness, and where other elements are integrated, has flexural rigidity enough to maintain the shape without being subjected to bending. For example, the flexible patch 30 may be formed as one or more layers to have stronger adhesiveness and flexural rigidity enough to support other elements (for example, including electrodes, semiconductor devices, interactions, etc.). To manufacture the flexible patch 30, the flexible patch layer 830 that is formed on the sacrificial layer 820 may include one or more sub-layers.

Figure 10B:
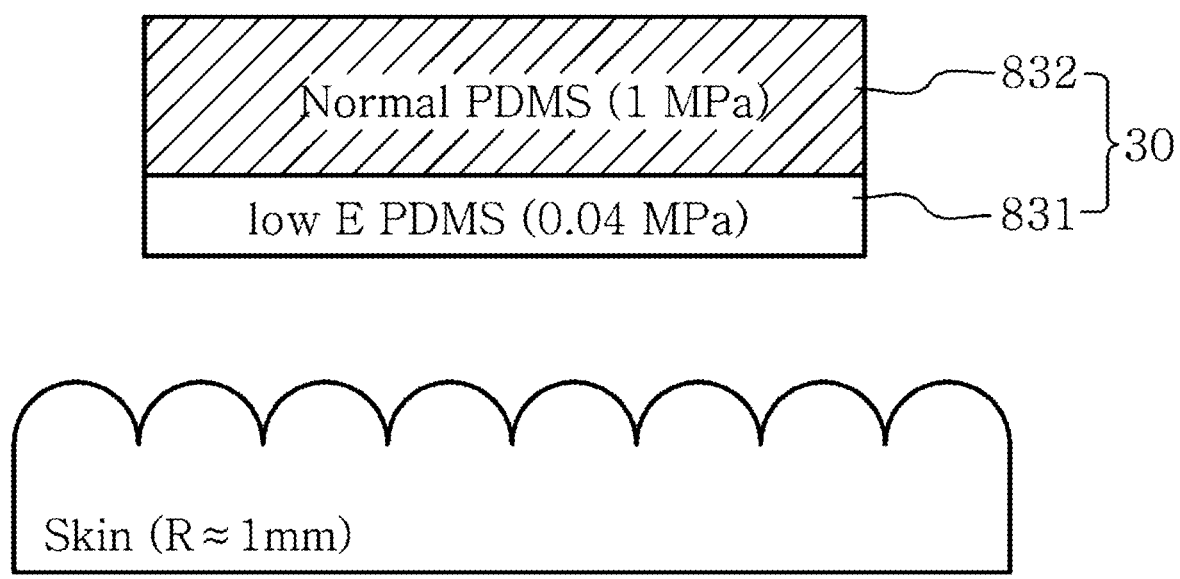
Figure 10C:
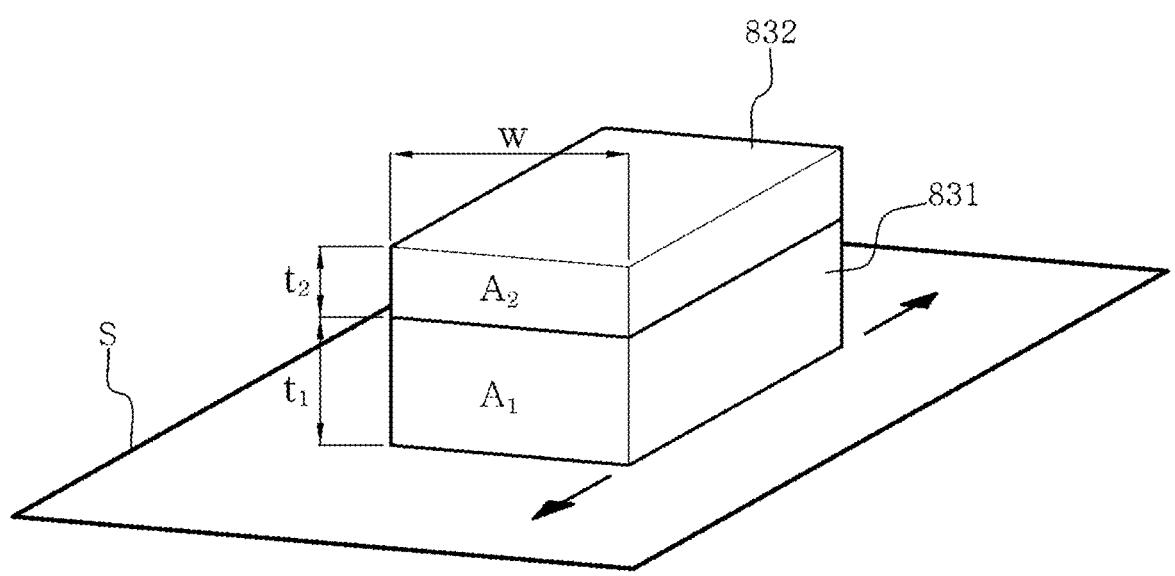

FIG. 10B is a diagram illustrating the flexible patch 10 of bi-layer structure having different elastic moduli according to an embodiment of the present disclosure.

In an embodiment, the flexible patch 30 having a bi-layer structure may include two sub-layers (a first flexible layer 831, and a second flexible layer 833 in FIG. 10B) with different rigidities.

Here, the first flexible layer 831 that adheres to skin has a lower flexural rigidity D1 than the flexural rigidity D2 of the second flexible layer 832 that does not adhere to skin. The first flexible layer 831 has the lower elastic modulus (such as 0.04Mpa) as to be comfortable adhesion to the surface of the skin. Meanwhile, the second flexible layer 832 has the higher elastic modulus. Hence, the second flexible layer 832 is be easily handled by controlling the flexible patch 30 and supports the device integrated on the flexible patch 30 such as semiconductor circuit.

For example, as shown in FIG. 4B, the first flexible layer 131 has the elastic modulus $E_1$ of 0.04 MPa, and the second flexible layer 132 has the elastic modulus $E_2$ of 1 MPa, and thus the first flexible layer 131 may be more softer.

In an embodiment, the flexible patch layer 830 may include the first flexible layer 831 and the second flexible layer 832 including a pre-polymer and a curing agent. Here, the second flexible layer 832 may have a higher ratio of curing agent than the ratio of curing agent of the first flexible layer 831. For example, the first flexible layer 831 may have a ratio of the pre-polymer and the curing agent of 40:1, and the second flexible layer 832 may have a ratio of pre-polymer and the curing agent of 10:1. Due to this ratio difference of the curing agent, the flexural rigidity D of the first flexible layer 831 and the second flexible layer 832 is differently determined.

By this difference in constituent material, the first flexible layer 831 is softer and stickier than the second flexible layer 832, allowing the flexible patch 30 to adhere to the skin. When the flexible patch 30 is used to manufacture a skin sensor, the more rigid second flexible layer 832 serves as a support (e.g., a substrate) for integration of micro scale devices.

Additionally, the first flexible layer 831 and the second flexible layer 832 may be formed with different thicknesses. Referring back to the above Equation 5, the flexural rigidity D is determined dependent on the elastic modulus E and the thickness.

Figure 10D:
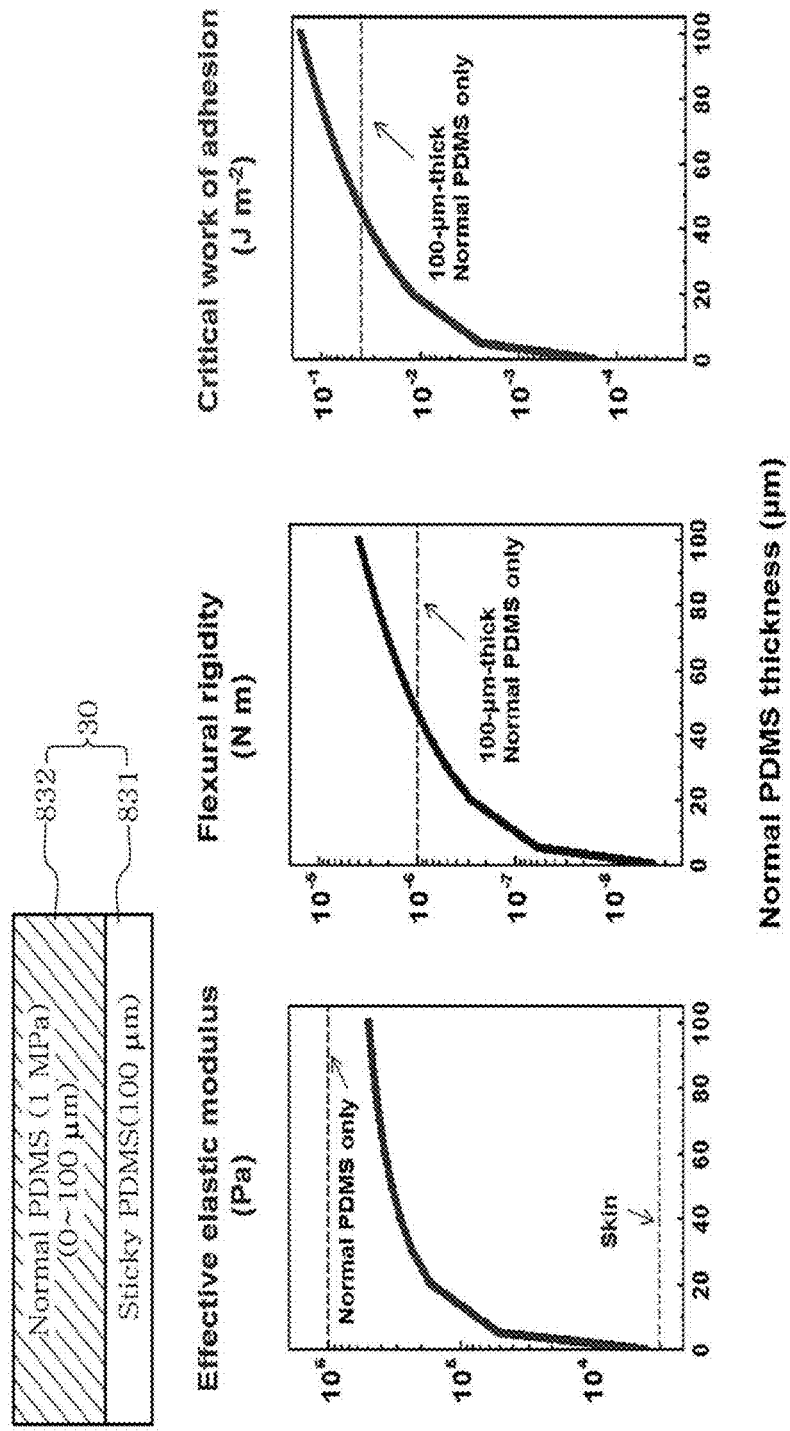

FIG. 100 is a diagram illustrating the flexible patch 30 of bi-layer structure having different thicknesses, according to the first embodiment of the present disclosure, and FIG. 10D is a diagram illustrating a graph showing the characteristics of the flexible patch as a function of the thickness of the bi-layer structure, according to the first embodiment of the present disclosure.

As shown in FIG. 100, when the flexible patch 30 of bi-layer structure adheres to skin surface, generally, due to the nature of skin surface having a curved structure, the adhered flexible patch 30 is expanded. A restoring force $F_{ret}$ that tends to return to a state before expansion is applied to the expanded flexible patch 30. The restoring force $F_{ret}$ may be analyzed as shown in the following Equation 8. When the first flexible layer 831 and the second flexible layer 832 of the flexible patch 30 are made of the same material (e.g., PDMS), they may have the same tensile stress σ and tensile strain £.

$$F_{ret}=F_1+F_2=w\in(t_1E_1+t_2E_2) \qquad \text{[Equation 8]}$$

Here, $F_1$ denotes the restoring force that is applied to the first flexible layer 831 adhered to skin, and $F_2$ denotes the restoring force that is applied the second flexible layer 832 adhered to skin. The variable $t_1$ denotes the thickness of the first flexible layer 831, and $t_2$ denotes the thickness of the second flexible layer 832.

The total elastic modulus $E_N$ of the flexible patch 30 of bi-layer structure may be expressed by the following Equation 9.

$$E_{eq} = \frac{F_{ret}/w(t_1E_1+t_2E_2)}{\epsilon} = \left(\frac{t_1}{t_1+t_2}\right)E_1 + \left(\frac{t_2}{t_1+t_2}\right)E_2 \qquad \text{[Equation 9]}$$

In an example, when the first flexible layer 831 having the elastic modulus of 0.04 MPa that adheres to skin is formed with the thickness of 100 μm, the graph of the effective elastic modulus and the flexural rigidity of the flexible patch 30, and the critical work of adhesion between the flexible patch 30 and the skin surface may be calculated by the above Equation 9, and the results are shown in FIG. 10D.

The first flexible layer 831 and the second flexible layer 832 included in the flexible patch 30 of bi-layer structure may be formed to have a suitable thickness and elastic modulus for the function of a product (e.g., a skin sensor) for which the flexible patch 30 is used, with reference to the above Equation 9.

The above description of the flexible patch layer 830 of bi-layer structure is for illustration only, and it is not interpreted that the flexible patch layer 830 of the present disclosure is limited to a bi-layer structure. In other embodiments, the flexible patch layer 830 may be formed with a mono-layer and a triple-layer structure. In an example, the flexible patch layer 830 may be formed with a mono-layer structure including only the second flexible layer 833. In another example, the flexible patch layer 830 may be formed with a triple-layer structure including a rigid second flexible layer between two soft first flexible layers. The flexible patch layer 830 of triple-layer structure may include two first flexible layers having different thicknesses. For example, the first flexible layer of the region that adheres to skin may be formed with the thickness of 10 μm, and the first flexible layer on the opposite side may be formed with the thickness of 100 μm.

Additionally, 1 MPa disclosed as the elastic modulus for supporting the micro device on micro scale is only for illustration purposes, and the second flexible layer 832 included in the flexible patch 30 may have a different elastic modulus.

Accordingly, as the flexible patch 30 is manufactured using the sacrificial layer 820, damage does not occur in the process of obtaining the flexible patch layer 830 of micro scale thickness, and thus the flexible patch 30 can have high durability.

Referring back to FIG. 4, after the first substrate 101, the sacrificial layer 105 and the sensor circuit unit 10 are formed, the flexible patch 30 may be bonded to the active layer 115 of the sensor circuit unit 10 (S430). The bonding may be performed by the common wafer bonding technique. In an embodiment, for bonding between the flexible patch 30 manufactured by the manufacturing process of FIG. 8 and the active layer 115, the semiconductor structure and the flexible patch 30 may be plasma-treated (e.g., $O_2$ plasma-treated) to activate the bond surface of the semiconductor structure and the flexible patch 30.

In certain embodiments, when the flexible patch 30 is a bi-layer structure including a stickier layer and a more rigid layer, the bond surface of the flexible patch 30 may be a surface of the more rigid layer. In other embodiments, when the flexible patch 30 is a triple-layer structure including two sticker surfaces and one more rigid surface, the bond surface of the flexible patch 30 may be a surface of any one of the stickier layers.

Additionally, before the plasma treatment, an insulating layer (such as, for example, SiO2) may be further formed on the semiconductor structure of FIG. 5D. In certain embodiments, for bonding, the pressure may be additionally applied to the flexible patch and the semiconductor structure.

Subsequently, the flexible patch 30 having the surface activated by the plasma treatment is disposed on the semiconductor structure, and the flexible patch 30 is bonded to the semiconductor structure (i.e., the active layer 115) (S430).

Additionally, the sacrificial layer 105 is removed through the process such as etching, to obtain the skin sensor 1 including the flexible patch 30 as a flexible adhesive substrate that adheres to skin and the sensor circuit unit 10 integrated onto the flexible adhesive substrate (S450).

The etching is performed with the controlled etching selectivity to etch the sacrificial layer 105 while not etching the elements of the skin sensor 1 (including the sensor circuit unit 10 and the flexible patch 30). The etching solution used to etch the sacrificial layer 105 may include acetone.

The bonding process (S430) may be performed further based on the placement between the elements of the skin sensor 1 to maximize the air permeability of the skin sensor 1.

The elements of the skin sensor 1 may be arranged based on the operation principle of the skin sensor. As described with reference to FIG. 2, in the case of manufacturing the skin sensor 1 for sensing skin deformation, the flexible patch 30 has the through-holes disposed on the active layer 115 such that parts of the active layer 115 do not overlap the flexible material of the flexible patch 30 (S430). In an example, as described with reference to FIG. 2, the flexible patch is placed on the active layer so as to match the plurality of through-holes of the flexible patch to the plurality of through-holes of the insulation layer. Therefore, the deformation results of the active layer 115 disposed in air is obtained to the maximum extent.

Additionally, the flexible patch 30 is disposed further based on the elements below the active layer 115. In an embodiment, to manufacture the skin sensor 1, the through-holes H1 of the insulating layer 113 may be disposed on parts of the electrode 111 (for example, the extension bar included in the electrode 111A and 111B) or the entire electrode 111, the active layer 115 may be disposed on the through-holes H of the insulating layer 113, and the through-holes H2 of the flexible patch 30 may be disposed on the active layer 115. Here, as shown in FIG. 2B, the through-holes H1 of the insulating layer 113 may match the through-holes H2 of the flexible patch 30 as indicated by the shaded area. Through this placement structure, the skin sensor 1 can effectively acquire skin information based on the operation of the active layer 115, and ensure high air permeability of the skin sensor 1.

In addition, to place the flexible patch 30 on the semiconductor structure (i.e., on the active layer 115), the flexible patch 30 may be disposed on an align glass. The surface of the flexible patch 30 may not be flat due to the flexible property. As the surface that adheres to skin is flatter, the adhesiveness of the flexible patch 30 increases. Accordingly, after the flexible patch 30 is disposed on the align glass such that the cross section of the flexible patch 30 is flat using a ruler, the flexible patch 30 may be transferred onto the semiconductor structure and the align glass may be removed to manufacture the skin sensor 1 having the flexible patch 30 with a flat surface. Accordingly, the adhesiveness of the skin sensor 1 may be maximized.

When the semiconductor device of the electronic device includes a piezoelectric material, the electronic device may be used as a skin sensor that adheres to skin to acquire skin deformation and/or elasticity information. The skin sensor 1 manufactured by the above-described process may operate as a sensor when adhered to skin. The piezoelectric material used to sense deformation is disposed on larger through-holes, and the skin sensor can acquire skin deformation information caused by the physiological behaviors of skin more efficiently.

Additionally, the skin sensor 1 according to various embodiments of the present disclosure may be used to measure dry skin as well as skin elasticity.

Second Embodiment

Figure 11A:
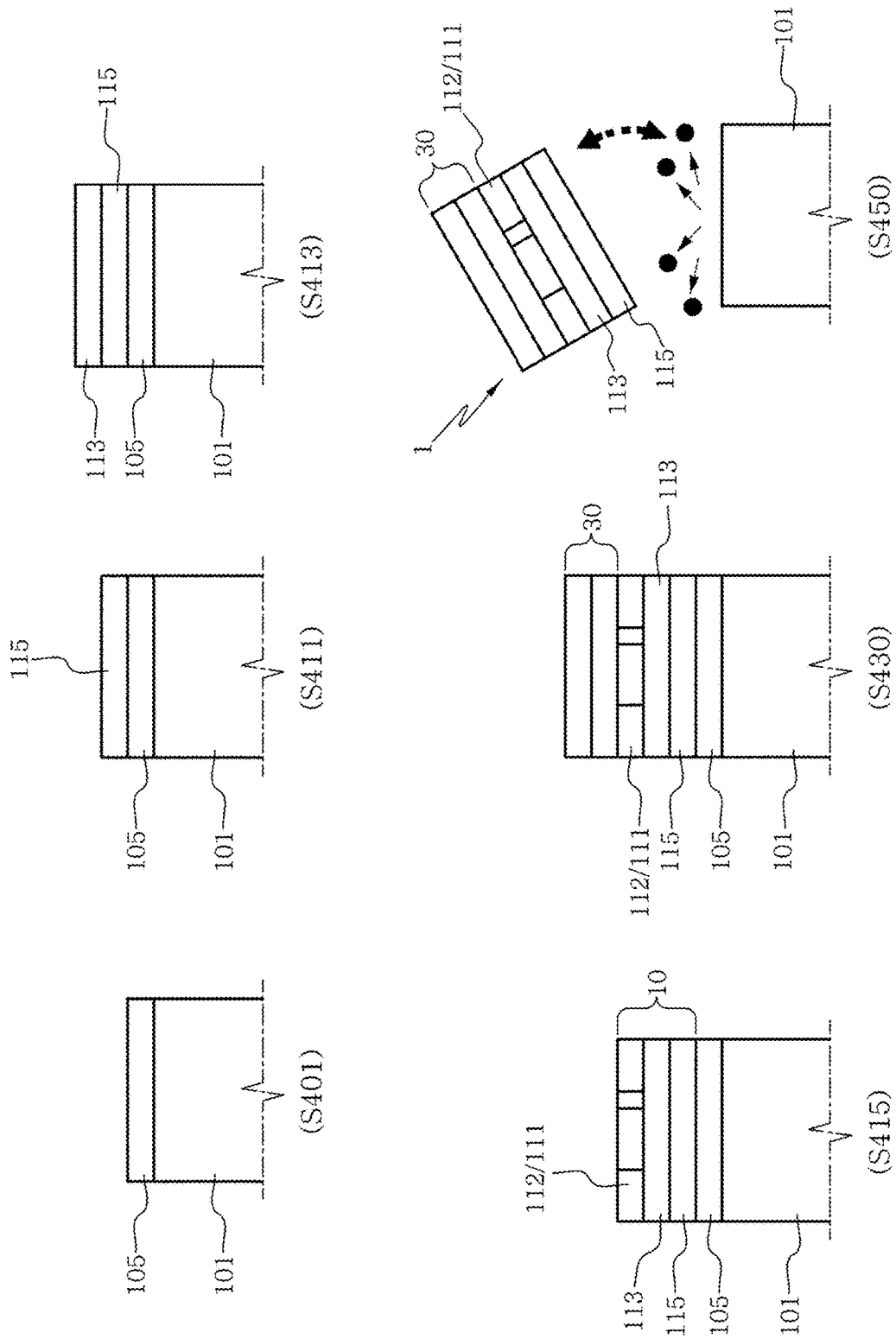
FIGS. 11A and 11B are schematic conceptual diagrams showing a process of manufacturing a skin sensor, according to a second embodiment of the present disclosure.
Figure 11B:
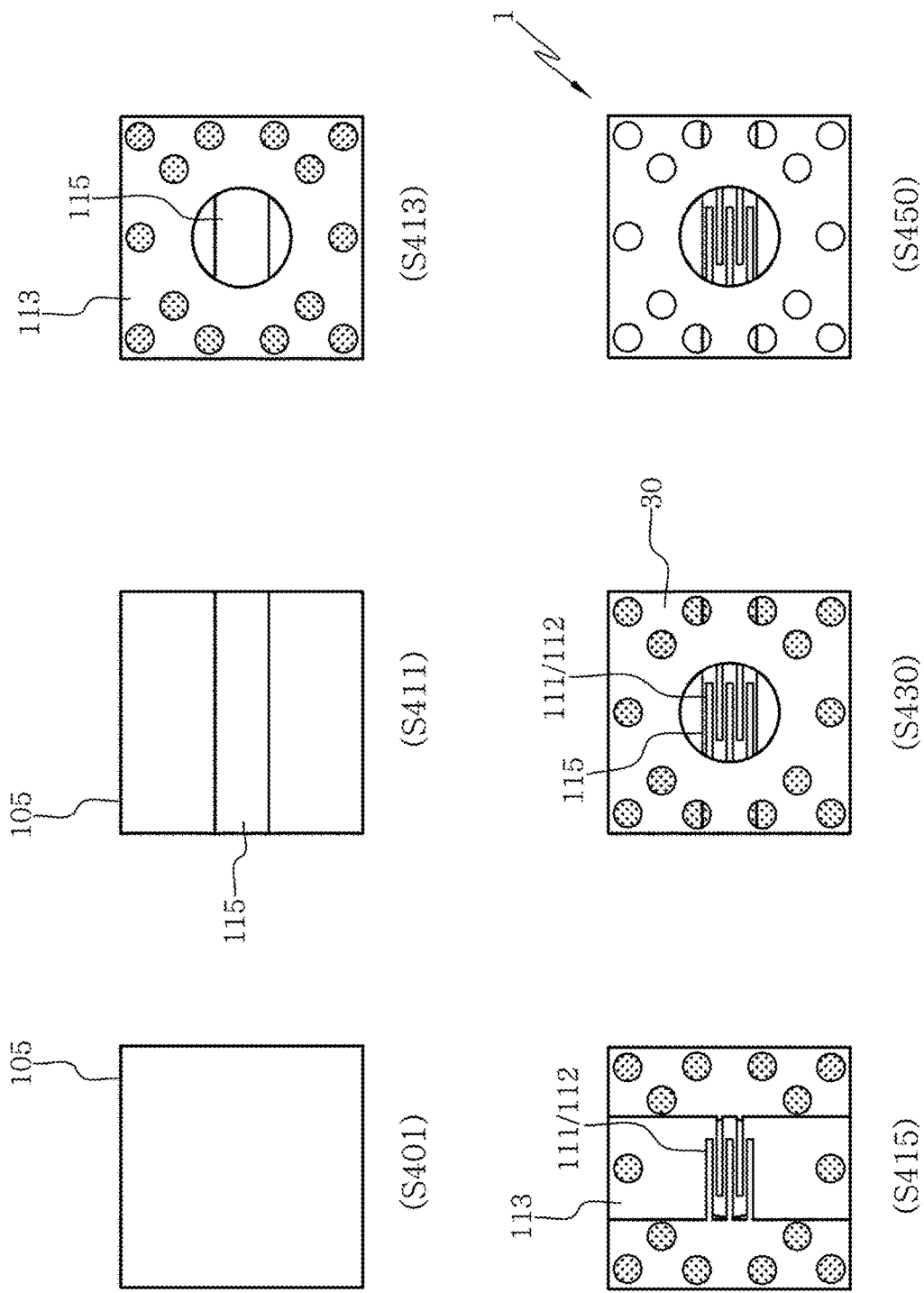

FIGS. 11A and 11B are schematic conceptual diagrams showing a process of manufacturing a skin sensor, according to a second embodiment of the present disclosure.

Referring to FIGS. 4 and 11, a method of manufacturing a skin sensor according to the second embodiment of the present disclosure is so much similar to the method of manufacturing a skin sensor according to the first embodiment of FIG. 4, and will be described primarily based on difference(s).

As shown in FIG. 4, among the elements of the sensor circuit unit 10, the active layer 115 of the sensor circuit unit 10 is disposed closest to the flexible patch 30.

However, in other embodiments, among the elements of the sensor circuit unit 10, the active layer 115 of the sensor circuit unit 10 may be disposed farthest from the flexible patch 30. That is, the skin sensor 1 of FIGS. 1B and 10 may be manufactured.

The method of manufacturing the skin-adherable skin sensor 1 according to the second embodiment includes, similar to the first embodiment, forming a sacrificial layer 105 on a substrate 101 (S1101), forming a sensor circuit unit 10 on the sacrificial layer 105 (S1110), bonding the sensor circuit unit 10 and a flexible patch 30 including through-holes (S1130), and etching the sacrificial layer 105 to manufacture the skin sensor 1 (S1150).

In the above embodiment, the forming the sensor circuit unit 10 on the sacrificial layer 105 (S1110) may include forming an active layer 115 on the sacrificial layer 105 (S1111), forming an insulating layer 113 on the active layer 115 (S1113), and forming an electrode 111 and/or an interconnect 112 on the insulating layer 113 (S1115).

As described, the skin sensor 1 may be manufactured with the active layer 115 disposed on top of the skin sensor 1. The skin sensor 1 manufactured by the second embodiment has the same structure, and a difference is only that the positions of the circuit element (i.e., the electrode 111 and/or the interconnect 112) and the active layer 115 are switched. Accordingly, the operation principle of the skin sensor 1 of FIG. 11 is similar to the operation principle of the skin sensor 1 of FIG. 2, and its detailed description is omitted herein.

The method of manufacturing a skin-adherable electronic device according to the above-described embodiments may be such that the process of forming the semiconductor device and the process of manufacturing the flexible patch 30 including the plurality of through-holes are separated. However, according to other embodiments of the present disclosure, it is possible to manufacture the electronic device of the first embodiment or the second embodiment by an all-in-one process.

Third Embodiment

FIGS. 12A to 12H are schematic conceptual diagrams showing a process of manufacturing a skin sensor, according to a third embodiment of the present disclosure.

Referring to FIGS. 4 and 12, the method of manufacturing a skin sensor according to the third embodiment of the present disclosure is so much similar to the method of manufacturing a skin sensor according to the first embodiment of FIG. 4, and will be described primarily based on difference(s).

By the method of manufacturing a skin sensor according to the second embodiment, the skin sensor 1 having the same structure as the first embodiment may be manufactured. However, referring to FIG. 12, the method of manufacturing the skin sensor 1 according to the third embodiment of the present disclosure is an all-in one manufacturing process in which the process of manufacturing the flexible patch 30 and the process of manufacturing the semiconductor structure including the sensor circuit unit 10 are not separated. That is, it is different from the method of manufacturing the skin sensor 1 according to the first embodiment in which the process of manufacturing the flexible patch 30 and the process of manufacturing the semiconductor structure are separated.

Referring to FIGS. 12A to 12H, in the third embodiment, the method of manufacturing the skin-adherable skin sensor 1 includes forming a sacrificial layer 105 on a substrate 101 (S1201), forming a sensor circuit unit 10 on the sacrificial layer 105 (S1210), including forming an electrode 111 and/or an interconnect 112 on the sacrificial layer 105 (S1211), forming an insulating layer 113 on the electrode and/or the interconnect (S1213), and forming an active layer 115 on the insulating layer 113 (S1215). Additionally, the method includes forming a flexible patch layer 830 on the sensor circuit unit 10 (i.e., on the active layer 115) (S1230), contacting a mold 810 with the flexible patch layer 830 to form a plurality of through-holes (S1240), etching the sacrificial layer 105 to manufacture the skin sensor 1 (S1250), and removing the mold 810 (S1270).

Accordingly, the skin sensor 1 manufactured by the method of manufacturing the skin sensor 1 according to the third embodiment corresponds to a monolithic electronic device having all circuit elements and interconnectors on the flexible patch 30 as a flexible adhesive substrate. The advantages of the method of manufacturing the skin sensor 1 according to the third embodiment are the production of compact and light electronic devices, high integration and reliability of electronic devices, mass production and low price.

Figure 12A:
FIGS. 12A to 12H are schematic conceptual diagrams showing a process of manufacturing a skin sensor, according to a third embodiment of the present disclosure.
Figure 12A:
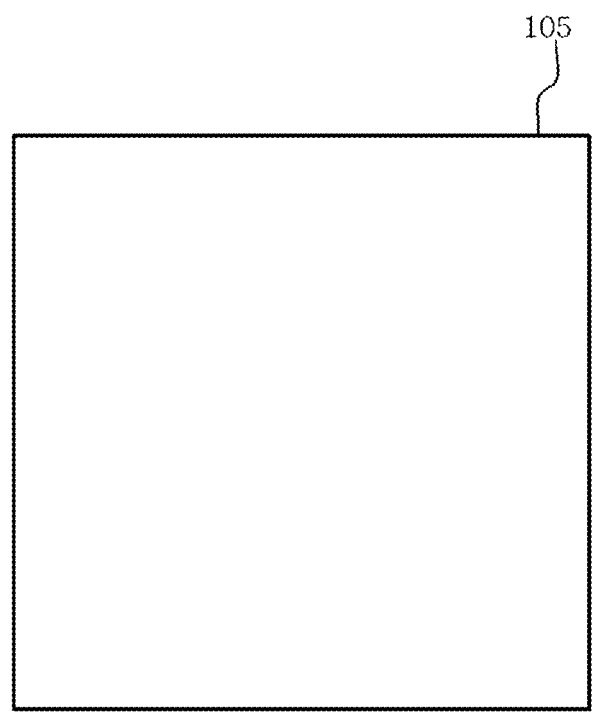
Figure 12B:
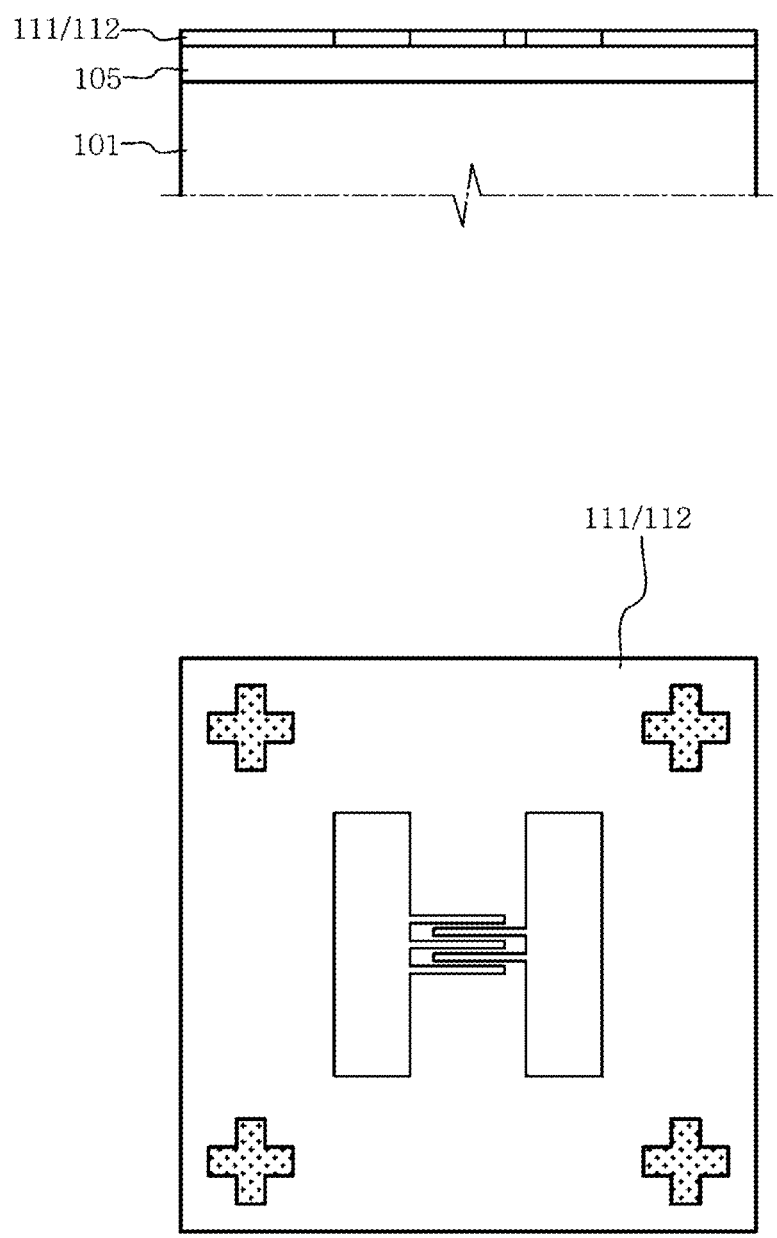

Referring to FIG. 12A, in an embodiment, the sacrificial layer 105 is formed, considering photo-lithography, etching selectivity and thermal stability. In an example, the sacrificial layer 105 may be made of a material including at least one of Cr, Al, Ni, Au and their combinations. In certain embodiments, the sacrificial layer 105 may be formed further considering costs. In this case, the sacrificial layer 105 may be made of, for example, a material including at least one of Cr, Al, Ni, and their combinations.

In S1210, the sensor circuit unit 10 including the polycrystalline active layer 115 (i.e., polycrystalline semiconductor structure) is deposited on the metal sacrificial layer 105. In an embodiment, the electrode 111 and the interconnect 112, the insulating layer 113 and the active layer 115 (for example, operating as a sensing material) are formed on the sacrificial layer 105 in that order.

In an example, the polycrystalline active layer 115 may be performed through transfer using stressor, similar to the first embodiment.

In another example, the polycrystalline semiconductor material can grow irrespective of the substrate, and is grown and formed directly on the sacrificial layer 105. For example, the polycrystalline active layer 115 may be formed by direct deposition using physical vapor deposition (PVD) methods such as sputtering and evaporation, or chemical vapor deposition (CVD) methods such as low-pressure CVD and plasma-enhanced CVD. In certain embodiments, growth of the polycrystalline active layer 115 may be performed at the temperature of 500° C. or less.

Figure 12C:
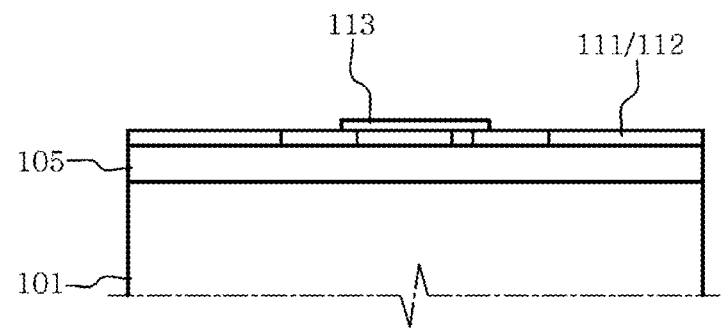
Figure 12C:
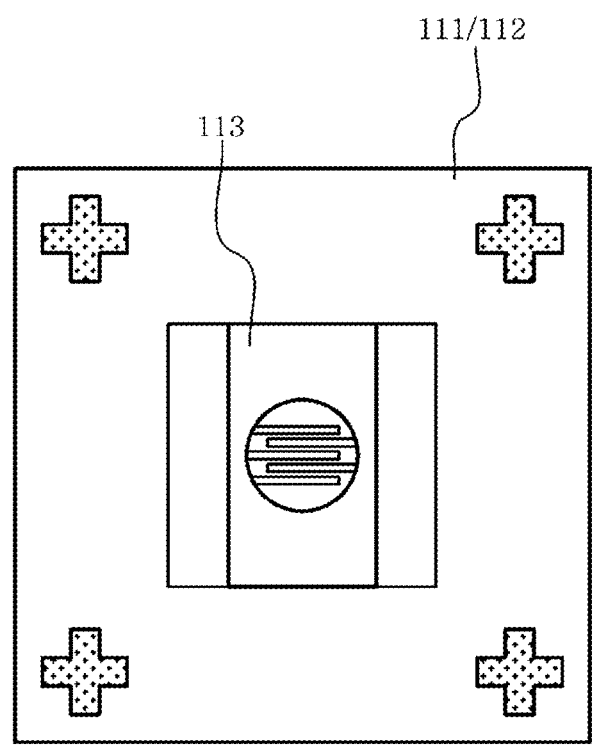
Figure 12D:
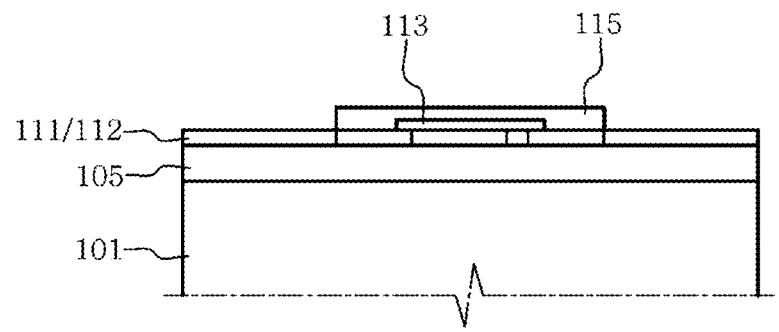
Figure 12D:
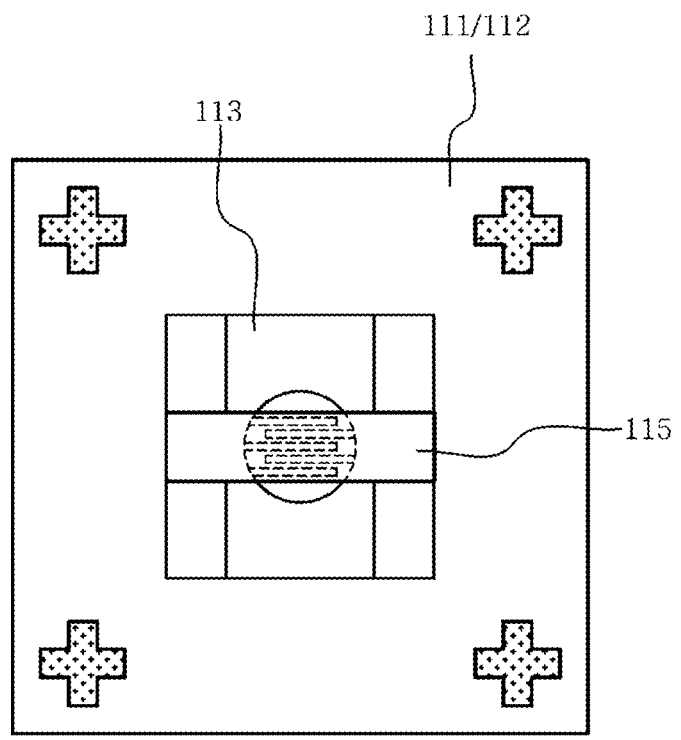
Figure 12E:
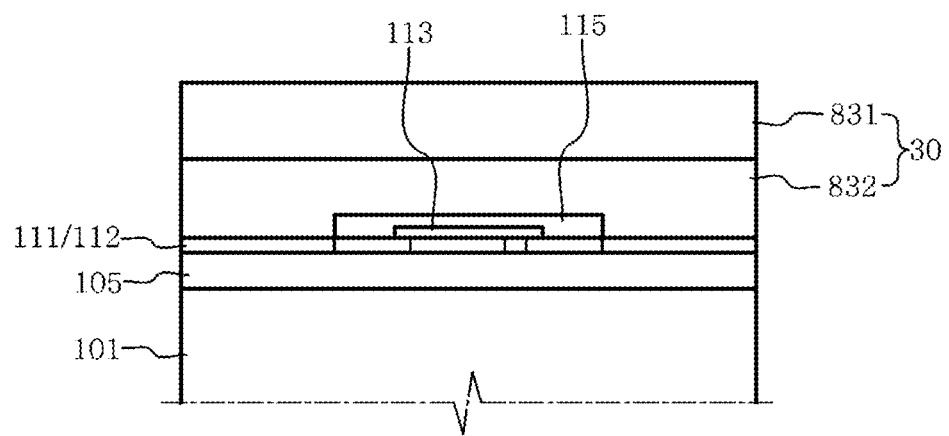
Figure 12E:
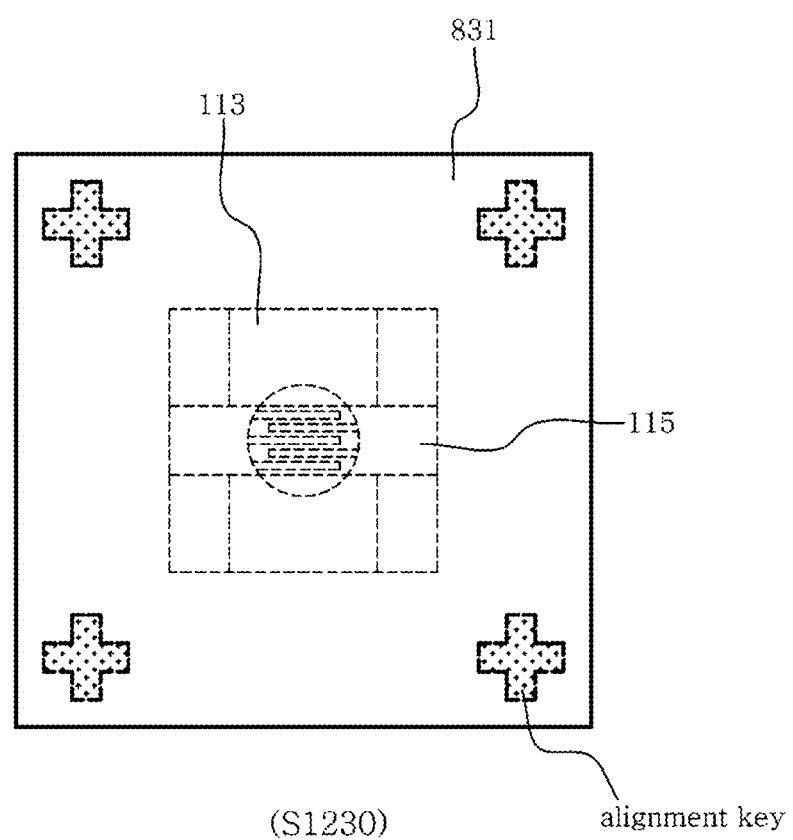
Figure 12F:
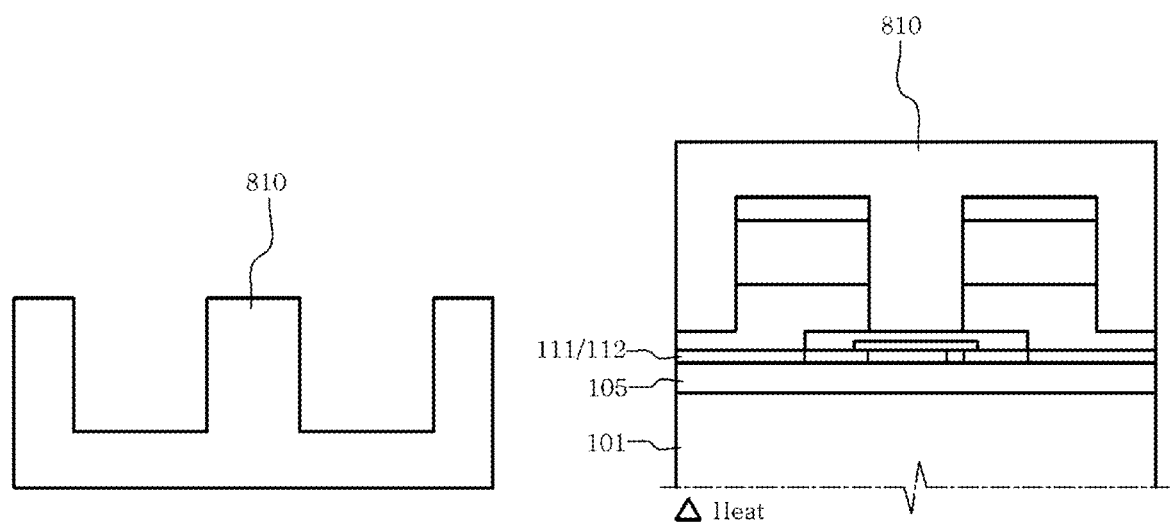
Figure 12F:
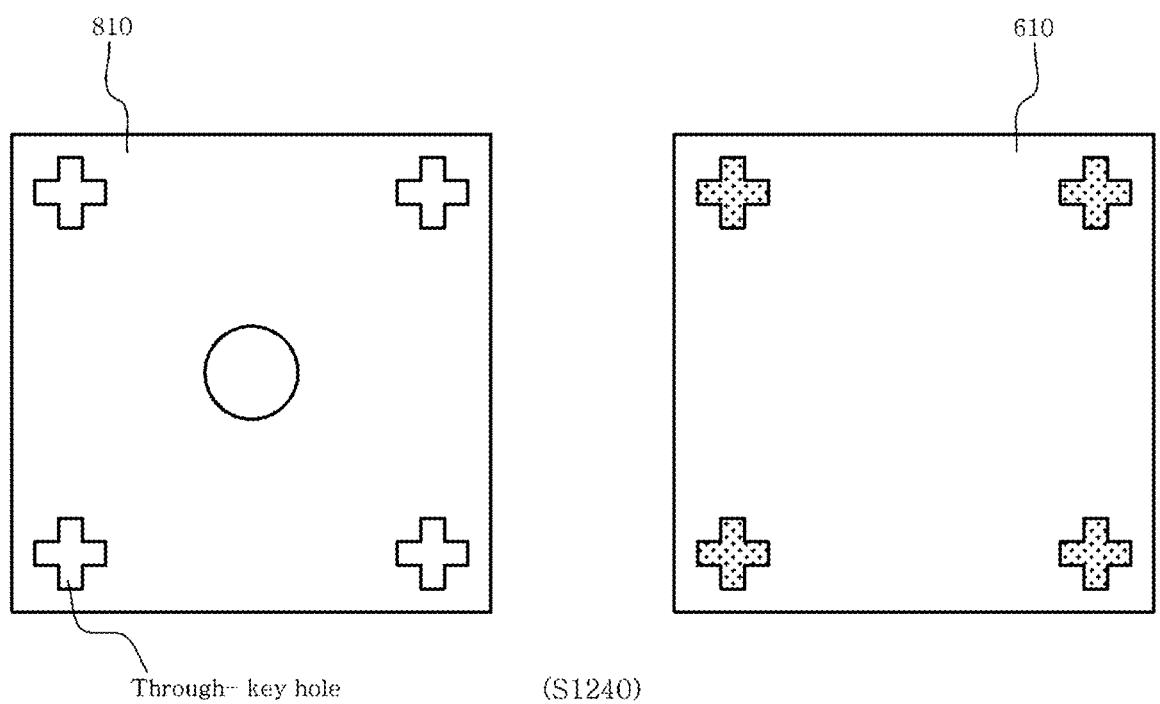
Figure 12G:
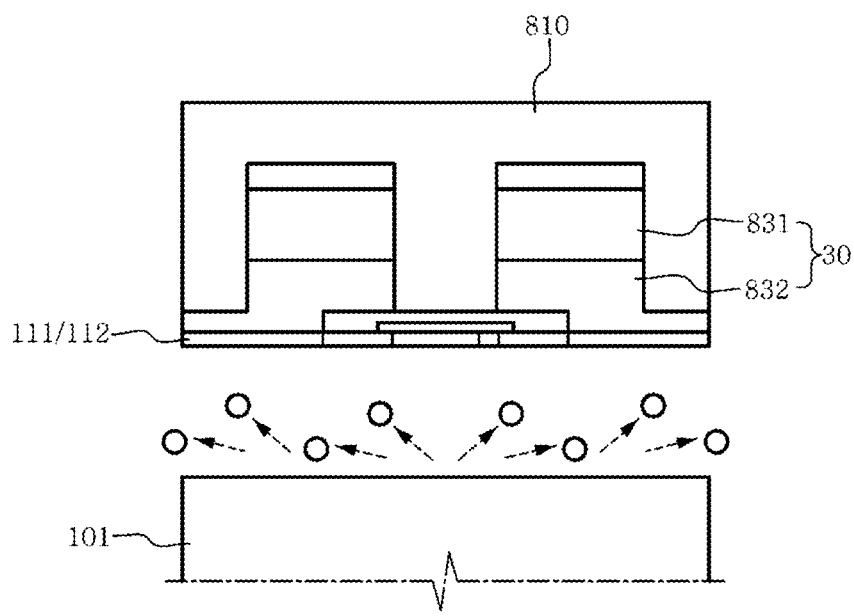
Figure 12H:
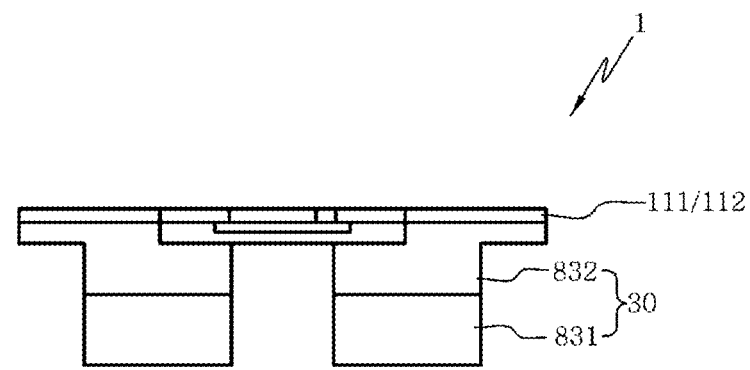
Figure 12H:
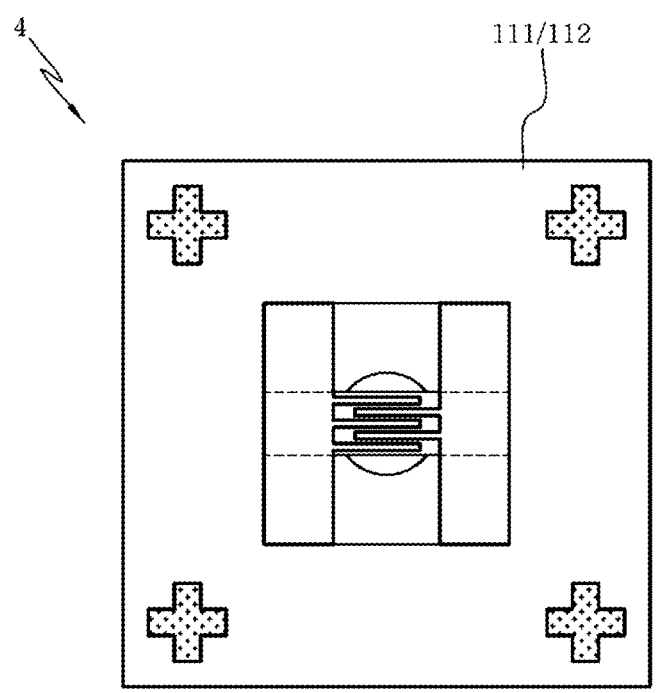

In an example, each layer is formed such that the insulating layer 113 has through-holes corresponding to the through-holes of the flexible patch 30 to ensure air permeability as shown in FIG. 12C.

S1201 and S1210 are performed by a photo-lithography based etching process.

Subsequently, a flexible patch layer 830 is formed on the sensor circuit unit 10 (S1230). The flexible patch layer 830 is the flexible patch 30 with no through-hole. The flexible patch layer 830 is formed directly on the sensor circuit unit 10 (S1230). The process of forming the flexible patch layer 830 and the components, structure and thickness of the flexible patch layer have been described in detail with reference to FIGS. 8 and 10, and its detailed description is omitted herein.

After the flexible patch layer 830 is formed, through-holes may be formed in the flexible patch layer 830.

In S1240, through-hole formation may be performed by a soft lithography based process. In an example, through-hole formation may be performed by a soft lithography process using micromolding.

Specifically, in an embodiment, to form through-holes, the mold 810 contacts the flexible patch layer 830 (S1240). The mold 810 may be configured with a furrow structure having the plane shape shown in FIGS. 9A and 9C. The furrow depth of the mold 810 may be equal to or greater than the thickness from the sensor circuit unit 10 (i.e., the active layer 115) to the flexible patch layer 830.

To form through-holes, the mold 810 contacts the flexible patch layer 830 to reach the sensor circuit unit 10 (i.e., the active layer 115). That is, the mold 810 is similar to stamping on a soft material. When the mold 810 contacts the flexible patch layer 830, the edges of the furrows penetrate the flexible patch layer 830 to form through-holes in the flexible patch layer 830.

In S1240, to allow the edge area of the furrows of the mold 810 to penetrate the flexible patch layer 830 more easily, a process of heating the flexible patch layer 830 may be further performed.

FIG. 12 shows the mold 810 only having through-holes where the active layer 115 is disposed, but this is merely for clarity of description. In S1240, the mold 810 that can form at least one through-hole may be used to enhance air permeability.

In 1240, through-holes may be formed to manufacture the free-standing skin sensor 1. That is, at least one of the through-holes formed by the mold 810 is disposed on the zigzag bar of the electrode 111 as described with reference to FIG. 6A.

In an embodiment, the through-holes are formed on parts of the electrode 111 based on at least one key hole included in the mold 810 and at least one alignment key included in the semiconductor structure. Accordingly, the skin sensor 1 may have a free-standing structure. The structure of the skin sensor 1 manufactured by the manufacturing method according to the second embodiment is the same as the structure of the skin sensor 1 according to the first embodiment, and thus skin information may be acquired by the same operation principle.

In the above embodiment, the mold 810 may include at least one key hole. The key hole is a through-hole that is different from the through-hole of the flexible patch 30 for air permeability of the skin sensor 1, and may have a different plane (e.g., a cross) as shown in FIG. 12.

In the above embodiment, at least one key that matches the key hole of the mold 810 may be formed in the semiconductor structure before S1040. In an embodiment, at least one key having a plane shape that matches the hole shape of the key hole may be formed in S1211. The at least one key may be formed using the same material as the material of the electrode 111 and/or the interconnect 112 and/or the same method.

In S1240, after the mold 810 contacts the flexible patch layer 830 to form through-holes, the sacrificial layer 105 is etched (S1250). After the sacrificial layer 105 is removed, the mold 810 is removed to manufacture the skin sensor 1.

As described above, the manufacturing method according to the third embodiment includes forming the semiconductor circuits on the substrate 101 using photo-lithography, and forming the biocompatible PDMS patch 30 that does not hinder skin respiration directly thereon using soft lithography to manufacture the skin sensor 1. Accordingly, there is no need to separately make the semiconductor circuit (i.e., the sensor circuit unit 10) and the flexible patch and bond them, so the complexity of the process reduces and a high device transfer yield can be obtained.

Fourth Embodiment

FIGS. 13A to 13K are schematic conceptual diagrams showing a process of manufacturing a skin sensor, according to a fourth embodiment of the present disclosure.

Referring to FIGS. 12 and 13, a method of manufacturing a skin sensor according to the fourth embodiment of the present disclosure is so much similar to the method of manufacturing a skin sensor according to the third embodiment of FIG. 12, and the manufacturing process will be described primarily based on difference(s) from the third embodiment.

By the method of manufacturing the skin sensor according to the fourth embodiment, the skin sensor 1 having the same structure as the second embodiment may be manufactured. That is, the skin sensor 1 shown in FIGS. 1B and 10 may be manufactured.

The method of manufacturing the skin sensor 1 according to the fourth embodiment of the present disclosure is an all-in one manufacturing process in which the process of manufacturing the flexible patch 30 and the process of manufacturing the semiconductor structure including the sensor circuit unit 10 are not separated. That is, it is different from the method of manufacturing the skin sensor 1 according to the second embodiment in which the process of manufacturing the flexible patch 30 and the process of manufacturing the semiconductor structure are separated.

In the fourth embodiment, the method of manufacturing the skin-adherable skin sensor 1 includes forming a sacrificial layer 105 on a substrate 101 (S1301), forming a sensor circuit unit 10 (S1310), forming a flexible patch layer 830 on the sensor circuit unit 10 (S1330), contacting a mold 810 with the flexible patch layer 830 to form a plurality of through-holes (S1340), etching the sacrificial layer 105 to manufacture the skin sensor 1 (S1350), and removing the mold 810 (S1370).

Meanwhile, the skin sensor 1 of the fourth embodiment has the same structure as the skin sensor 1 of the second embodiment. Accordingly, the sensor circuit unit 10 of the fourth embodiment is formed by forming the sacrificial layer 105, and stacking an active layer 115, an insulating layer 113 and a circuit element (an electrode 111 and/or an interconnect 112) in that order (S1310). That is, S1310 includes forming the active layer 115 (S1311), forming the insulating layer 113 on the active layer 115 (S1313), and forming the electrode 111 and/or the interconnect 112 on the insulating layer 113 (S1315), as shown in FIGS. 13C to 13F.

According to the fourth embodiment, it is possible to manufacture the skin sensor 1 using the active layer 115 with a monocrystalline structure. It is impossible to grow the monocrystalline material directly on the metal sacrificial layer 105.

To grow the monocrystalline semiconductor material, a substrate identical or similar to the monocrystalline semiconductor and the temperature of at least 700° C. or above are needed. Accordingly, instead of forming the monocrystalline active layer 115 directly on the metal sacrificial layer 105, the active layer 115 is formed on the metal sacrificial layer 105 by performing 2DLT stressor transfer using a stressor.

Figure 13A:
Figure 13A:
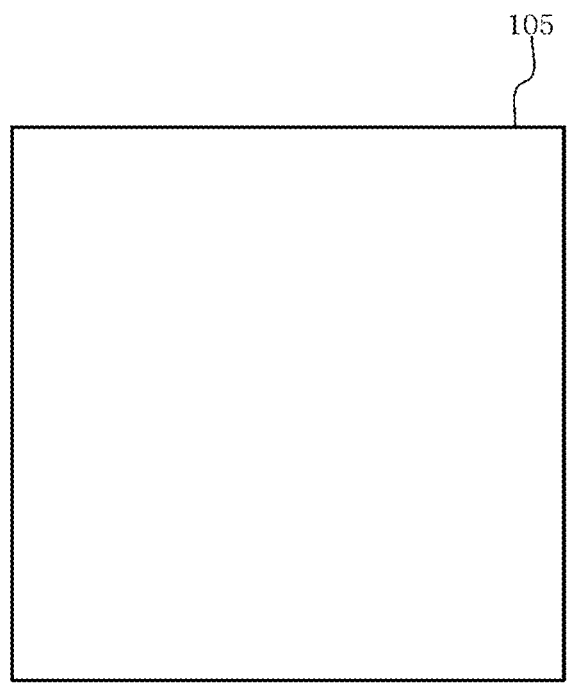
Figure 13B:
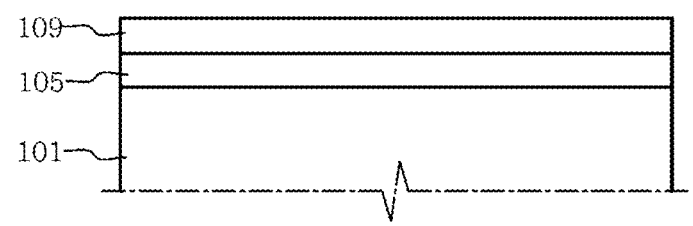
Figure 13B:
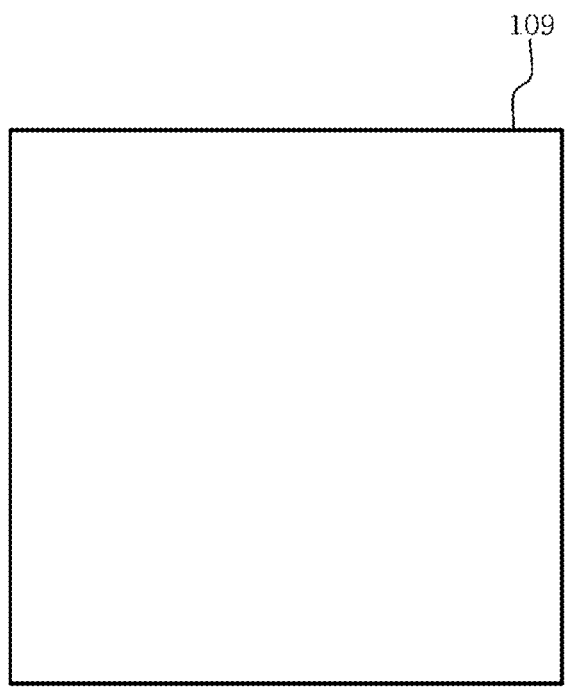
Figure 13D:
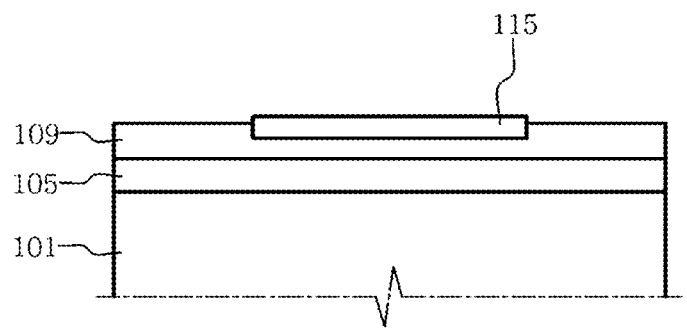
Figure 13D:
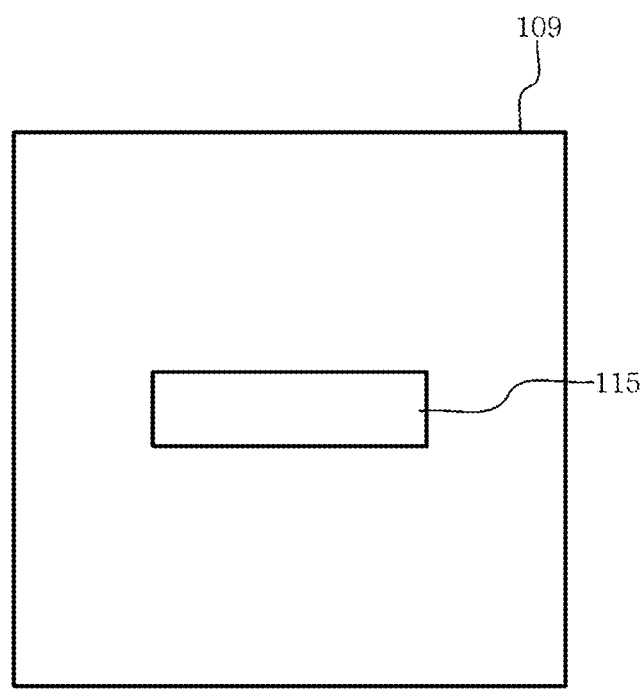

Specifically, as shown in FIGS. 13B and 13C, a process of forming a polyamide layer 109 on the sacrificial layer 105 (S1309), and transferring the monocrystalline thin film (i.e., the active layer 115) peeled by the 2DLT process to the polyamide layer 109 to form an active layer 115 are added (S1311).

In an embodiment, the polyamide layer 109 may be made of a material including polyamide. For example, the polyamide layer 109 is a compound including various elements (fillers), and may be formed with an uncured structure.

Figure 13E:
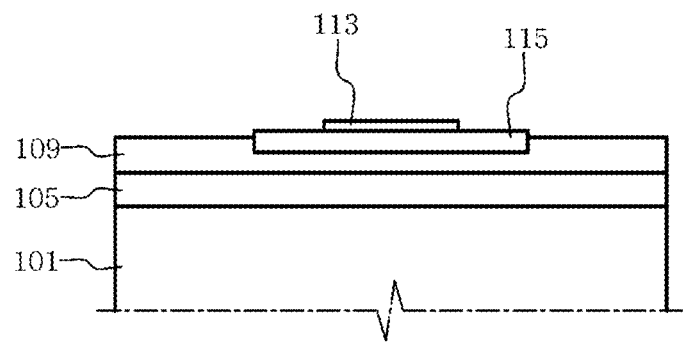
Figure 13E:
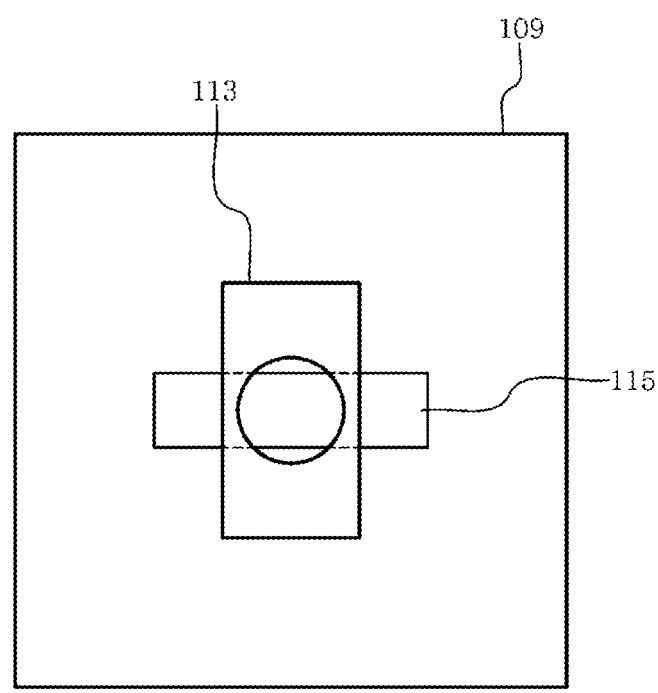
Figure 13F:
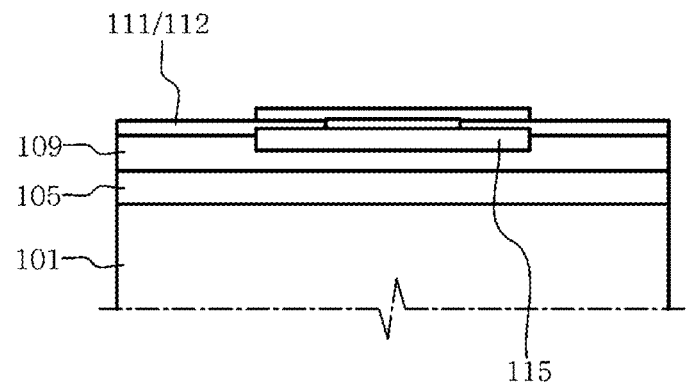
Figure 13F:
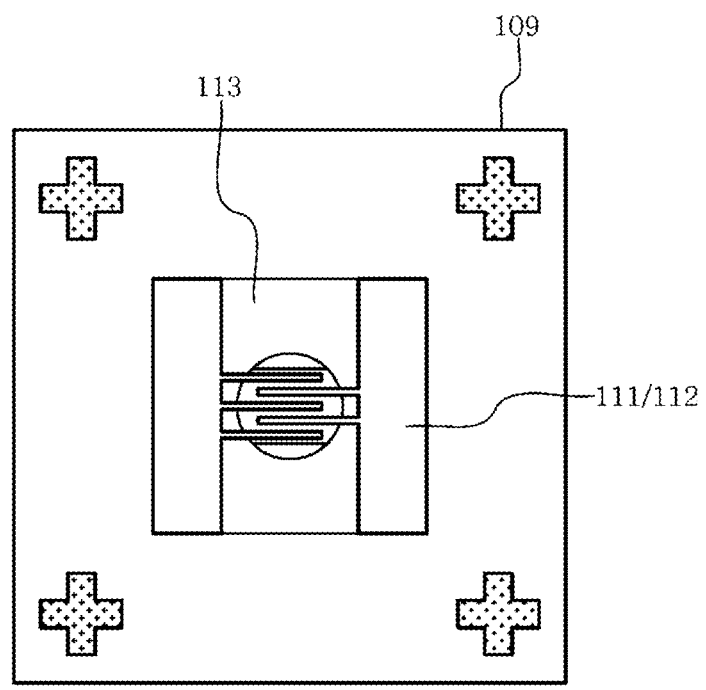
Figure 13G:
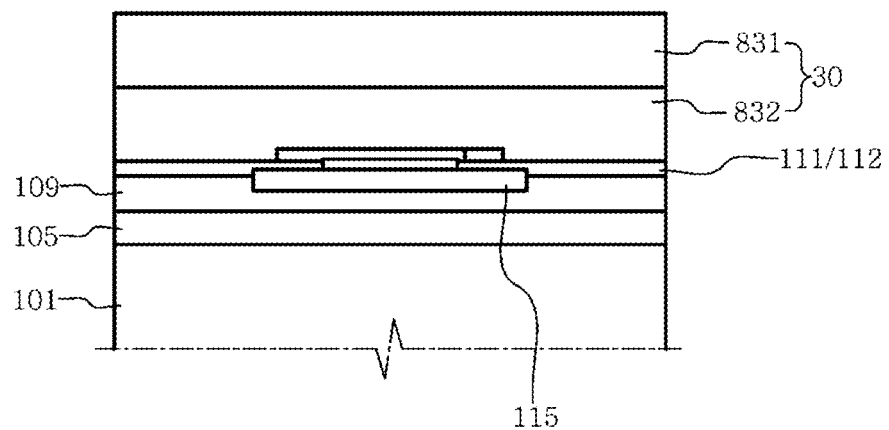
Figure 13G:
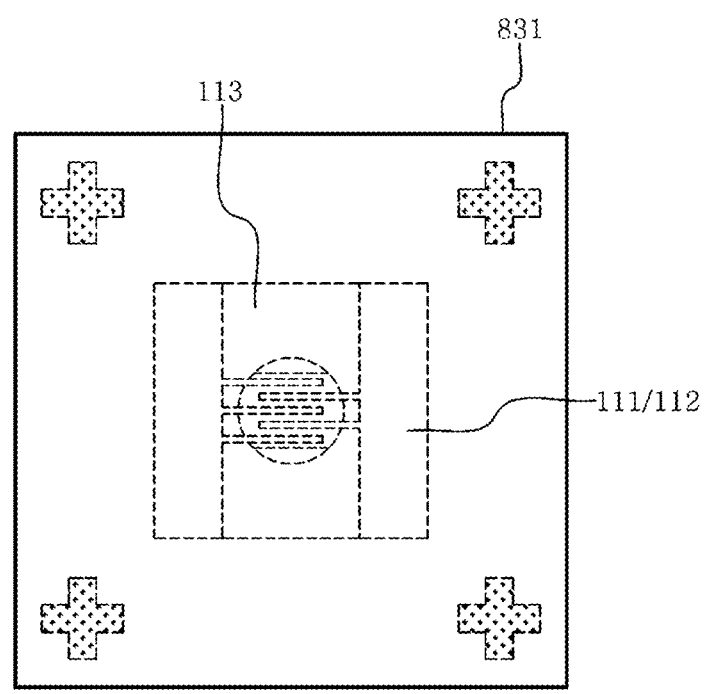
Figure 13H:
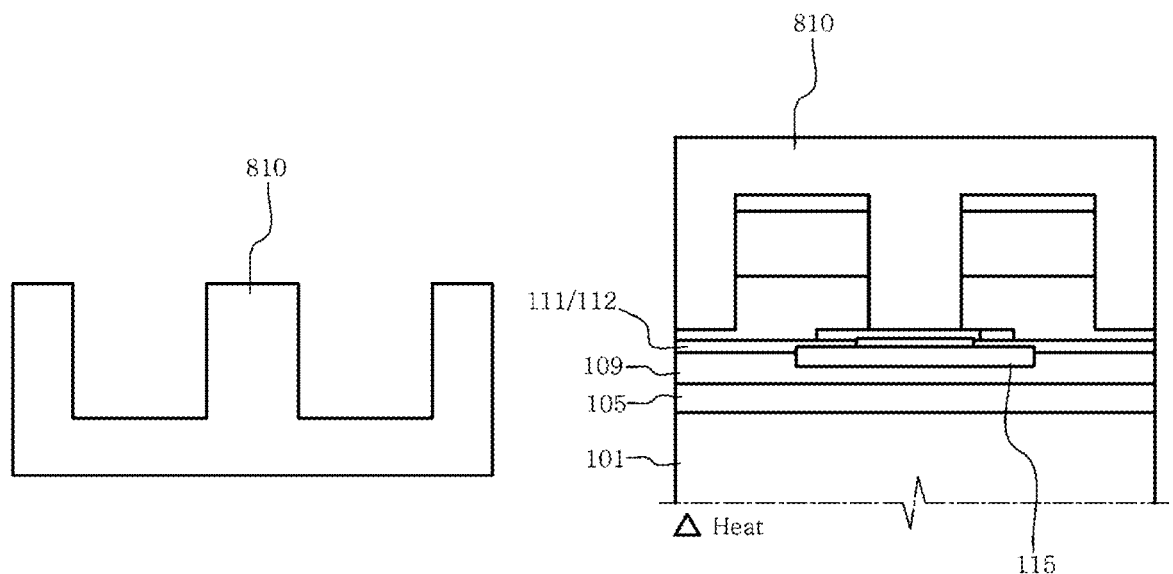
Figure 13H:
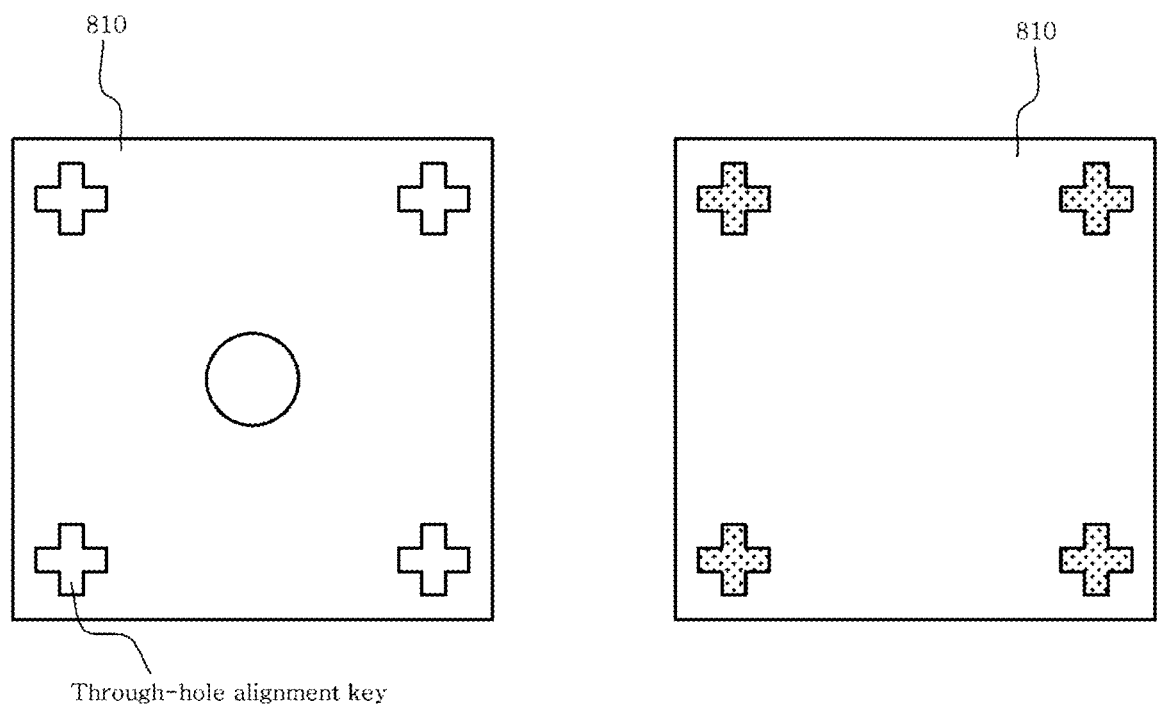
Figure 13I:
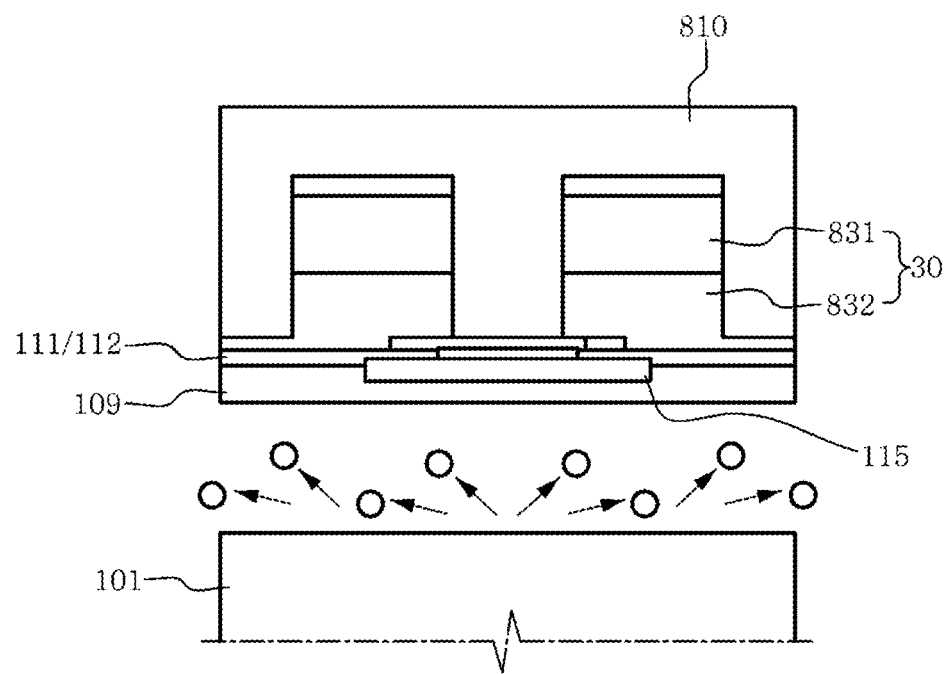
Figure 13J:
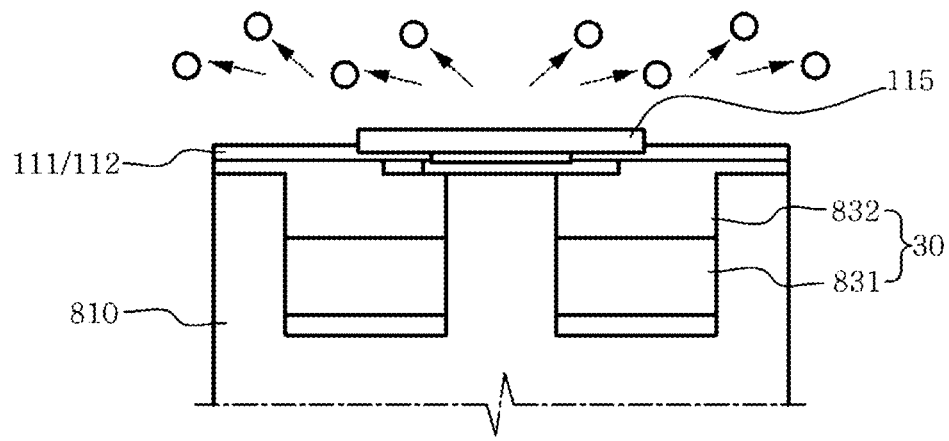
Figure 13J:
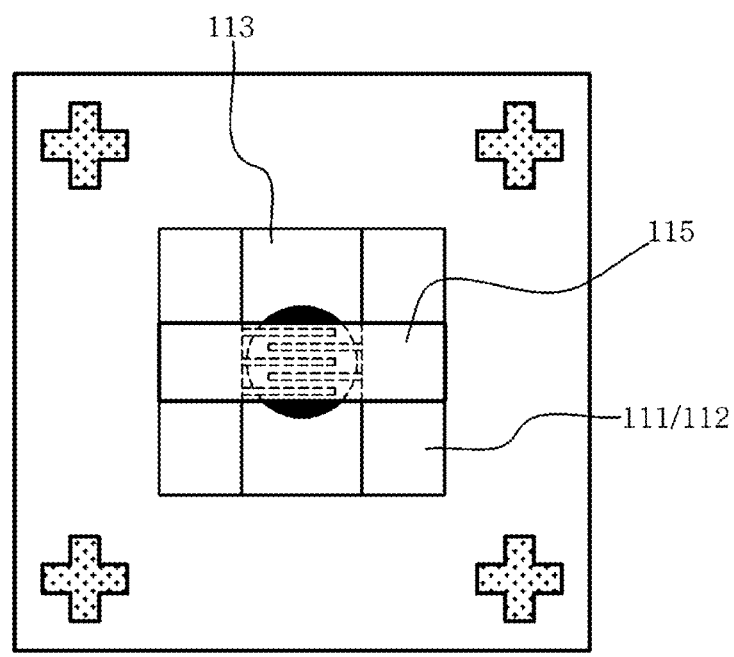
Figure 13K:
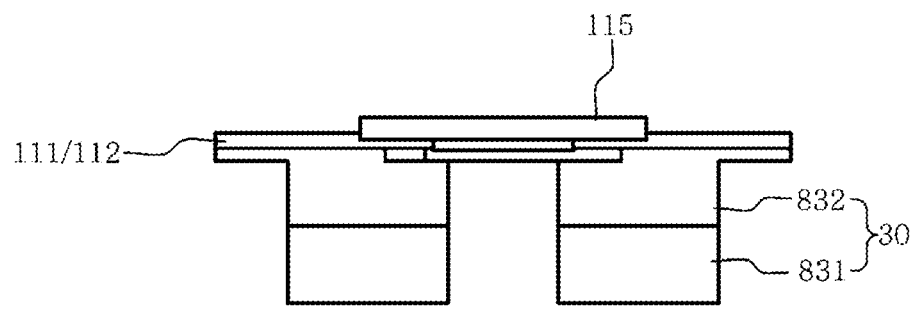
Figure 13K:
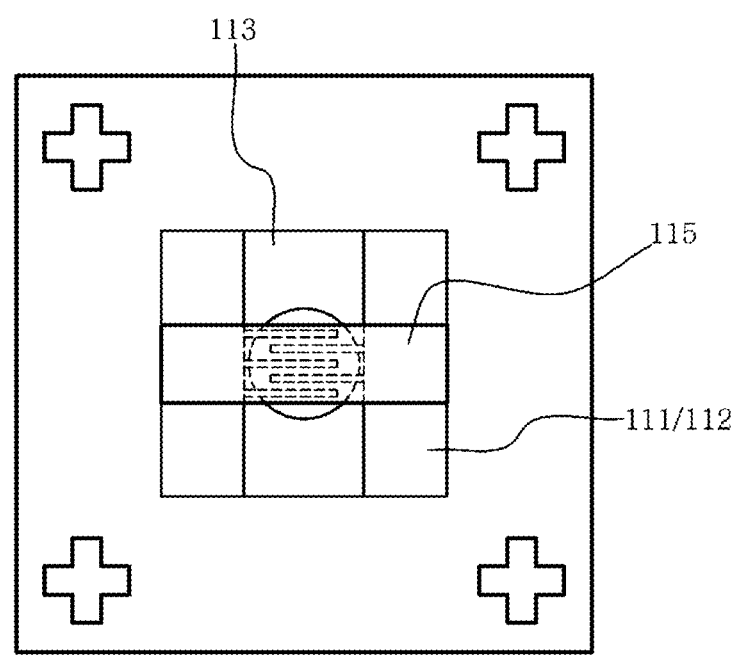

Additionally, S1311 further includes patterning the active layer 115 so that the width of the active layer 115 is smaller than the width of the through-holes of the flexible patch 30. As a result, as shown in FIG. 13E, the through-holes of the flexible patch 30 may be formed on the patterned active layer 115.

In S1311, the active layer 115 is transferred onto the polyamide layer 109 using the active layer 115 and the transfer structure including the stressor layer 730 and the tape layer 750. Subsequently, the stressor layer 730 and the tape layer 750 are removed except the active layer 115 so that only the active layer 115 is disposed on the polyamide layer 109. The formation of the active layer 115 using the transfer structure is similar to the description made with reference to FIG. 7, and its detailed description is omitted herein.

Additionally, the method of manufacturing the skin sensor 1 according to the fourth embodiment further includes removing the polyamide layer 109 (S1360). In an embodiment, the polyamide layer 109 may be removed by plasma etching (for example, including $O_2$ plasma etching).

As described above, according to the embodiments of the present disclosure, the skin-adherable electronic device 1 may be obtained. The electronic device 1 may be manufactured by a process in which the process of forming the semiconductor circuit unit 10 and the process of forming the flexible patch 30 are separated, or the electronic device 1 including the semiconductor circuit unit 10 and the flexible patch 30 may be obtained by an all-in-one process.

The present disclosure has been hereinabove described with reference to the embodiments shown in the drawings, but this is provided for illustration purposes only and those having ordinary skill in the corresponding field will understand that various modifications and variations may be made thereto. However, it should be noted that such modifications fall within the technical protection scope of the present disclosure. Accordingly, the true technical protection scope of the present disclosure shall be defined by the technical spirit of the appended claims.

What is claimed is:

1. A skin-adherable electronic device, comprising:
    a semiconductor circuit unit—the semiconductor circuit unit including a circuit element including at least one of an electrode and an interconnect; and a semiconductor device including an insulating layer and an active layer; and
    a flexible patch including a plurality of through-holes, wherein the flexible patch can adhere to skin,
    wherein the insulating layer includes a plurality of through-holes corresponding to at least some of the plurality of through-holes of the flexible patch and the interconnect includes a plurality of through-holes corresponding to the plurality of through-holes of the insulating layer,
    wherein the at least some of the plurality of through-holes of the flexible patch, the plurality of through-holes of the insulating layer and the plurality of through-holes of the interconnect include circular through-holes and dumbbell through-holes,
    wherein the through-holes of the flexible patch, the through-holes of the insulating layer and the through-holes of the interconnect are aligned to form apertures, and
    wherein skin surfaces are exposed to an air at the apertures when the said device adheres to a skin.

2. The skin-adherable electronic device according to claim 1, wherein spaces between the plurality of through-holes are less than 60 µm respectively.

3. The skin-adherable electronic device according to claim 1, wherein the plurality of through-holes of the flexible patch includes a combination of the first through-hole having a first diameter and second through-holes having second diameters respectively,
    wherein the first diameter is larger than each of second diameters, and the second through-holes are disposed nearby the first through-hole.

4. The skin-adherable electronic device according to claim 1, wherein the at least some of the plurality of through-holes of the flexible patch match the plurality of through-holes of the insulation layer.

5. The skin-adherable electronic device according to claim 1, wherein the active layer is made of a material including AlN or GaN.

6. The skin-adherable electronic device according to claim 1, wherein the circuit element includes a first electrode and a second electrode disposed opposite to the first electrode,
the first electrode includes at least one first bar,
the second electrode includes at least one second bar, and
the first bar has a plane of zigzag shape and extends toward the second electrode, and the second bar has a plane of zigzag shape and extends toward the first electrode.

7. The skin-adherable electronic device according to claim 6, wherein the zigzag shape of the first bar or the second bar includes a hinge pattern disposed at a point where an extension direction of the bar changes.

8. The skin-adherable electronic device according to claim 1, wherein the flexible patch includes a first flexible layer having a first elastic modulus and a second flexible layer having a second elastic modulus, and
the first elastic modulus is lower than the second elastic modulus.

9. The skin-adherable electronic device according to claim 8, wherein a thickness ($t_1$) of the first flexible layer and a thickness ($t_2$) of the second flexible layer are determined based on the following equation:

$W \geq W_c$ where $W_c = E_{eq} * t^3/(24R^2)$, $$W = \frac{4\gamma_{dPatch}\ \gamma_{dskin}}{\gamma_{dPatch} + \gamma_{dskin}} + \frac{4\gamma_{pPatch}\ \gamma_{pskin}}{\gamma_{pPatch} + \gamma_{pskin}},$$

$$E_{eq} = \left(\frac{t_1}{t_1 + t_2}\right)E_1 + \left(\frac{t_2}{t_1 + t_2}\right)E_2$$

$t = t_1 + t_2,$ where t denotes a thickness of the flexible patch, $E_1$ denotes an elastic modulus of the first flexible layer, $E_2$ denotes an elastic modulus of the second flexible layer, R denotes a curvature of the flexible patch adhered to the skin, $\gamma_{dSkin}$ denotes a dispersive component of contact surface of the skin, $\gamma_{dPatch}$ denotes a dispersive component of contact surface of the patch, $\gamma_{pSkin}$ denotes a polar component of contact surface of the skin, and $\gamma_{pPatch}$ denotes a polar component of contact surface of the patch.

10. A method of manufacturing a skin-adherable electronic device according to claim 1, comprising:
forming a sacrificial layer on a first substrate;
forming a semiconductor circuit unit including a semiconductor device and a circuit element on the sacrificial layer,
bonding a flexible patch including a plurality of through-holes onto the semiconductor circuit, and
etching the sacrificial layer to manufacture an electronic device including the semiconductor circuit unit and the flexible patch.

11. The method of manufacturing a skin-adherable electronic device according to claim 10, wherein the forming the semiconductor circuit unit comprises:

forming a circuit element on the sacrificial layer—the circuit element including at least one of an electrode and an interconnect;
forming an insulating layer on the circuit element—the insulating layer being formed to have a plurality of through-holes corresponding to the plurality of through-holes of the flexible patch; and
forming an active layer on the insulating layer.

12. The method of manufacturing a skin-adherable electronic device according to claim 11, wherein the forming the active layer comprises:
forming an active layer on a second substrate;
forming a stressor layer on the active layer;
placing a tape on the stressor layer;
peeling the active layer and the stressor layer off from the second substrate using the tape;
transferring the peeled active layer and stressor layer onto the insulating layer—the peeled active layer being transferred onto the insulating layer; and
peeling the stressor layer off from the active layer using the tape.

13. The method of manufacturing a skin-adherable electronic device according to claim 12, wherein the stressor layer is a multilayer, and
the forming the stressor layer comprises:
forming a first stressor layer on the active layer by evaporation;
forming a second stressor layer on the first stressor layer by sputtering deposition; and
forming a third stressor layer on the second stressor layer by sputtering deposition.

14. The method of manufacturing a skin-adherable electronic device according to claim 13, wherein the second stressor layer is made of a material including Al, and
the third stressor layer is made of a material including Ni.

15. The method of manufacturing a skin-adherable electronic device according to claim 14, wherein the first stressor layer is made of a material including Ni or AgNi.

16. The method of manufacturing a skin-adherable electronic device according to claim 10, wherein the bonding further comprises applying the pressure between the flexible patch and the semiconductor circuit unit.

17. The method of manufacturing a skin-adherable electronic device according to claim 10, further comprising:
performing plasma treatment of the semiconductor circuit unit and the flexible patch before bonding.

18. The method of manufacturing a skin-adherable electronic device according to claim 10, wherein the bonding comprises placing the flexible patch on the active layer so as to match the plurality of through-holes of the flexible patch to the plurality of through-holes of the insulation layer.

19. The method of manufacturing a skin-adherable electronic device according to claim 10, wherein the sacrificial layer is made of any one material of Ni, Cr, Al and their combinations.

20. The method of manufacturing a skin-adherable electronic device according to claim 10, wherein the forming the semiconductor circuit unit comprises:
forming an active layer on the sacrificial layer;
forming an insulating layer on the active layer; and
forming a circuit element on the insulating layer—the circuit element includes at least one of an electrode and an interconnect.

21. A method of manufacturing a skin-adherable electronic device according to claim 1, comprising:
forming a sacrificial layer on a first substrate;

forming a semiconductor circuit unit including a circuit element and a semiconductor device on the sacrificial layer;

forming a flexible patch layer on the semiconductor circuit unit;

contacting a mold including furrows that form a plurality of through-holes with the flexible patch layer—a region of the mold except the furrows passing through the flexible patch layer; and etching the sacrificial layer to manufacture an electronic device.

22. The method of manufacturing a skin-adherable electronic device according to claim 21, wherein the forming the semiconductor circuit unit on the sacrificial layer comprises:

forming a circuit element on the sacrificial layer—the circuit element including at least one of an electrode and an interconnect;

forming an insulating layer on the circuit element—the insulating layer including a plurality of through-holes corresponding to the plurality of through-holes of the flexible patch layer formed by the mold; and forming an active layer on the insulating layer.

23. The method of manufacturing a skin-adherable electronic device according to claim 22, wherein the forming the semiconductor circuit unit on the sacrificial layer comprises:

forming an active layer on the sacrificial layer;

forming an insulating layer on the active layer—the insulating layer including a plurality of through-holes corresponding to the plurality of through-holes of the flexible patch layer formed by the mold; and forming a circuit element on the insulating layer—the circuit element including at least one of an electrode and an interconnect.

24. The method of manufacturing a skin-adherable electronic device according to claim 23, further comprising:

before forming an active layer, forming a polyamide layer on the sacrificial layer; and after contacting the molding with the flexible patch layer, removing the polyamide layer.

25. The method of manufacturing a skin-adherable electronic device according to claim 24, wherein the forming the active layer comprises forming the active layer on the polyamide layer using a transfer structure.

26. The method of manufacturing a skin-adherable electronic device according to claim 23, further comprising:

patterning the active layer such that a width of the active layer is smaller than a width of through-holes that will be formed by the mold.

27. The method of manufacturing a skin-adherable electronic device according to claim 21, wherein the contacting the mold including the plurality of furrows with the flexible patch layer comprises heating the flexible patch layer.

28. The method of manufacturing a skin-adherable electronic device according to claim 21, wherein a surface of the mold has furrows that can form a plurality of circular through-holes and a plurality of dumbbell through-holes and their combinations.

29. The method of manufacturing a skin-adherable electronic device according to claim 22, further comprising:

forming at least one alignment key for alignment of the penetrating mold, wherein the alignment key has a height, and the mold further includes at least one key hole corresponding to a plane of the alignment key.

30. The method of manufacturing a skin-adherable electronic device according to claim 21, wherein a width of the furrows that form the through-holes is less than 60 μm.

31. The method of manufacturing a skin-adherable electronic device according to claim 22, wherein the forming the flexible patch layer comprises:

forming a third flexible layer having a third elastic modulus on the semiconductor circuit unit; and forming a fourth flexible layer having a fourth elastic modulus on the third flexible layer, and the fourth elastic modulus is lower than the third elastic modulus.

\* \* \* \* \*